(12) United States Patent
Thede et al.

(10) Patent No.: US 8,399,682 B2
(45) Date of Patent: *Mar. 19, 2013

(54) SUBSTITUTED (PYRAZOLYLCARBONYL) IMIDAZOLIDINONES AND THEIR USE

(75) Inventors: Kai Thede, Berlin (DE); Susanne Greschat, Duesseldorf (DE); Steffen Wildum, Gevelsberg (DE); Daniela Paulsen, Wuppertal (DE)

(73) Assignee: AiCuris GmbH & Co. KG, Wuppertal (DE)

( * ) Notice: Subject to any disclaimer, the term of this patent is extended or adjusted under 35 U.S.C. 154(b) by 70 days.

This patent is subject to a terminal disclaimer.

(21) Appl. No.: 12/885,340

(22) Filed: Sep. 17, 2010

(65) Prior Publication Data
US 2011/0124618 A1    May 26, 2011

Related U.S. Application Data

(63) Continuation of application No. PCT/EP2009/001714, filed on Mar. 10, 2009.

(30) Foreign Application Priority Data

Mar. 17, 2008    (DE) .................. 10 2008 015 033

(51) Int. Cl.
C07D 233/32    (2006.01)
A61K 31/4166    (2006.01)
(52) U.S. Cl. ..................... 548/312.4; 514/386
(58) Field of Classification Search .................. None
See application file for complete search history.

(56) References Cited

U.S. PATENT DOCUMENTS

| | | | |
|---|---|---|---|
| 3,806,506 A | 4/1974 | Felauer et al. | |
| 4,684,652 A | 8/1987 | Dubroeucq et al. | |
| 5,134,142 A | 7/1992 | Matsuo et al. | |
| 5,432,835 A | 7/1995 | Hashimoto | |
| 5,571,810 A | 11/1996 | Matsuo et al. | |
| 5,624,941 A | 4/1997 | Barth et al. | |
| 5,627,203 A | 5/1997 | Rault et al. | |
| 6,143,780 A | 11/2000 | Brouwer et al. | |
| 7,622,471 B2 | 11/2009 | Kanaya et al. | |
| 2004/0116425 A1 | 6/2004 | Li et al. | |
| 2005/0054707 A1 | 3/2005 | Edwards et al. | |
| 2008/0064682 A1 | 3/2008 | Kanaya et al. | |

FOREIGN PATENT DOCUMENTS

| | | |
|---|---|---|
| DE | 10 2004 054 666 | 5/2006 |
| EP | 0 065 295 | 11/1982 |
| EP | 0 112 776 | 7/1984 |
| EP | 0 418 845 | 3/1991 |
| EP | 0 554 829 | 8/1993 |
| EP | 0 576 357 | 12/1993 |
| EP | 1 591 443 | 11/2005 |
| EP | 1 743 637 | 1/2007 |
| EP | 1 762 568 | 3/2007 |
| WO | WO-91/19708 | 12/1991 |
| WO | WO-94/27979 | 12/1994 |
| WO | WO-97/19940 | 6/1997 |
| WO | WO-02/00649 | 1/2002 |
| WO | WO-02/100853 | 12/2002 |
| WO | WO-03/014107 | 2/2003 |
| WO | WO-03/037274 | 5/2003 |
| WO | WO-2004/016592 | 2/2004 |
| WO | WO-2004/024147 | 3/2004 |
| WO | WO-2004/031178 | 4/2004 |
| WO | WO-2004/050632 | 6/2004 |
| WO | WO 2004069824 A1 * | 8/2004 |
| WO | WO-2004/076453 | 9/2004 |
| WO | WO-2005/000820 | 1/2005 |
| WO | WO-2005/002576 | 1/2005 |
| WO | WO-2005/007625 | 1/2005 |
| WO | WO-2005/035488 | 4/2005 |
| WO | WO-2005/080343 | 9/2005 |
| WO | WO-2006/015860 | 2/2006 |
| WO | WO-2006/023462 | 3/2006 |
| WO | WO-2006/062982 | 6/2006 |
| WO | WO-2006/062984 | 6/2006 |
| WO | WO-2006/065209 | 6/2006 |
| WO | WO-2006/099231 | 9/2006 |
| WO | WO-2007/002559 | 1/2007 |
| WO | WO-2007/009701 | 1/2007 |
| WO | WO-2007/020388 | 2/2007 |
| WO | WO-2008/043775 | 4/2008 |
| WO | WO-2008/080056 | 7/2008 |
| WO | WO-2008/090382 | 7/2008 |
| WO | WO-2009/115213 | 9/2009 |
| WO | WO-2009/115252 | 9/2009 |

OTHER PUBLICATIONS

U.S. Appl. No. 12/884,113, filed Sep. 2010, Substituted Pyrazolamides and Their Use.*
West, M. L.; Fairlie, D. P. "Targeting HIV-1 protease: a test of drug-design methodologies" TIPS, 1995, 16, 67-75.*
Carpenter et al., J. Am. Med. Assoc. (2000) 283:381-390.
Database PubChem, Accession No. ZINC04827711, Sep. 12, 2005.
Database PubChem, Accession No. CID3315199, Sep. 7, 2005.
Database PubChem, Accession No. ZINC04560769, Sep. 18, 2005.
Database PubChem, Accession No. ZINC04374875, Sep. 13, 2005.
Database PubChem, Accession No. ZINC04908325, Sep. 14, 2005.
Database PubChem, Accession No. ZINC04407915, Sep. 18, 2005.
Finzi et al., Nature Med. (1999) 5:512-517.
Flexner, Nature Reviews Drug Discovery (2007) 6:959-966.
Genin et al., J. Med. Chem. (2000) 43:1034-1040.

(Continued)

*Primary Examiner* — Yong Chong
*Assistant Examiner* — Jason A Deck
(74) *Attorney, Agent, or Firm* — Morrison & Foerster LLP

(57) ABSTRACT

The present invention relates to novel substituted (pyrazolylcarbonyl)imidazolidinones, methods for their preparation, their use for the treatment and/or prophylaxis of diseases, as well as their use for the manufacture of medicaments for the treatment and/or prophylaxis of diseases, especially of retroviral diseases, in humans and/or animals.

26 Claims, No Drawings

OTHER PUBLICATIONS

International Search Report for PCT/EP2009/001714, mailed on May 12, 2009, 2 pages.
International Preliminary Report on Patentability for PCT/EP2009/001714, issued on Oct. 5, 2010, 5 pages.
Kavlick and Mitsuya, Antiretroviral Chemotherapy (Hrsg. De Clercq E.) (2001) ASM Press, pp. 279-312.
Medveczky et al., BMC Medicine (2004) 2:34 1-9.
Palella et al., New England Journal of Medicine (1998) 238:853-860.
Ramratnam et al., Nature Med. (2000) 6:82-85.
Richman, Nature (2001) 410:995-1001.
International Search Report for PCT/EP2009/001877, mailed on Feb. 11, 2010, 6 pages.
International Preliminary Report on Patentability for PCT/EP2009/001877, issued on Oct. 5, 2010, 9 pages.
Kort et al., J. Med. Chem. (2008) 51:407-416.
Romero et al., Journal of Medicinal Chemistry (1994) 37:999-1014.
O'Neill, "The Diversity of Retroviral Diseases of the Immune System," Immunology and Cell Biology (1992) 70:193-199.
Van Rompay, "Evaluation of Antiretrovirals in Animal Models of HIV Infection," Antiviral Research (2010) 85:159-175.
Non-Final Office Action for U.S. Appl. No. 12/884,113, mailed Jan. 26, 2012.
Response to Non-Final Office Action for U.S. Appl. No. 12/884,113, mailed Apr. 18, 2012.
Non-Final Office Action for U.S. Appl. No. 13/162,521, mailed Dec. 23, 2011.
Response to Non-Final Office Action for U.S. Appl. No. 13/162,521, mailed Mar. 22, 2012.
Supplemental Response to Non-Final Office Action for U.S. Appl. No. 13/162,521, mailed Mar. 29, 2012.
Non-Final Office Action for U.S. Appl. No. 13/162,522, mailed Dec. 21, 2011.
Response to Non-Final Office Action for U.S. Appl. No. 13/162,522, mailed Mar. 20, 2012.
Non-Final Office Action for U.S. Appl. No. 13/162,522 mailed Jun. 22, 2012.
Notice of Allowance for U.S. Appl. No. 12/884,113, mailed Jul. 12, 2012.
Notice of Allowance for U.S. Appl. No. 13/162,521, mailed Aug. 3, 2012.
Office Action for U.S. Appl. No. 13/162,522, mailed Nov. 23, 2012.

* cited by examiner

SUBSTITUTED (PYRAZOLYLCARBONYL) IMIDAZOLIDINONES AND THEIR USE

CROSS REFERENCE OF RELATED APPLICATIONS

This application is a continuation of pending international application PCT/EP2009/001714, filed Mar. 10, 2009, designating US, which claims priority from German patent application DE 10 2008 015 033.9, filed Mar. 17, 2008. The contents of each of these documents is incorporated herein by reference in its entirety.

BACKGROUND OF THE INVENTION

The present invention relates to novel substituted (pyrazolylcarbonyl)imidazolidinones, methods for their preparation, their use for the treatment and/or prophylaxis of diseases, as well as their use for the manufacture of medicaments for the treatment and/or prophylaxis of diseases, especially of retroviral diseases, in humans and/or animals.

HIV (human immunodeficiency virus) causes a chronic persistent progressive infection. The disease proceeds via various stages from the asymptomatic infection to the pathological condition AIDS (acquired immunodeficiency syndrome). AIDS is the final stage of the disease caused by infection. The HIV/AIDS disease is characterized by a long clinical latency period with persistent viraemia which, in the final stage, leads to the failure of the immune defences.

The introduction of the anti-HIV combination therapy made it possible in the 1990s to effectively slow the down progression of the disease and thus to prolong substantially the life expectancy of HIV-infected patients (Palella et al., *N. Engl. J. Med.* 1998, 238, 853-860).

The anti-HIV substances currently on the market inhibit the replication of the HI virus by inhibiting the essential viral enzymes reverse transcriptase (RT), protease or integrase, or the entry of HIV into the target cell (review in Flexner, *Nature Reviews Drug Discovery* 2007, 6, 959-966). There are two classes of RT inhibitors: nucleosidic and nucleotidic RT inhibitors (NRTI) act through competitive inhibition or chain termination in the DNA polymerization. Non-nucleosidic RT inhibitors (NNRTI) bind allosterically to a hydrophobic pocket in the vicinity of the active centre of the RT and bring about a conformational change in the enzyme. The currently available protease inhibitors (PI) block the active centre of the viral protease and thus prevent the maturation newly produced particles into infectious virions. The only currently authorized integrase inhibitor Raltegravir binds in the active centre of the HIV integrase and prevents the integration of the proviral DNA into the host cell genome. Entry inhibitors (fusion inhibitors and coreceptor antagonists) prevent the HIV infection of cells by interacting with the HIV coat protein or by blocking the cellular coreceptors CCR5 or CXCR4.

Since monotherapy with the currently available anti-HIV medicaments leads in a very short time to a failure of the therapy owing to a selection of resistant viruses, usually a combination therapy with several anti-HIV substances from different classes takes place (highly active antiretroviral therapy=HAART; Carpenter et al., *J. Am. Med. Assoc.* 2000, 283, 381-390).

Despite the advances in antiretroviral chemotherapy, recent investigations show that an eradication of HIV and, associated therewith, a cure of the HIV infection is not to be expected with the available medicaments. The latent virus remains in dormant lymphocytes and represents a reservoir for a reactivation and thus for a renewed spread of the virus (Finzi et al., *Nature Med.* 1999, 5, 512-517; Ramratnam et al., *Nature Med.* 2000, 6, 82-85). HIV-infected patients are therefore life-long dependent on an efficient antiviral therapy. Despite combination therapy, a selection of resistant viruses occurs after some time. Since resistance mutations characteristic for each therapeutic class accumulate, the failure of one therapy often means a loss of effect of the complete class of substances. This cross-resistance problem is most pronounced with the class of NNRTIs because in this case a single point mutation in the RT may often be sufficient to bring about a loss of effect of all NNRTIs (review in Kavlick & Mitsuya, *Antiretroviral Chemotherapy* (editor De Clercq E.), 2001, ASM Press, 279-312).

The development of resistances is usually favoured by the poor compliance of the patients which is caused by an unfavourable profile of side effects and a complicated dosage regimen for the anti-HIV medicaments.

There is thus a pressing need for novel therapeutic options for controlling an HIV infection. For this purpose, an urgent aim of HIV therapy research is to identify novel chemical lead structures which either address a novel target in the replication of HIV and/or are effective against the growing number of resistant clinical HIV isolates.

U.S. Pat. No. 5,624,941 and EP 576357 describe pyrazoles as cannabinoid receptor antagonists, EP 418845, EP 554829 and WO 04/050632 inter alia for the treatment of inflammatory and thrombotic diseases, WO 03/037274 as sodium ion channel inhibitors for the treatment of pain, WO 06/015860 as adenosine receptor ligands for the treatment of inflammatory and obstructive respiratory diseases, EP 1762568 and EP 1591443 as inhibitors of platelet aggregation, WO 07/002, 559 as modulators of the activity of nuclear receptors, WO 07/020,388 and WO 05/080343 as cannabinoid receptor modulators inter alia for the treatment of obesity and psychiatric and neurological disorders, WO 07/009,701 and EP 1743637 for the treatment of cardiovascular risk factors, WO 2005/002576 as inhibitors of various kinases and, DE 10 2004 054 666 for controlling harmful plants or for plant growth regulation.

SUMMARY OF THE INVENTION

One object of the present invention is therefore to provide novel compounds with the same or improved antiviral activity for the treatment of viral infectious diseases in humans and animals which do not have the disadvantages described previously.

It has surprisingly been found that the substituted (pyrazolylcarbonyl)imidazolidinones described in the present invention have antiviral activity.

The invention relates to compounds of formula

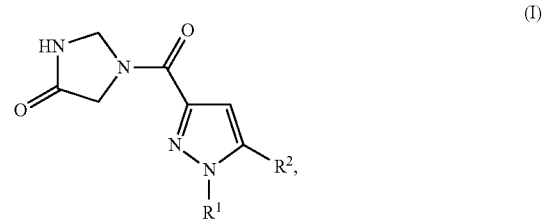

(I)

in which
$R^1$ represents phenyl,
whereby phenyl is substituted with 1 to 3 substituents,
whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy, wherein $(C_1-C_4)$-alkyl and $(C_1-C_4)$-alkoxy in turn may be substituted once to three times, identically or differently, with radicals selected from the series halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl, whereby the last-mentioned cycloalkyl and heterocyclyl radicals in turn may each be substituted up to three times, identically or differently, with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino, $R^2$ represents phenyl, whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy, wherein $(C_1-C_4)$-alkyl and $(C_1-C_4)$-alkoxy in turn may be substituted once to three times, identically or differently, with radicals selected from the series halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl, whereby the last-mentioned cycloalkyl and heterocyclyl radicals in turn may each be substituted up to three times, identically or differently, with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino, and the salts thereof, the solvates thereof and the solvates of the salts thereof.

Compounds of the invention are the compounds of formula (I) and the salts, solvates and solvates of the salts thereof, as well as the compounds which are encompassed by formula (I) and are mentioned hereinafter as exemplary embodiment(s), and the salts, solvates and solvates of the salts thereof, insofar as the compounds encompassed by formula (I) and mentioned hereinafter are not already salts, solvates and solvates of the salts.

The compounds of the invention may, depending on their structure, exist in stereoisomeric forms (enantiomers, diastereomers). The invention therefore also encompasses the enantiomers or diastereomers and respective mixtures thereof. The stereoisomerically uniform constituents can be isolated in a known manner from such mixtures of enantiomers and/or diastereomers.

If the compounds of the invention may occur in tautomeric forms, the present invention encompasses all tautomeric forms.

Salts preferred for the purposes of the present invention are physiologically acceptable salts of the compounds of the invention. Also encompassed however are salts which are themselves not suitable for pharmaceutical applications but can be used for example for the isolation or purification of the compounds of the invention.

Physiologically acceptable salts of the compounds of the invention include acid addition salts of mineral acids, carboxylic acids and sulfonic acids, e.g. salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purposes of the invention refer to those forms of the compounds of the invention which in the solid or liquid state form a complex by coordination with solvent molecules. Hydrates are a specific form of solvates in which the coordination takes place with water.

In the context of the present invention, the substituents have the following meaning, unless specified otherwise:

Alkyl and the alkyl moieties in alkoxy and alkoxycarbonyl represent straight-chain or branched alkyl and include, unless indicated otherwise, $(C_1-C_6)$-alkyl, in particular $(C_1-C_4)$-alkyl such as, for example, methyl, ethyl, propyl, isopropyl, butyl, isobutyl, t-butyl.

Alkoxy for the purpose of the invention represents preferably a straight-chain or branched alkoxy radical in particular having 1 to 6, 1 to 4 or 1 to 3 carbon atoms. A straight-chain or branched alkoxy radical having 1 to 3 carbon atoms is preferred. Mention may be made by way of example and preferably of: methoxy, ethoxy, n-propoxy, isopropoxy, t-butoxy, n-pentoxy and n-hexoxy.

Alkoxycarbonyl represents by way of example and preferably methoxycarbonyl, ethoxycarbonyl, n-propoxycarbonyl, isopropoxycarbonyl, t-butoxycarbonyl, n-pentoxycarbonyl and n-hexoxycarbonyl.

Heterocyclyl represents a monocyclic heterocyclic radical having 4 to 7, preferably 5 to 6, ring atoms and up to 3, preferably up to 2, heteroatoms and/or hetero groups from the series N, O, S, SO, $SO_2$, whereby a nitrogen atom can also form an N-oxide. The heterocycle may be saturated or partly unsaturated. Preference is given to 5- to 7-membered monocyclic saturated heterocycles having up to two heteroatoms from the series O, N and S, by way of example and preferably 1,4-oxazepanyl, pyrrolidin-1-yl, pyrrolidin-2-yl, pyrrolidin-3-yl, tetrahydrofuranyl, tetrahydrothienyl, pyranyl, 1,3-thiazolidinyl, piperidin-1-yl, piperidin-2-yl, piperidin-3-yl, piperidin-4-yl, thiopyranyl, morpholin-2-yl, morpholin-3-yl, morpholin-4-yl, thiomorpholin-2-yl, thiomorpholin-3-yl, thiomorpholin-4-yl, perhydroazepinyl, piperazin-1-yl, piperazin-2-yl.

Halogen represents fluorine, chlorine, bromine or iodine, with preference for fluorine and chlorine, unless indicated otherwise.

Mono-$(C_1-C_4)$-alkylamino for the purpose of the invention represents an amino group having a straight-chain or branched alkyl substituent which comprises 1 to 4 carbon atoms. Mention may be made by way of example and preferably of: methylamino, ethylamino, n-propylamino, isopropylamino, n-butylamino, tert-butylamino, n-pentylamino and n-hexylamino.

Di-$(C_1-C_4)$-alkylamino for the purpose of the invention represents an amino group having two identical or different straight-chain or branched alkyl substituents which each comprise 1 to 4 carbon atoms. Mention may be made by way of example and preferably of: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-methyl-N-n-pentylamino and N-n-hexyl-N-methylamino.

($C_3$-$C_7$)-Cycloalkyl for the purpose of the invention represents a monocyclic saturated carbocycle having 3 to 7 or 3 to 6 ring carbon atoms. Mention may be made by way of example and preferably of: cyclopropyl, cyclobutyl, cyclopentyl, cyclohexyl and cycloheptyl.

The radical definitions listed above and indicated in general or in preferred ranges apply both to the final products of formula (I) and correspondingly to the starting materials and intermediates required for the preparation in each case.

The radical definitions indicated specifically in the respective combinations or preferred combinations of radicals are replaced irrespective of the particular combinations of radicals indicated as desired also by radical definitions of other combinations.

The invention also relates to compounds of formula (I) in which
$R^1$ represents phenyl,
whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, ($C_1$-$C_4$)-alkyl and ($C_1$-$C_4$)-alkoxy,
$R^2$ represents phenyl,
whereby phenyl is substituted with 1 to 2 substituents, whereby the substituents are selected independently of one another from the group consisting of halogen, hydroxy, cyano, nitro, trifluoromethoxy, trifluoromethylthio, ($C_1$-$C_4$)-alkyl and ($C_1$-$C_4$)-alkoxy,
wherein
($C_1$-$C_4$)-alkoxy in turn may be substituted once to three times, identically or differently, with radicals selected from the series halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl and 4- to 7-membered heterocyclyl,
whereby the last-mentioned cycloalkyl and heterocyclyl radicals in turn may each be substituted up to three times, identically or differently, with halogen, cyano, ($C_1$-$C_4$)-alkyl, trifluoromethyl, hydroxy, ($C_1$-$C_4$)-alkoxy, trifluoromethoxy, oxo, amino, mono-($C_1$-$C_4$)-alkylamino and di-($C_1$-$C_4$)-alkylamino,
and the salts thereof, the solvates thereof and the solvates of the salts thereof.

The invention also relates to compounds of formula (I) in which
$R^1$ represents phenyl,
whereby phenyl is substituted with 1 to 2 substituents, whereby the substituents are selected independently of one another from the group consisting of halogen, cyano, trifluoromethyl and methoxy,
$R^2$ represents phenyl,
whereby phenyl is substituted with 1 to 2 substituents, whereby the substituents are selected independently of one another from the group consisting of halogen, cyano, trifluoromethoxy, methyl and ($C_1$-$C_3$)-alkoxy,
wherein
($C_1$-$C_3$)-alkoxy in turn may be substituted once to three times, identically or differently, with radicals selected from the series hydroxy, ($C_1$-$C_4$)-alkoxy, amino, mono-($C_1$-$C_4$)-alkylamino, di-($C_1$-$C_4$)-alkylamino and 4- to 7-membered heterocyclyl,
whereby the last-mentioned heterocyclyl radicals may in turn each be substituted with ($C_1$-$C_4$)-alkyl,
and the salts thereof, the solvates thereof and the solvates of the salts thereof.

The invention also relates to compounds of formula (I) in which
$R^1$ represents phenyl,
whereby phenyl is substituted with 1 to 2 substituents, whereby the substituents are selected independently of one another from the group consisting of halogen, cyano, trifluoromethyl and methoxy,
$R^2$ represents phenyl,
whereby phenyl is substituted with 1 to 2 substituents, whereby the substituents are selected independently of one another from the group consisting of halogen, cyano, trifluoromethoxy, methyl and methoxy,
and the salts thereof, the solvates thereof and the solvates of the salts thereof.

The invention also relates to compounds of formula (I) in which
$R^1$ represents phenyl,
whereby phenyl is substituted with 1 to 2 substituents, whereby the substituents are selected independently of one another from the group consisting of halogen and cyano,
$R^2$ represents phenyl,
whereby phenyl is substituted with 1 to 2 substituents, whereby the substituents are selected independently of one another from the group consisting of halogen and cyano,
and the salts thereof, the solvates thereof and the solvates of the salts thereof.

The invention also relates to compounds of formula

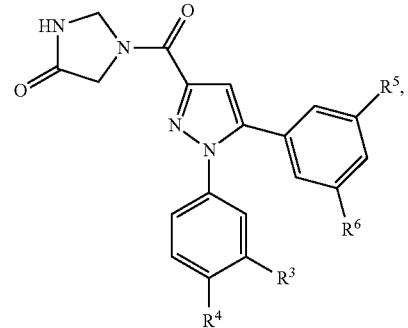

(Ia)

in which
$R^3$ represents hydrogen, halogen, hydroxy, cyano, nitro, trifluoromethyl, trifluoromethoxy, trifluoromethylthio, ($C_1$-$C_4$)-alkyl or ($C_1$-$C_4$)-alkoxy,
$R^4$ represents hydrogen or halogen,
$R^5$ represents halogen, hydroxy, cyano, nitro, trifluoromethyl, trifluoromethoxy, trifluoromethylthio, ($C_1$-$C_4$)-alkyl or ($C_1$-$C_4$)-alkoxy,
wherein
($C_1$-$C_4$)-alkoxy in turn may be substituted once to three times, identically or differently, with radicals selected from the series halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl and 4- to 7-membered heterocyclyl,
whereby the last-mentioned cycloalkyl and heterocyclyl radicals in turn may each be substituted up to three times, identically or differently, with halogen, cyano, ($C_1$-$C_4$)-alkyl, trifluoromethyl, hydroxy, ($C_1$-$C_4$)- alkoxy, trifluoromethoxy, oxo, amino, mono-$(C_1-C_4)$-alkylamino and di-$(C_1-C_4)$-alkylamino, $R^6$ represents hydrogen or halogen, and the salts thereof, the solvates thereof and the solvates of the salts thereof.

The invention also relates to compounds of formula (Ia) in which $R^3$ represents halogen, hydroxy, cyano, nitro, trifluoromethyl, trifluoromethoxy, trifluoromethylthio, $(C_1-C_4)$-alkyl or $(C_1-C_4)$-alkoxy, $R^4$ represents hydrogen or halogen, $R^5$ represents halogen, hydroxy, cyano, nitro, trifluoromethoxy, trifluoromethylthio, $(C_1-C_4)$-alkyl or $(C_1-C_4)$-alkoxy, wherein $(C_1-C_4)$-alkoxy in turn may be substituted once to three times, identically or differently, with radicals selected from the series halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl, whereby the last-mentioned cycloalkyl and heterocyclyl radicals in turn may each be substituted up to three times, identically or differently, with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino, $R^6$ represents hydrogen or halogen, and the salts thereof, the solvates thereof and the solvates of the salts thereof.

The invention also relates to compounds of formula (Ia) in which $R^3$ represents halogen, cyano, trifluoromethyl or methoxy, $R^4$ represents hydrogen or halogen, $R^5$ represents halogen, cyano, trifluoromethoxy, methyl or $(C_1-C_3)$-alkoxy, wherein $(C_1-C_3)$-alkoxy in turn may be substituted once to three times, identically or differently, with radicals selected from the series hydroxy, $(C_1-C_4)$-alkoxy, amino, mono-$(C_1-C_4)$-alkylamino, di-$(C_1-C_4)$-alkylamino and 4- to 7-membered heterocyclyl, whereby the last-mentioned heterocyclyl radicals in turn may each be substituted with $(C_1-C_4)$-alkyl, $R^6$ represents hydrogen or halogen, and the salts thereof, the solvates thereof and the solvates of the salts thereof.

The invention also relates to compounds of formula (Ia) in which $R^3$ represents halogen, cyano, trifluoromethyl or methoxy, $R^4$ represents hydrogen, chlorine or fluorine, $R^5$ represents halogen, cyano, trifluoromethoxy, methyl or methoxy, $R^6$ represents hydrogen, chlorine or fluorine, and the salts thereof, the solvates thereof and the solvates of the salts thereof.

The invention also relates to compounds of formula (Ia) in which $R^3$ represents halogen or cyano, $R^4$ represents hydrogen or fluorine, $R^5$ represents halogen or cyano, $R^6$ represents hydrogen or fluorine, and the salts thereof, the solvates thereof and the solvates of the salts thereof.

The invention also relates to compounds of formula (Ia) in which $R^3$ represents chlorine or cyano, $R^4$ represents fluorine, $R^5$ represents chlorine or cyano, $R^6$ represents fluorine, and the salts thereof, the solvates thereof and the solvates of the salts thereof.

The invention also relates to compounds of formula (Ia) in which $R^3$ represents chlorine or cyano, $R^4$ represents fluorine, $R^5$ represents chlorine or cyano, $R^6$ represents hydrogen, and the salts thereof, the solvates thereof and the solvates of the salts thereof.

The invention also relates to compounds of formula (Ia) in which $R^3$ represents chlorine or cyano, $R^4$ represents hydrogen, $R^5$ represents chlorine or cyano, $R^6$ represents hydrogen, and the salts thereof, the solvates thereof and the solvates of the salts thereof.

The invention also relates to compounds of formula (Ia) in which $R^3$ represents chlorine or cyano, $R^4$ represents hydrogen, $R^5$ represents chlorine or cyano, $R^6$ represents fluorine, and the salts thereof, the solvates thereof and the solvates of the salts thereof.

The invention also relates to compounds of formula (Ia) in which $R^3$ represents halogen, cyano, trifluoromethyl or methoxy, $R^4$ represents hydrogen or halogen, $R^5$ represents trifluoromethyl, $R^6$ represents fluorine, and the salts thereof, the solvates thereof and the solvates of the salts thereof.

The invention also relates to compounds of formula (Ia) in which $R^3$ represents hydrogen, $R^4$ represents fluorine or chlorine, $R^5$ represents halogen, cyano, trifluoromethoxy, methyl or methoxy, $R^6$ represents hydrogen or halogen, and the salts thereof, the solvates thereof and the solvates of the salts thereof.

The invention further relates to a method for preparing the compounds of formula (I) and (Ia), whereby compounds of formula

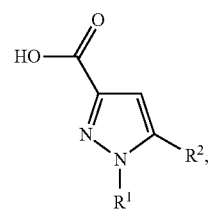

(II)

in which $R^1$ and $R^2$ have the meaning indicated above, are reacted with imidazolidin-4-one or a salt of imidazolidin-4-one.

The reaction generally takes place in inert solvents in the presence of a dehydrating reagent, where appropriate in the presence of a base, preferably in a temperature range from −30° C. to 50° C. under atmospheric pressure.

Examples of inert solvents are halohydrocarbons such as dichloromethane or trichloromethane, hydrocarbons such as benzene or toluene, nitromethane, tetrahydrofuran, 1,4-dioxane, dimethylformamide or acetonitrile. It is likewise possible to employ mixtures of the solvents. Dichloromethane, dimethylformamide, tetrahydrofuran or toluene are particularly preferred.

Examples of bases are alkali metal carbonates such as, for example, sodium or potassium carbonate, or bicarbonate, or organic bases such as trialkylamines, e.g. triethylamine, N-methylmorpholine, N-methylpiperidine, 4-dimethylaminopyridine or diisopropylethylamine.

Examples of suitable dehydrating reagents in this connection are carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino)phosphonium hexafluorophosphate (PyBOP), or N-hydroxysuccinimide, or mixtures thereof, with bases.

The condensation is preferably carried out with PyBOP, TBTU or with EDC in the presence of HOBt.

In an alternative method, the compounds of formula (II) can initially be reacted with thionyl chloride and in the second stage with imidazolidin-4-one or a salt of imidazolidin-4-one in the presence of a base such as, for example, triethylamine.

The compounds of formula (I) and (Ia) prepared by the methods indicated above carry protecting groups where appropriate which can be removed under conditions known to a person skilled in the art in order to obtain further compounds of formula (I) and (Ia).

The compounds of formula (II) are known or can be prepared by hydrolyzing the ester in compounds of formula

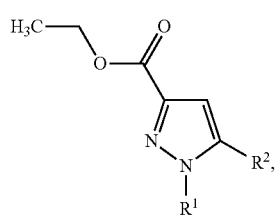

in which
R¹ and R² have the meaning indicated above,
with a base.

The hydrolysis of the ester with a base generally takes place in inert solvents, preferably in a temperature range from room temperature to the reflux of the solvent under atmospheric pressure.

Examples of bases are alkali metal hydroxides such as sodium, lithium or potassium hydroxide, or alkali metal carbonates such as caesium carbonate, sodium or potassium carbonate, with preference for lithium, potassium or sodium hydroxide.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, 1,2-dimethoxyethane, 1,4-dioxane, tetrahydrofuran, glycol dimethyl ether or diethylene glycol dimethyl ether, alcohols such as methanol, ethanol, n-propanol, isopropanol, n-butanol or tert-butanol, hydrocarbons such as benzene, xylene, toluene, hexane, cyclohexane or petroleum fractions, or other solvents such as dimethylformamide, dimethylacetamide, dimethyl sulfoxide, acetonitrile or pyridine, or water, or mixtures of solvents. Preferred solvents are 1,4-dioxane, tetrahydrofuran and/or methanol. Lithium hydroxide in tetrahydrofuran- or 1,4-dioxane-water mixtures or potassium hydroxide in methanol is preferred.

The compounds of formula (III) are known or can be prepared by reacting in the first stage compounds of formula

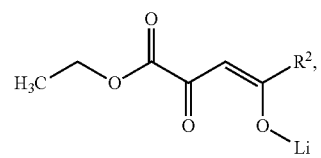

in which
R² has the meaning indicated above,
with compounds of formula $R^1—NH—NH_2$ (V), or a salt of the compounds of formula (V),
in which
R¹ has the meaning indicated above,
and in the second stage heating in acetic acid.

The reaction in the first stage generally takes place in inert solvents, preferably in a temperature range from room temperature to the reflux of the solvent under atmospheric pressure.

Examples of inert solvents are alcohols such as methanol, ethanol, n-propanol, iso-propanol, n-butanol, tert-butanol or 2-methoxyethanol, with preference for ethanol.

The reaction of the second stage in acetic acid generally takes place in a temperature range from room temperature to the reflux of the acetic acid under atmospheric pressure. The reaction can also be carried out in methanol, ethanol or dioxane in a temperature range from room temperature to reflux of the solvents. Mixtures of methanol, ethanol or dioxane with acetic acid in the ratio from 0.5/99.5 to 99.5/0.5 by volume are suitable. It is also possible to employ mixtures of methanol, ethanol, dioxane or acetic acid with other acids such as, for example, hydrochloric acid, methanesulfonic acid, p-toluenesulfonic acid, camphorsulfonic acid or trifluoroacetic acid under the conditions mentioned. The reaction is preferably carried out in acetic acid under reflux.

Alternatively, the compounds of formula (III) can be prepared by reacting compounds of formula

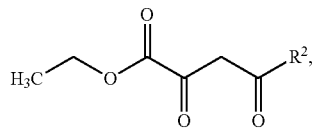
(VI)

in which R² has the meaning indicated above, with compounds of formula (V).

The reaction generally takes place in inert solvents, preferably in a temperature range from room temperature to the reflux of the solvent under atmospheric pressure, where appropriate in the presence of an acid.

Examples of inert solvents are alcohols such as methanol, ethanol, n-propanol, isopropanol, n-butanol, tert-butanol or 2-methoxyethanol, or other solvents such as N,N-dimethylformamide, N,N-dimethylacetamide or dimethyl sulfoxide.

If the reaction takes place in the presence of an acid, this can be added to the reaction solution from the outset or after a time of from 1 to 4 hours, whereby in the case of the later addition of the acid the reaction solution is heated where appropriate to a temperature up to the reflux of the solvent.

The acid is for example a concentrated mineral acid or a concentrated carboxylic acid such as, for example, concentrated hydrochloric acid, concentrated nitric acid, concentrated sulfuric acid or concentrated acetic acid.

The compounds of formulae (IV), (V) and (VI) are known or can be synthesized by known methods from the corresponding starting materials.

The preparation of the compounds of the invention can be illustrated by way of example by the following synthesis scheme.

They are therefore suitable for use as medicaments for the treatment and/or prophylaxis of diseases in humans and animals.

The compounds of the present invention are distinguished in particular by an advantageous range of antiretroviral effects.

The present invention further relates to the use of the compounds of the invention for the treatment and/or prophylaxis of diseases caused by retroviruses, especially HI viruses.

The present invention further relates to the use of the compounds of the invention for the treatment and/or prophylaxis of diseases, especially of the aforementioned diseases.

The present invention further relates to the use of the compounds of the invention for the manufacture of a medicament for the treatment and/or prophylaxis of diseases, especially of the aforementioned diseases.

The present invention further relates to a method for the treatment and/or prophylaxis of diseases, especially of the aforementioned diseases, using a therapeutically effective amount of the compounds of the invention.

Examples of areas of indication in human medicine which may be mentioned are:
1.) The treatment and prophylaxis of human retroviral infections.
2.) The treatment and prophylaxis of infections and diseases (AIDS) caused by HIV-1 (human immunodeficiency virus; formerly called HTLV III/LAV) and HIV-2 and the stages associated therewith, such as ARC (AIDS related complex) and LAS (lymphadenopathy syndrome), as well as the immunodeficiency and encephalopathy caused by this virus.
3.) The treatment of HIV infections caused by mono-, poly- or multiresistant HI viruses.

The expression resistant HI viruses means for example viruses with resistances to nucleosidic inhibitors (NRTI), Synthesis scheme:

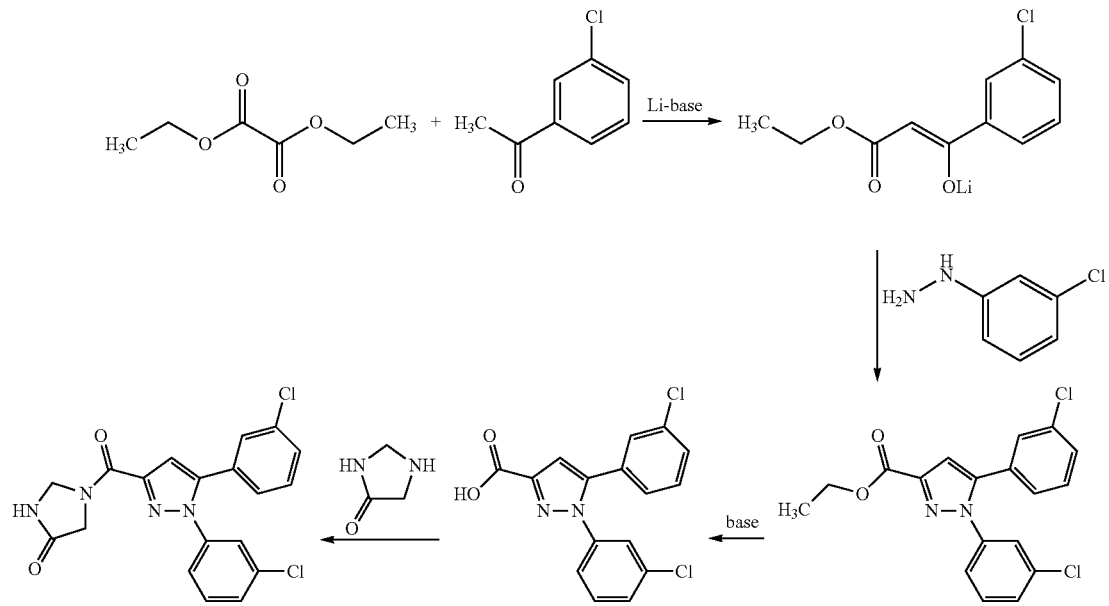

The compounds of the invention show a valuable range of pharmacological effects which could not have been predicted.

non-nucleosidic inhibitors (NNRTI) or protease inhibitors (PI) or viruses with resistances to other principles of action, e.g. T20 (fusion inhibitors).

4.) The treatment or prophylaxis of the AIDS-carrier state.
5.) The treatment or prophylaxis of an HTLV-I or HTLV-II infection.

Examples of indications in veterinary medicine which may be mentioned are:

Infections with
a) Maedi-visna (in sheep and goats)
b) progressive pneumonia virus (PPV) (in sheep and goats)
c) caprine arthritis encephalitis virus (in sheep and goats)
d) zwoegerziekte virus (in sheep)
e) infectious anaemia virus (of horses)
f) infections caused by the feline leukaemia virus
g) infections caused by the feline immunodeficiency virus (FIV)
h) infections caused by the simian immunodeficiency virus (SIV)

Preference is given from the area of indications in human medicine to items 2, 3 and 4 detailed above.

The substances are particularly suitable for controlling HI viruses showing resistances to known non-nucleosidic inhibitors of the reverse transcriptase, such as, for example, efavirenz or nevirapine.

The present invention further relates to medicaments comprising at least one compound of the invention and at least one or more further active ingredients, in particular for the treatment and/or prophylaxis of the aforementioned diseases.

The compounds of the invention can also, especially in items 2, 3 and 4 detailed above, advantageously be employed as components of a combination therapy with one or more other compounds which are active in these areas of application. These compounds can for example be employed in combination with effective doses of substances having antiviral activity based on the principles of action detailed below:

HIV protease inhibitors; examples which may be mentioned are: saquinavir, indinavir, ritonavir, nelfinavir, amprenavir, lopinavir, atazanavir, fosamprenavir, tipranavir, darunavir;

nucleosidic, nucleotidic and non-nucleosidic inhibitors of the HIV reverse transcriptase; examples which may be mentioned are: zidovudine, lamivudine, didanosine, zalcitabine, stavudine, lamivudine, abacavir, tenofovir, adefovir, emtricitabine, amdoxovir, apricitabine, racivir, nevirapine, delavirdine, efavirenz, etravirine, rilpivirine, UK-453,061;

HIV integrase inhibitors, examples which may be mentioned are: raltegravir, elvitegravir;

HIV fusion inhibitors; an example which may be mentioned is: enfuvirtide;

Inhibitors of the CXCR4/CCR5/gp120 interaction; examples which may be mentioned are: maraviroc, vicriviroc, INCB009471, AMD-070;

Inhibitors of the polyprotein maturation; an example which may be mentioned is: bevirimat.

This selection is intended to serve to illustrate the possible combinations but not to restrict to the examples detailed here. In principle, every combination of the compounds of the invention with substances having antiviral activity is to be considered as within the scope of the invention.

The compounds of the invention may act systemically and/or locally. They can for this purpose be administered in a suitable way, such as, for example, orally, parenterally, pulmonarily, nasally, sublingually, lingually, buccally, rectally, dermally, transdermally, conjunctivally, otically or as an implant or stent.

For these administration routes the compounds of the invention can be administered in suitable administration forms.

Suitable for oral administration are administration forms which function according to the prior art and deliver the compounds of the invention rapidly and/or in a modified manner, and which contain the compounds of the invention in crystalline and/or amorphized and/or dissolved form, such as, for example, tablets (uncoated or coated tablets, for example having coatings which are resistant to gastric juice or dissolve with a delay or are insoluble and control the release of the compound of the invention), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other administration a routes are, for example, pharmaceutical forms for inhalation (inter alia powder inhalers, nebulizers), nasal drops, solutions, sprays; tablets, films/wafers or capsules, for lingual, sublingual or buccal administration, suppositories, preparations for ears or eyes, vaginal capsules, aqueous suspensions (lotions, shaking mixtures), lipophilic suspensions, ointments, creams, transdermal therapeutic systems (such as for example patches), milk, pastes, foams, dusting powders, implants or stents.

The compounds of the invention can be converted into the stated administration forms. This can take place in a manner known per se by mixing with inert, non-toxic, pharmaceutically acceptable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention further relates to medicaments which comprise at least one compound of the invention, usually together with one or more inert, non-toxic, pharmaceutically acceptable excipients, as well as to their use for the aforementioned purposes.

It has generally proved to be advantageous both in human and in veterinary medicine to administer the active ingredient(s) of the invention in total amounts of from 0.1 to 200 mg/kg, preferably 1 to 100 mg/kg, of body weight every 24 hours, where appropriate in the form of a plurality of single doses, to achieve the desired result. A single dose preferably comprises the active ingredient(s) in amounts of from 1 to 80 mg/kg, in particular 1 to 30 mg/kg, of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. In the case of an administration of larger amounts, it may be advisable to distribute these in a plurality of single doses over the day.

The percentage data in the following tests and examples are, unless indicated otherwise, percentages by weight; parts are parts by weight. Solvent ratios, dilution ratios and concentration data of liquid/liquid solutions are based in each case on volume. The statement "w/v" means "weight/volume". Thus, for example, "10% w/v" means: 100 ml of solution or suspension contain 10 g of substance.

DETAILED DESCRIPTION OF PREFERRED EMBODIMENTS

A) EXAMPLES

Abbreviations
aq. aqueous, aqueous solution
conc. concentrated
DCI direct chemical ionization (in MS)
DMA N,N-dimethylacetamide
DMF N,N-dimethylformamide
DMSO dimethyl sulfoxide
EDC N'-(3-dimethylaminopropyl)-N-ethylcarbodiimide x HCl
eq. equivalent(s)
ESI electrospray ionization (in MS)
h hour(s)
HATU O-(7-azabenzotriazol-1-yl)-N,N,N',N'-tetramethyluronium hexafluorophosphate
HPLC high pressure, high performance liquid chromatography
LC-MS coupled liquid chromatography-mass spectrometry
min minute(s)
MS mass spectrometry
NMR nuclear magnetic resonance spectroscopy
PyBOP benzotriazol-1-yloxytris(pyrrolidino)phosphonium hexafluorophosphate
$R_t$ retention time (in HPLC)
RT room temperature
TBTU O-(benzotriazol-1-yl)-N,N,N',N'-tetramethyluronium tetrafluoroborate
TFA trifluoroacetic acid
THF tetrahydrofuran
TMOF trimethyl orthoformate
LC-MS/GC-MS Methods:
  Method 1:
    MS instrument type: Micromass ZQ; HPLC instrument type: HP 1100 Series; UV DAD; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.
  Method 2:
    Instrument: Micromass Quattro LCZ with HPLC Agilent Series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.
  Method 3:
    MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
  Method 4:
    Instrument: Micromass Quattro LCZ with HPLC Agilent Series 1100; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.
  Method 5:
    Instrument: Micromass QuattroPremier with Waters HPLC Acquity; column: Thermo Hypersil GOLD 1.9μ 50 mm×1 mm; eluent A: 1 l of water+0.5 ml of 50% formic acid, eluent B: 1 l of acetonitrile+0.5 ml of 50% formic acid; gradient: 0.0 min 90% A→0.1 min 90% A→1.5 min 10% A→2.2 min 10% A; oven: 50° C.; flow rate: 0.33 ml/min; UV detection: 210 nm.
  Method 6:
    MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.
  Method 7:
    MS instrument type: Micromass ZQ; HPLC instrument type: Waters Alliance 2795; column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.
  Method 8:
    Instrument: Micromass Quattro LCZ with HPLC Agilent Series 1100; column: Phenomenex Gemini 3μ 30 mm×3.00 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.
  Method 9:
    Instrument: Micromass Quattro LCZ with HPLC Agilent Series 1100; column: Phenomenex Synergi 2.5μ MAX-RP 100A Mercury 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.
  Method 10:
    MS instrument type: Waters (Micromass) Quattro Micro; HPLC instrument type: Agilent 1100 Series; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.
  Method 11:
    Instrument: Micromass GCT, GC6890; column: Restek RTX-35, 15 m×200 μm×0.33 μm; constant helium flow rate: 0.88 ml/min; oven: 70° C.; inlet: 250° C.; gradient: 70° C., 30° C./min→310° C. (hold for 3 min).

Method 12:

Instrument: Waters ACQUITY SQD HPLC system; column: Waters Acquity HPLC HSS T3 1.8μ 50×1 mm; eluent A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A; oven: 50° C.; flow rate: 0.40 ml/min; UV detection: 210-400 nm.

Starting Compounds and Intermediates

Example 1A

Lithium 1-(3-chloro-5-fluorophenyl)-4-ethoxy-3,4-dioxobut-1-en-1-olate

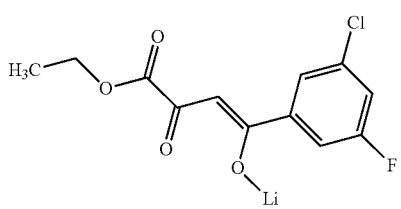

A solution of 78 ml (78 mmol) of lithium hexamethyldisilazide (1N solution in tetrahydrofuran) in 60 ml of diethyl ether is provided at −78° C. under argon and a solution of 12.5 g (72.4 mmol) of 1-(3-chloro-5-fluorophenyl)ethanone in 190 ml of diethyl ether is added. After 45 minutes at −78° C., 11.6 g (79.7 mmol) of diethyl oxalate are added dropwise, and the mixture is stirred at room temperature overnight. The reaction mixture is concentrated and 28.6 g of the title compound with 71% purity (100% of theory) are obtained, which are reacted without further purification.

$^1$H-NMR (400 MHz, DMSO-$d_6$): δ=7.63 (t, 1H), 7.55-7.50 (m, 2H), 6.33 (s, 1H), 4.14 (q, 2H), 1.24 (t, 3H).

LC-MS (Method 1): $R_t$=2.65 min; MS (ESIpos): m/z=273 [M−Li+2H]$^+$.

Example 2A

Lithium 1-(3,5-difluorophenyl)-4-ethoxy-3,4-dioxobut-1-en-1-olate

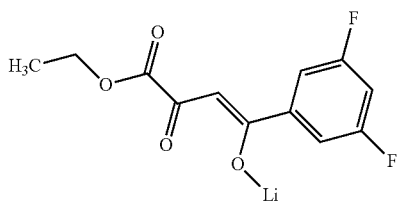

The preparation of the title compound takes place starting from 1-(3,5-difluorophenyl)ethanone and diethyl oxalate in analogy to the synthesis of the compound of Example 1A. 5.43 g (65% of theory) of the title compound are obtained.

$^1$H-NMR (400 MHz, DMSO-$d_6$): δ=7.45 (d, 2H), 7.35 (t, 1H), 6.38 (s, 1H), 4.17 (q, 2H), 1.26 (t, 3H).

LC-MS (Method 3): $R_t$=2.43 min; MS (ESIpos): m/z=257 [M−Li+2H]$^+$.

Example 3A

Lithium 1-(3-chlorophenyl)-4-ethoxy-3,4-dioxobut-1-en-1-olate

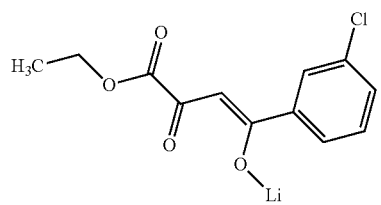

The preparation of the title compound takes place starting from 1-(3-chlorophenyl)ethanone and diethyl oxalate in analogy to the synthesis of the compound of Example 1A. 40.4 g (92% of theory) of the title compound are obtained.

LC-MS (Method 4): $R_t$=3.91 min; MS (ESIpos): m/z=255 [M−Li+2H]$^+$.

Example 4A

Lithium 1-(3-cyanophenyl)-4-ethoxy-3,4-dioxobut-1-en-1-olate

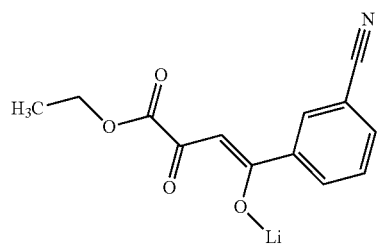

The preparation of the title compound takes place starting from 3-acetylbenzenecarbonitrile and diethyl oxalate in analogy to the synthesis of the compound of Example 1A. 0.53 g of the title compound with 62% purity (76% of theory) are obtained.

LC-MS (Method 5): $R_t$=1.11 min; MS (ESIpos): m/z=246 [M−Li+2H]$^+$.

Example 5A

Lithium 1-(3-chloro-4-fluorophenyl)-4-ethoxy-3,4-dioxobut-1-en-1-olate

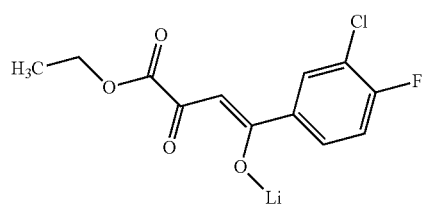

The preparation of the title compound takes place starting from 1-(3-chloro-4-fluorophenyl)ethanone and diethyl oxalate in analogy to the synthesis of the compound of Example 1A. 9.7 g of the title compound with 66% purity (79% of theory) are obtained.

LC-MS (Method 1): $R_t$=2.69 min; MS (ESIpos): m/z=273 [M−Li+2H]$^+$.

Example 6A

Lithium 4-ethoxy-3,4-dioxo-1-[3-(trifluoromethoxy)phenyl]but-1-en-1-olate

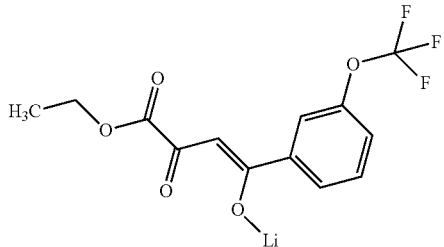

The preparation of the title compound takes place starting from 1-[3-(trifluoromethoxy)phenyl]ethanone and diethyl oxalate in analogy to the synthesis of the compound of Example 1A. 7.7 g of the title compound with 65% purity (80% of theory) are obtained.

$^1$H-NMR (400 MHz, DMSO-d$_6$): δ=7.84 (d, 1H), 7.70 (s, 1H), 7.56 (t, 1H), 7.45 (d, 1H), 6.41 (s, 1H), 4.15 (q, 2H), 1.25 (t, 3H).

LC-MS (Method 5): R$_t$=1.39 min; MS (ESIpos): m/z=305 [M-Li+2H]$^+$.

Example 7A

Lithium 4-ethoxy-1-[4-fluoro-3-(trifluoromethyl)phenyl]-3,4-dioxobut-1-en-1-olate

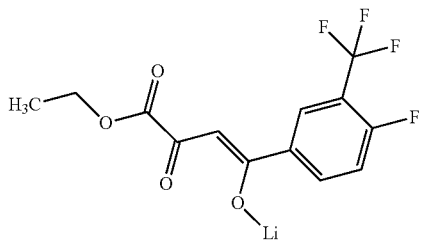

The preparation of the title compound takes place starting from 1-[4-fluoro-3-(trifluoromethyl)phenyl]ethanone and diethyl oxalate in analogy to the synthesis of the compound of Example 1A. 8.7 g of the title compound with 78% purity (90% of theory) are obtained.

$^1$H-NMR (400 MHz, DMSO-d$_6$): δ=7.91 (s, 1H), 7.89 (d, 1H), 7.79 (d, 1H), 6.40 (s, 1H), 4.16 (q, 2H), 1.25 (t, 3H).

LC-MS (Method 3): R$_t$=2.64 min; MS (ESIpos): m/z=307 [M-Li+2H]$^+$.

Example 8A

Lithium 4-ethoxy-1-(3-fluorophenyl)-3,4-dioxobut-1-en-1-olate

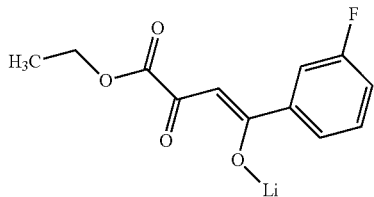

The preparation of the title compound takes place starting from 1-(3-fluorophenyl)ethanone and diethyl oxalate in analogy to the synthesis of the compound of Example 1A. 9.4 g (98% of theory) of the title compound are obtained.

LC-MS (Method 5): R$_t$=1.22 min; MS (ESIpos): m/z=239 [M-Li+2H]$^+$.

Example 9A

Lithium 4-ethoxy-3,4-dioxo-1-[3-(trifluoromethyl)phenyl]but-1-en-1-olate

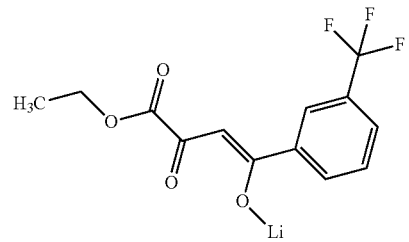

The preparation of the title compound takes place starting from 1-[3-(trifluoromethyl)phenyl]ethanone and diethyl oxalate in analogy to the synthesis of the compound of Example 1A. 44.2 g of the title compound with 62% purity (70% of theory) are obtained.

$^1$H-NMR (400 MHz, DMSO-d$_6$): δ=8.12 (d, 1H), 8.07 (s, 1H), 7.83 (d, 1H), 7.67 (t, 1H), 6.45 (s, 1H), 4.16 (q, 2H), 1.25 (t, 3H).

LC-MS (Method 3): R$_t$=2.54 min; MS (ESIpos): m/z=289 [M-Li+2H]$^+$.

Example 10A

Lithium 4-ethoxy-1-(3-methoxyphenyl)-3,4-dioxobut-1-en-1-olate

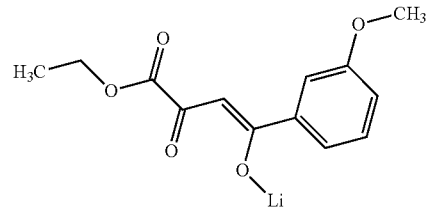

The preparation of the title compound takes place starting from 1-(3-methoxyphenyl)ethanone and diethyl oxalate in analogy to the synthesis of the compound of Example 1A. 0.62 g of the title compound with 64% purity (93% of theory) are obtained.

LC-MS (Method 5): R$_t$=1.22 min; MS (ESIpos): m/z=251 [M-Li+2H]$^+$.

Example 11A

Lithium 1-(3,4-difluorophenyl)-4-ethoxy-3,4-dioxobut-1-en-1-olate

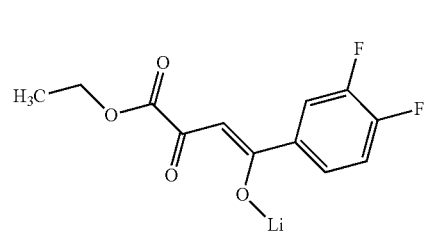

The preparation of the title compound takes place starting from 1-(3,4-difluorophenyl)ethanone and diethyl oxalate in analogy to the synthesis of the compound of Example 1A. 8.47 g (100% of theory) of the title compound are obtained.

$^1$H-NMR (400 MHz, DMSO-d$_6$): δ=7.79 (ddd, 1H), 7.74-7.68 (m, 1H), 7.47 (q, 1H), 6.40 (s, 1H), 4.16 (q, 2H), 1.26 (t, 3H).

LC-MS (Method 3): R$_t$=2.40 min; MS (ESIpos): m/z=257 [M-Li+2H]$^+$.

Example 12A

Lithium 1-(3-bromo-4-fluorophenyl)-4-ethoxy-3,4-dioxobut-1-en-1-olate

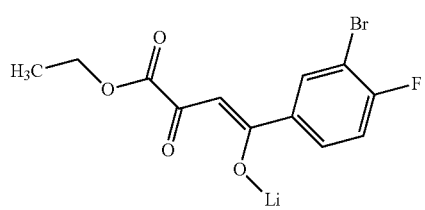

The preparation of the title compound takes place starting from 1-(3-bromo-4-fluorophenyl)ethanone and diethyl oxalate in analogy to the synthesis of the compound of Example 1A. 7.8 g of the title compound with 75% purity (79% of theory) are obtained.

$^1$H-NMR (400 MHz, DMSO-d$_6$): δ=8.05 (dd, 1H), 7.86 (ddd, 1H), 7.40 (t, 1H), 6.36 (s, 1H), 4.15 (q, 2H), 1.25 (t, 3H).

LC-MS (Method 3): R$_t$=2.59 min; MS (ESIpos): m/z=318 [M-Li+2H]$^+$.

Example 13A

Lithium 4-ethoxy-1-(2-fluorophenyl)-3,4-dioxobut-1-en-1-olate

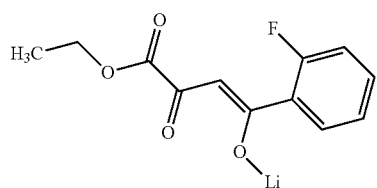

The preparation of the title compound takes place starting from 1-(2-fluorophenyl)ethanone and diethyl oxalate in analogy to the synthesis of the compound of Example 1A. 4.5 g (82% of theory) of the title compound are obtained.

$^1$H-NMR (400 MHz, DMSO-d$_6$): δ=7.67 (dt, 1H), 7.49-7.42 (m, 1H), 7.27-7.17 (m, 2H), 6.24 (s, 1H), 4.14 (q, 2H), 1.24 (t, 3H).

LC-MS (Method 3): R$_t$=2.36 min; MS (ESIpos): m/z=239 [M-Li+2H]$^+$.

Example 14A

Lithium 1-(2,3-difluorophenyl)-4-ethoxy-3,4-dioxobut-1-en-1-olate

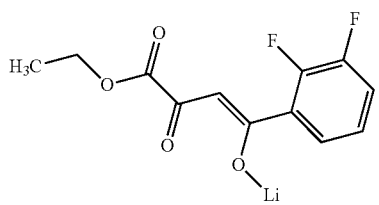

The preparation of the title compound takes place starting from 1-(2,3-difluorophenyl)ethanone and diethyl oxalate in analogy to the synthesis of the compound of Example 1A. 1.7 g of the title compound with 26% purity (48% of theory) are obtained.

LC-MS (Method 3): R$_t$=2.33 min; MS (ESIpos): m/z=257 [M-Li+21-1]$^+$.

Example 15A

Lithium 4-ethoxy-1-(3-fluoro-5-methoxyphenyl)-3,4-dioxobut-1-en-1-olate

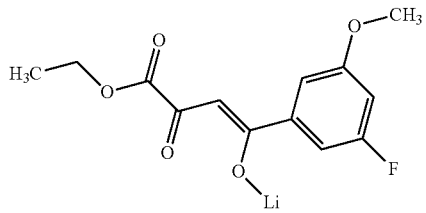

5.00 g (29.4 mmol) of 3-fluoro-5-methoxybenzoic acid are provided in 51 ml of toluene, 6.4 ml (88.2 mmol) of thionyl chloride are added, and the mixture is heated under reflux for 2 h. The reaction mixture is subsequently concentrated, the residue is taken up in dichloromethane, 3.73 g (38.2 mmol) of N,O-dimethylhydroxylamine hydrochloride and, at 0° C., 10.7 ml (76.4 mmol) of triethylamine are added, and the mixture is stirred at room temperature overnight. Water is added, the phases are separated, extraction is carried out with dichloromethane, and the combined organic phases are dried over sodium sulfate, filtered and concentrated. The residue is dissolved in 105 ml of diethyl ether and added to 9.6 ml (28.6 mmol) of a 3M solution of methylmagnesium bromide in diethyl ether under argon at room temperature, and the mixture is heated under reflux for 2 h. A saturated aqueous ammonium chloride solution is subsequently added, extraction is carried out with dichloromethane, and the combined organic phases are dried over sodium sulfate, filtered and concentrated. The crude product 1-(3-fluoro-5-methoxyphenyl)ethanone is reacted with diethyl oxalate in analogy to the synthesis of the compound of Example 1A. 4.02 g of the title compound with 61% purity (30% of theory) are obtained.

LC-MS (Method 5): R$_t$=1.26 min; MS (ESIpos): m/z=269 [M-Li+2H]$^+$.

Example 16A

Lithium 1-[3-(benzyloxy)phenyl]-4-ethoxy-3,4-dioxobut-1-en-1-olate

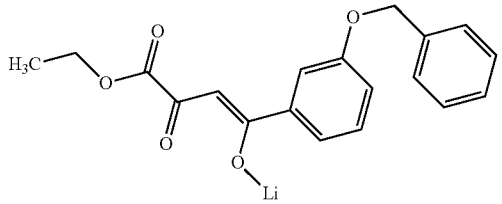

The preparation of the title compound takes place starting from 1-[3-(benzyloxy)phenyl]ethanone and diethyl oxalate in analogy to the synthesis of the compound of Example 1A. 8.1 g of the title compound with 74% purity (82% of theory) are obtained.

$^1$H-NMR (400 MHz, DMSO-$d_6$): δ=7.49-7.44 (m, 2H), 7.43-7.36 (m, 4H), 7.36-7.30 (m, 2H), 7.14-7.08 (m, 1H), 6.39 (s, 1H), 5.15 (s, 2H), 4.14 (q, 2H), 1.25 (t, 3H).

LC-MS (Method 2): $R_t$=2.96 min; MS (ESIpos): m/z=327 [M-Li+2H]$^+$.

Example 17A

Lithium 4-ethoxy-1-(3-fluoro-5-trifluoromethylphenyl)-3,4-dioxobut-1-en-1-olate

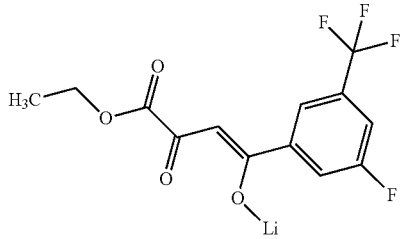

The preparation of the title compound takes place starting from 1-[3-fluoro-5-(trifluoromethyl)phenyl]ethanone and diethyl oxalate in analogy to the synthesis of the compound of Example 1A. 1.5 g of the title compound with 62% purity (62% of theory) are obtained.

LC-MS (Method 5): $R_t$=1.37 min; MS (ESIpos): m/z=307 [M-Li+2H]$^+$.

Example 18A

Lithium 1-(3-bromo-5-fluorophenyl)-4-ethoxy-3,4-dioxobut-1-en-1-olate

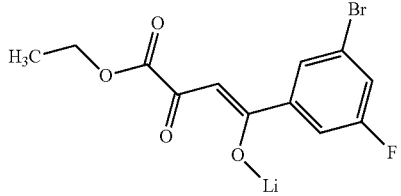

The preparation of the title compound takes place starting from 1-(3-bromo-5-fluorophenyl)ethanone (described in US2003/229096A1) and diethyl oxalate in analogy to the synthesis of the compound of Example 1A. 4.7 g of the title compound with 62% purity (74% of theory) are obtained.

LC-MS (Method 7): $R_t$=2.29 min; MS (ESIpos): m/z=317 [M-Li+2H]$^+$.

Example 19A

Lithium 1-[3,5-bis(trifluoromethyl)phenyl]-4-ethoxy-3,4-dioxobut-1-en-1-olate

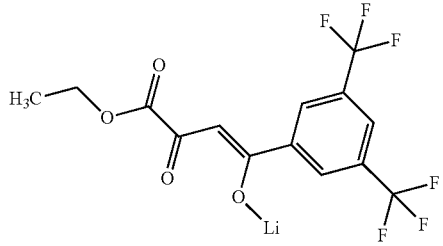

The preparation of the title compound takes place starting from 1-[3,5-bis(trifluoromethyl)phenyl]ethanone and diethyl oxalate in analogy to the synthesis of the compound of Example 1A. 6.1 g (86% of theory) of the title compound are obtained.

$^1$H-NMR (400 MHz, DMSO-$d_6$): δ=8.36 (s, 2H), 8.23 (s, 1H), 6.48 (s, 1H), 4.18 (q, 2H), 1.27 (t, 3H).

LC-MS (Method 3): $R_t$=2.88 min; MS (ESIneg): m/z=355 [M-Li]$^-$.

Example 20A

Lithium 4-ethoxy-1-(3-fluoro-5-methylphenyl)-3,4-dioxobut-1-en-1-olate

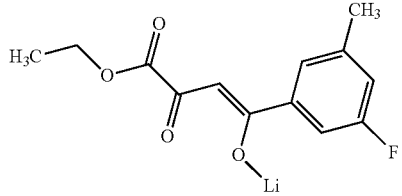

The preparation of the title compound takes place starting from 1-(3-fluoro-5-methylphenyl)ethanone and diethyl oxalate in analogy to the synthesis of the compound of Example 1A. 8.88 g of the title compound with 66% purity (70% of theory) are obtained.

LC-MS (Method 1): $R_t$=2.67 min; MS (ESIpos): m/z=253 [M-Li+2H]$^+$.

Example 21A

Ethyl 1-(3-chloro-4-fluorophenyl)-5-(3-chloro-5-fluorophenyl)-1H-pyrazole-3-carboxylate

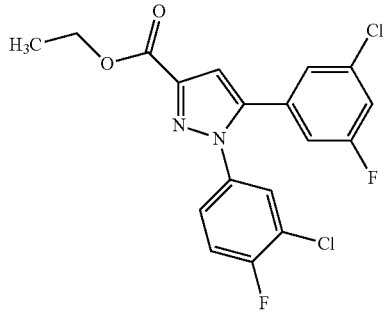 [SMILES: CCOC(=O)c1cc(-c2cc(F)cc(Cl)c2)n(-c2ccc(F)c(Cl)c2)n1]

28.6 g of the compound of Example 1A with 71% purity (72.9 mmol) are provided in 350 ml of ethanol, 15.8 g (80.2 mmol) of 3-chloro-4-fluorophenylhydrazine hydrochloride are added, and the mixture is stirred at room temperature overnight. The reaction mixture is concentrated and the residue is taken up in 350 ml of concentrated acetic acid and heated under reflux for 2 h. The reaction mixture is added to ethyl acetate and washed with water and a saturated aqueous sodium bicarbonate solution. The organic phase is concentrated and purified by flash chromatography (mobile phase: cyclohexane/ethyl acetate 20:1). 22.6 g (76% of theory) of the title compound are obtained.

$^1$H-NMR (400 MHz, DMSO-$d_6$): δ=7.80 (dd, 1H), 7.58-7.50 (m, 2H), 7.38 (ddd, 1H), 7.31 (s, 1H), 7.27 (s, 1H), 7.19 (dt, 1H), 4.34 (q, 2H), 1.32 (t, 3H).

LC-MS (Method 5): $R_t$=1.52 min; MS (ESIpos): m/z=397 [M+H]$^+$.

Example 22A

Ethyl 5-(3-chloro-5-fluorophenyl)-1-(3-chlorophenyl)-1H-pyrazole-3-carboxylate

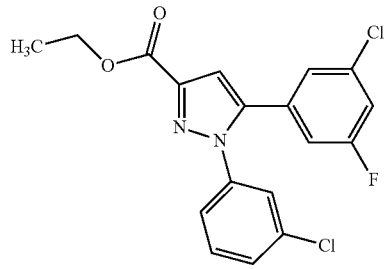 [SMILES: CCOC(=O)c1cc(-c2cc(F)cc(Cl)c2)n(-c2cccc(Cl)c2)n1]

The preparation of the title compound takes place starting from the compound of Example 1A and 3-chlorophenylhydrazine hydrochloride in analogy to the synthesis of the compound of Example 21A. 5.82 g of the title compound are obtained.

$^1$H-NMR (400 MHz, DMSO-$d_6$): δ=7.61-7.56 (m, 2H), 7.54-7.47 (m, 2H), 7.32 (s, 1H), 7.30 (d, 1H), 7.25 (d, 1H), 7.18 (dt, 1H), 4.35 (q, 2H), 1.32 (t, 3H).

LC-MS (Method 5): $R_t$=1.51 min; MS (ESIpos): m/z=379 [M+H]$^+$.

Example 23A

Ethyl 1-(3-chlorophenyl)-5-(3,5-difluorophenyl)-1H-pyrazole-3-carboxylate

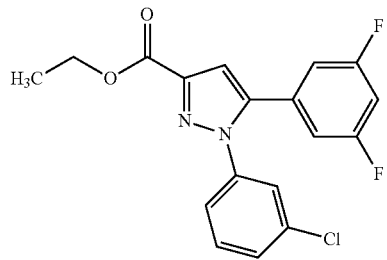 [SMILES: CCOC(=O)c1cc(-c2cc(F)cc(F)c2)n(-c2cccc(Cl)c2)n1]

The preparation of the title compound takes place starting from the compound of Example 2A and 3-chlorophenylhydrazine hydrochloride in analogy to the synthesis of the compound of Example 21A. After purification by flash chromatography (mobile phase: cyclohexane/ethyl acetate 3:1) 2.58 g (68% of theory) of the title compound are obtained.

$^1$H-NMR (400 MHz, DMSO-$d_6$): δ=7.60-7.56 (m, 2H), 7.53-7.47 (m, 1H), 7.37-7.27 (m, 3H), 7.10-7.03 (m, 2H), 4.35 (q, 2H), 1.32 (t, 3H).

LC-MS (Method 3): $R_t$=2.74 min; MS (ESIpos): m/z=363 [M+H]$^+$.

Example 24A

Ethyl 1,5-bis(3-chlorophenyl)-1H-pyrazole-3-carboxylate

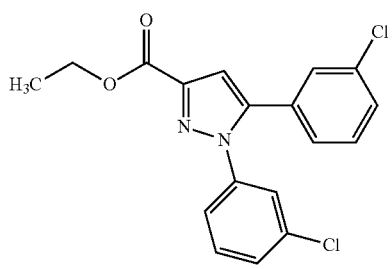 [SMILES: CCOC(=O)c1cc(-c2cccc(Cl)c2)n(-c2cccc(Cl)c2)n1]

112 g (413 mmol) of the compound of Example 3A are provided in 1120 ml of ethanol, 101 g (561 mmol) of 3-chlorophenylhydrazine hydrochloride are added, and the mixture is stirred at room temperature overnight. The reaction mixture is concentrated and the residue is taken up in 1120 ml of concentrated acetic acid and heated under reflux for 2 h. The mixture is left to stand at room temperature overnight, the resulting precipitate is collected by suction filtration and stirred with cyclohexane, and the precipitate is collected by suction filtration, washed with cyclohexane and dried under high vacuum. 126 g (80% of theory) of the title compound are obtained.

$^1$H-NMR (400 MHz, DMSO-$d_6$): δ=7.58-7.54 (m, 2H), 7.51-7.43 (m, 3H), 7.40 (t, 1H), 7.30-7.26 (m, 1H), 7.25 (s, 1H), 7.19 (d, 1H), 4.34 (q, 2H), 1.32 (t, 3H).

LC-MS (Method 2): $R_t$=3.00 min; MS (ESIpos): m/z=361 [M+H]$^+$.

Example 25A

Ethyl 1,5-bis(3-chloro-4-fluorophenyl)-1H-pyrazole-3-carboxylate

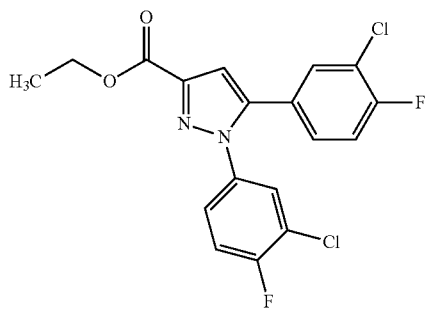 [SMILES: CCOC(=O)c1cc(-c2ccc(F)c(Cl)c2)n(-c2ccc(F)c(Cl)c2)n1]

The preparation of the title compound takes place starting from the compound of Example 5A in analogy to the synthesis of the compound of Example 21A. 5.78 g of the title compound are obtained.

$^1$H-NMR (400 MHz, DMSO-$d_6$): δ=7.78 (dd, 1H), 7.67 (dd, 1H), 7.53 (t, 1H), 7.44 (t, 1H), 7.35 (ddd, 1H), 7.25 (s, 1H), 7.22 (ddd, 1H), 4.34 (q, 2H), 1.32 (t, 3H).

Example 26A

Ethyl 1-(3-chlorophenyl)-5-[3-(trifluoromethoxy)phenyl]-1H-pyrazole-3-carboxylate

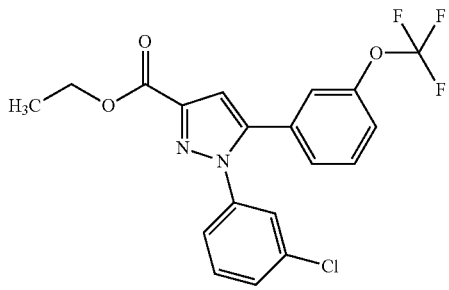 [SMILES: CCOC(=O)c1cc(-c2cccc(OC(F)(F)F)c2)n(-c2cccc(Cl)c2)n1]

The preparation of the title compound takes place starting from the compound of Example 6A and 3-chlorophenylhydrazine hydrochloride in analogy to the synthesis of the compound of Example 21A. 4.56 g (95% of theory) of the title compound are obtained.

$^1$H-NMR (400 MHz, DMSO-$d_6$): δ=7.59-7.46 (m, 4H), 7.46-7.38 (m, 2H), 7.32-7.27 (m, 2H), 7.22-7.19 (m, 1H), 4.35 (q, 2H), 1.32 (t, 3H).

LC-MS (Method 3): $R_t$=2.92 min; MS (ESIpos): m/z=411 [M+H]$^+$.

Example 27A

Ethyl 1-(3-chlorophenyl)-5-[4-fluoro-3-(trifluoromethyl)phenyl]-1H-pyrazole-3-carboxylate

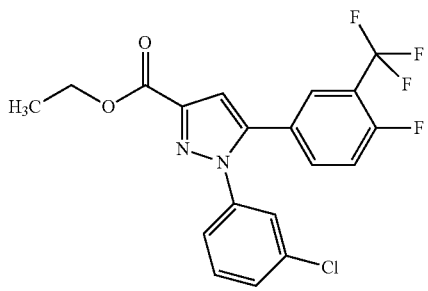 [SMILES: CCOC(=O)c1cc(-c2ccc(F)c(C(F)(F)F)c2)n(-c2cccc(Cl)c2)n1]

The preparation of the title compound takes place starting from the compound of Example 7A and 3-chlorophenylhydrazine hydrochloride in analogy to the synthesis of the compound of Example 21A. 3.60 g of the title compound are obtained.

$^1$H-NMR (400 MHz, DMSO-$d_6$): δ=7.76 (d, 1H), 7.61-7.56 (m, 3H), 7.50 (t, 1H), 7.43 (s, 1H), 7.42 (s, 1H), 7.34-7.30 (m, 1H), 4.35 (q, 2H), 1.33 (t, 3H).

LC-MS (Method 5): $R_t$=1.51 min; MS (ESIpos): m/z=397 [M+H]$^+$.

Example 28A

Ethyl 1-(3-chloro-4-fluorophenyl)-5-[3-(trifluoromethoxy)phenyl]-1H-pyrazole-3-carboxylate

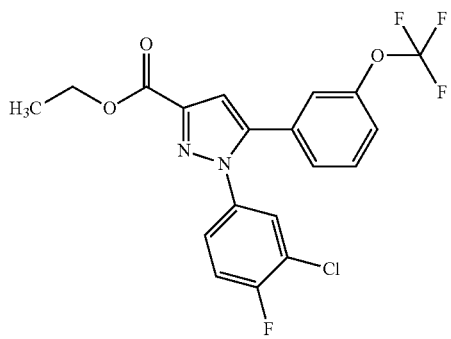 [SMILES: CCOC(=O)c1cc(-c2cccc(OC(F)(F)F)c2)n(-c2ccc(F)c(Cl)c2)n1]

The preparation of the title compound takes place starting from the compound of Example 6A in analogy to the synthesis of the compound of Example 21A. 3.50 g (66% of theory) of the title compound are obtained.

$^1$H-NMR (400 MHz, DMSO-$d_6$): δ=7.74 (dd, 1H), 7.59-7.51 (m, 2H), 7.44-7.35 (m, 3H), 7.28 (s, 1H), 7.21 (s, 1H), 4.35 (q, 2H), 1.32 (t, 3H).

LC-MS (Method 1): $R_t$=3.04 min; MS (ESIpos): m/z=429 [M+H]$^+$.

Example 29A

Ethyl 5-(3-chloro-4-fluorophenyl)-1-(3-chlorophenyl)-1H-pyrazole-3-carboxylate

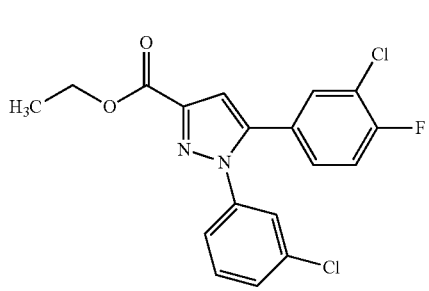

The preparation of the title compound takes place starting from the compound of Example 5A and 3-chlorophenylhydrazine hydrochloride in analogy to the synthesis of the compound of Example 21A. 5.67 g of the title compound are obtained.

$^1$H-NMR (400 MHz, DMSO-$d_6$): δ=7.64 (dd, 1H), 7.58-7.54 (m, 2H), 7.51-7.42 (m, 2H), 7.29-7.21 (m, 3H), 4.34 (q, 2H), 1.32 (t, 3H).

LC-MS (Method 5): R$_t$=1.50 min; MS (ESIpos): m/z=379 [M+H]$^+$.

Example 30A

Ethyl 5-(3-fluorophenyl)-1-(3-methoxyphenyl)-1H-pyrazole-3-carboxylate

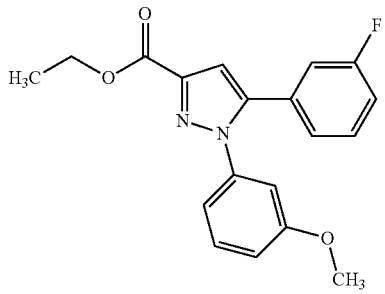 [SMILES: CCOC(=O)c1cc(-c2cccc(F)c2)n(-c2cccc(OC)c2)n1]

The preparation of the title compound takes place starting from the compound of Example 8A and 3-methoxyphenylhydrazine hydrochloride in analogy to the synthesis of the compound of Example 21A. 30.4 g (62% of theory) of the title compound are obtained.

$^1$H-NMR (400 MHz, DMSO-d$_6$): δ=7.44-7.33 (m, 2H), 7.24 (dd, 1H), 7.21 (s, 1H), 7.17 (dt, 1H), 7.08 (d, 1H), 7.04 (dd, 1H), 6.95 (t, 1H), 6.86 (dd, 1H), 4.34 (q, 2H), 3.73 (s, 3H), 1.32 (t, 3H).

LC-MS (Method 1): R$_t$=2.78 min; MS (ESIpos): m/z=341 [M+H]$^+$.

Example 31A

Ethyl 1-(3-chlorophenyl)-5-(3-methoxyphenyl)-1H-pyrazole-3-carboxylate

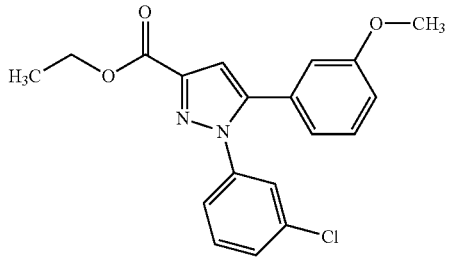 [SMILES: CCOC(=O)c1cc(-c2cccc(OC)c2)n(-c2cccc(Cl)c2)n1]

The preparation of the title compound takes place starting from the compound of Example 10A and 3-chlorophenylhydrazine hydrochloride with purification by preparative HPLC (RP18 column; mobile phase: acetonitrile/water gradient) in analogy to the synthesis of the compound of Example 21A. 1.60 g of the title compound are obtained.

$^1$H-NMR (400 MHz, DMSO-d$_6$): δ=7.57-7.51 (m, 2H), 7.47 (t, 1H), 7.31-7.25 (m, 2H), 7.17 (s, 1H), 6.96 (dd, 1H), 6.89 (s, 1H), 6.80 (d, 1H), 4.34 (q, 2H), 3.69 (s, 3H), 1.32 (t, 3H).

LC-MS (Method 3): R$_t$=2.68 min; MS (ESIpos): m/z=357 [M+H]$^+$.

Example 32A

Ethyl 5-(3-chlorophenyl)-1-[3-(trifluoromethyl)phenyl]-1H-pyrazole-3-carboxylate

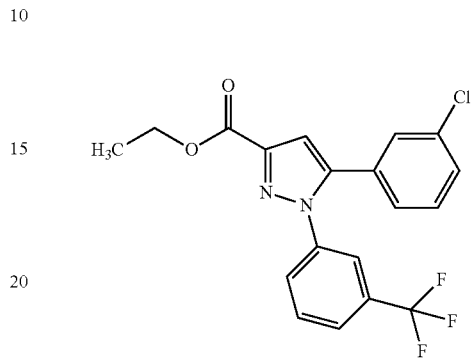

The preparation of the title compound takes place starting from the compound of Example 3A and 3-(trifluoromethyl)phenylhydrazine hydrochloride with purification by preparative HPLC (RP18 column; mobile phase: acetonitrile/water gradient) in analogy to the synthesis of the compound of Example 21A. 2.00 g (42% of theory) of the title compound are obtained.

$^1$H-NMR (400 MHz, DMSO-d$_6$): δ=7.85 (d, 1H), 7.75 (s, 1H), 7.71 (t, 1H), 7.64 (d, 1H), 7.50-7.43 (m, 2H), 7.40 (t, 1H), 7.27 (s, 1H), 7.20 (d, 1H), 4.35 (q, 2H), 1.33 (t, 3H).

LC-MS (Method 1): R$_t$=3.09 min; MS (ESIpos): m/z=395 [M+H]$^+$.

Example 33A

Ethyl 1-(3-chlorophenyl)-5-(3,4-difluorophenyl)-1H-pyrazole-3-carboxylate

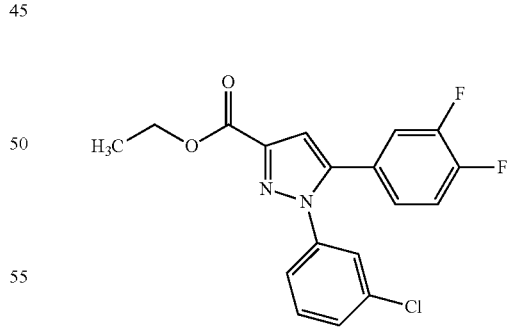

The preparation of the title compound takes place starting from the compound of Example 11A and 3-chlorophenylhydrazine hydrochloride in analogy to the synthesis of the compound of Example 21A. 2.83 g (49% of theory) of the title compound are obtained.

$^1$H-NMR (400 MHz, DMSO-d$_6$): δ=7.58-7.43 (m, 5H), 7.28-7.24 (m, 1H), 7.22 (s, 1H), 7.11-7.06 (m, 1H), 4.34 (q, 2H), 1.32 (t, 3H).

Example 34A

Ethyl 5-(3-bromo-4-fluorophenyl)-1-(3-chlorophenyl)-1H-pyrazole-3-carboxylate

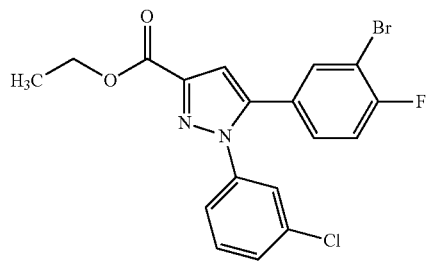

The preparation of the title compound takes place starting from the compound of Example 12A and 3-chlorophenylhydrazine hydrochloride in analogy to the synthesis of the compound of Example 21A. 3.68 g of the title compound are obtained.

$^1$H-NMR (400 MHz, DMSO-d$_6$): δ=7.74 (dd, 1H), 7.58-7.54 (m, 2H), 7.48 (t, 1H), 7.41 (t, 1H), 7.30-7.23 (m, 3H), 4.34 (q, 2H), 1.32 (t, 3H).

LC-MS (Method 1): R$_t$=3.03 min; MS (ESIpos): m/z=423 [M+H]$^+$.

Example 35A

Ethyl 5-(3-chlorophenyl)-1-(4-fluorophenyl)-1H-pyrazole-3-carboxylate

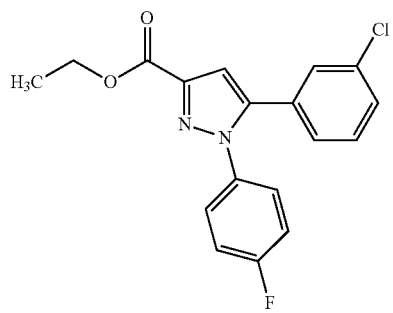 [SMILES: CCOC(=O)c1cc(-c2cccc(Cl)c2)n(-c2ccc(F)cc2)n1]

45.0 g (155 mmol) of the compound of Example 3A are provided in 400 ml of ethanol, 34.4 g (211 mmol) of 4-fluorophenylhydrazine hydrochloride are added, and the mixture is stirred at room temperature overnight. The reaction mixture is concentrated and the residue is taken up in 400 ml of concentrated acetic acid and heated under reflux for 2 hours. The reaction mixture is concentrated, and the residue is taken up in dichloromethane, washed with a saturated aqueous sodium bicarbonate solution and water, dried over sodium sulfate and concentrated. The residue is stirred in diethyl ether under reflux, and the precipitate is collected by suction filtration. The mother liquor is concentrated, the residue is stirred with cyclohexane, and the precipitate is collected by suction filtration. In total, 23 g (43% of theory) of the title compound are obtained.

$^1$H-NMR (400 MHz, DMSO-d$_6$): δ=7.47-7.39 (m, 4H), 7.39-7.30 (m, 3H), 7.23 (s, 1H), 7.16 (dt, 1H), 4.34 (q, 2H), 1.32 (t, 3H).

LC-MS (Method 1): R$_t$=2.89 min; MS (ESIpos): m/z=345 [M+H]$^+$.

Example 36A

Ethyl 1-(3-chlorophenyl)-5-(2-fluorophenyl)-1H-pyrazole-3-carboxylate

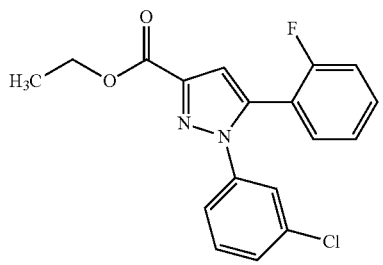 [SMILES: CCOC(=O)c1cc(-c2ccccc2F)n(-c2cccc(Cl)c2)n1]

The preparation of the title compound takes place starting from the compound of Example 13A and 3-chlorophenylhydrazine hydrochloride in analogy to the synthesis of the compound of Example 21A. 2.34 g (73% of theory) of the title compound are obtained.

$^1$H-NMR (400 MHz, DMSO-d$_6$): δ=7.56-7.41 (m, 5H), 7.33-7.21 (m, 3H), 7.16 (s, 1H), 4.35 (q, 2H), 1.33 (t, 3H).

LC-MS (Method 1): R$_t$=2.85 min; MS (ESIpos): m/z=345 [M+H]$^+$.

Example 37A

Ethyl 1-(4-fluorophenyl)-5-[3-(trifluoromethyl)phenyl]-1H-pyrazole-3-carboxylate

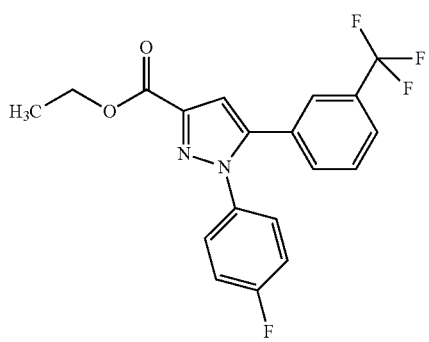 [SMILES: CCOC(=O)c1cc(-c2cccc(C(F)(F)F)c2)n(-c2ccc(F)cc2)n1]

The preparation of the title compound takes place starting from the compound of Example 9A and 4-fluorophenylhydrazine hydrochloride in analogy to the synthesis of the compound of Example 21A. 4.63 g (99% of theory) of the title compound are obtained.

$^1$H-NMR (400 MHz, DMSO-d$_6$): δ=7.74 (d, 1H), 7.64-7.54 (m, 3H), 7.47-7.41 (m, 2H), 7.37-7.30 (m, 3H), 4.34 (q, 2H), 1.32 (t, 3H).

LC-MS (Method 4): R$_t$=4.10 min; MS (ESIpos): m/z=379 [M+H]$^+$.

Example 38A

Ethyl 1-(3-chlorophenyl)-5-(2,3-difluorophenyl)-1H-pyrazole-3-carboxylate

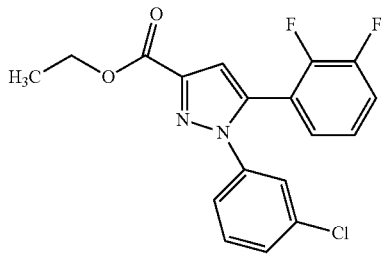 [SMILES: CCOC(=O)c1cc(-c2cccc(F)c2F)n(-c2cccc(Cl)c2)n1]

The preparation of the title compound takes place starting from the compound of Example 14A and 3-chlorophenylhydrazine hydrochloride in analogy to the synthesis of the compound of Example 21A. 240 mg (37% of theory) of the title compound are obtained.

$^1$H-NMR (400 MHz, CDCl$_3$): δ=7.46 (t, 1H), 7.36-7.31 (m, 1H), 7.28-7.18 (m, 2H), 7.14-7.06 (m, 3H), 7.00-6.94 (m, 1H), 4.47 (q, 2H), 1.43 (t, 3H).

LC-MS (Method 1): R$_t$=2.91 min; MS (ESIpos): m/z=363 [M+H]$^+$.

Example 39A

Ethyl 5-(3-chlorophenyl)-1-(4-chlorophenyl)-1H-pyrazole-3-carboxylate

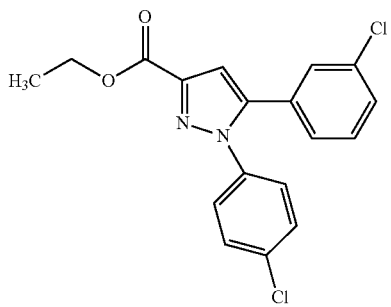 [SMILES: CCOC(=O)c1cc(-c2cccc(Cl)c2)n(-c2ccc(Cl)cc2)n1]

The preparation of the title compound takes place starting from the compound of Example 3A and 4-chlorophenylhydrazine hydrochloride in analogy to the synthesis of the compound of Example 21A. After additional purification by stirring in methanol, collection of the precipitate by suction filtration and drying under high vacuum 26.8 g (57% of theory) of the title compound are obtained.

$^1$H-NMR (400 MHz, DMSO-d$_6$): δ=7.58-7.53 (m, 2H), 7.49-7.43 (m, 2H), 7.42-7.36 (m, 3H), 7.24 (s, 1H), 7.19-7.14 (m, 1H), 4.34 (q, 2H), 1.32 (t, 3H).

LC-MS (Method 1): R$_t$=3.07 min; MS (ESIpos): m/z=361 [M+H]$^+$.

Example 40A

Ethyl 5-(3-fluorophenyl)-1-(4-fluorophenyl)-1H-pyrazole-3-carboxylate

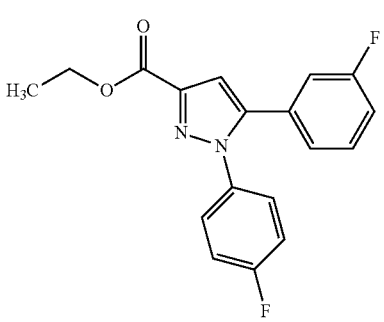 [SMILES: CCOC(=O)c1cc(-c2cccc(F)c2)n(-c2ccc(F)cc2)n1]

The preparation of the title compound takes place starting from the compound of Example 8A and 4-fluorophenylhydrazine hydrochloride in analogy to the synthesis of the compound of Example 21A. 23.0 g (44% of theory) of the title compound are obtained.

$^1$H-NMR (400 MHz, DMSO-d$_6$): δ=7.46-7.37 (m, 3H), 7.37-7.29 (m, 2H), 7.26-7.16 (m, 3H), 7.05 (d, 1H), 4.34 (q, 2H), 1.32 (t, 3H).

LC-MS (Method 1): R$_t$=2.76 min; MS (ESIpos): m/z=329 [M+H]$^+$.

Example 41A

Ethyl 1-(3-chlorophenyl)-5-(3-fluoro-5-methoxyphenyl)-1H-pyrazole-3-carboxylate

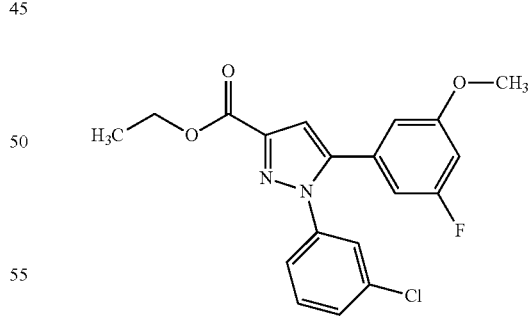

The preparation of the title compound takes place starting from the compound of Example 15A and 3-chlorophenylhydrazine hydrochloride in analogy to the synthesis of the compound of Example 21A. 2.20 g of the title compound with 68% purity are obtained.

$^1$H-NMR (400 MHz, DMSO-d$_6$): δ=7.59-7.55 (m, 2H), 7.50 (t, 1H), 7.31-7.27 (m, 1H), 7.24 (s, 1H), 6.89 (dt, 1H), 6.74-6.69 (m, 2H), 4.34 (q, 2H), 3.70 (s, 3H), 1.32 (t, 3H).

LC-MS (Method 1): $R_t$=2.80 min; MS (ESIpos): m/z=375 [M+H]$^+$.

Example 42A

Ethyl 1-(3-chloro-4-fluorophenyl)-5-(3-fluoro-5-methoxyphenyl)-1H-pyrazole-3-carboxylate

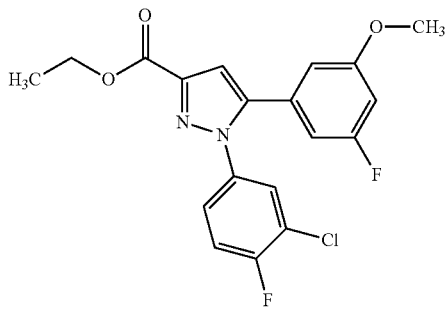 [SMILES: CCOC(=O)c1cc(-c2cc(F)cc(OC)c2)n(-c2ccc(F)c(Cl)c2)n1]

The preparation of the title compound takes place starting from the compound of Example 15A and 3-chloro-4-fluorophenylhydrazine hydrochloride in analogy to the synthesis of the compound of Example 21A. 2.36 g of the title compound with 82% purity are obtained.

$^1$H-NMR (400 MHz, DMSO-d$_6$): δ=7.77 (dd, 1H), 7.54 (t, 1H), 7.36 (ddd, 1H), 7.24 (s, 1H), 6.89 (dt, 1H), 6.75-6.70 (m, 2H), 4.34 (q, 2H), 3.71 (s, 3H), 1.32 (t, 3H).

LC-MS (Method 1): $R_t$=2.82 min; MS (ESIpos): m/z=393 [M+H]$^+$.

Example 43A

Ethyl 5-[3-(benzyloxy)phenyl]-1-(3-chlorophenyl)-1H-pyrazole-3-carboxylate

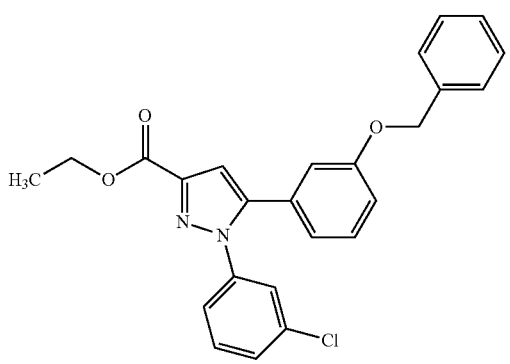 [SMILES: CCOC(=O)c1cc(-c2cccc(OCc3ccccc3)c2)n(-c2cccc(Cl)c2)n1]

The preparation of the title compound takes place starting from the compound of Example 16A and 3-chlorophenylhydrazine hydrochloride in analogy to the synthesis of the compound of Example 21A. 14.1 g of the title compound are obtained.

$^1$H-NMR (400 MHz, DMSO-d$_6$): δ=7.56-7.44 (m, 3H), 7.40-7.24 (m, 7H), 7.16 (s, 1H), 7.04 (dd, 1H), 7.01-6.98 (m, 1H), 6.80 (d, 1H), 5.05 (s, 2H), 4.34 (q, 2H), 1.32 (t, 3H).

LC-MS (Method 3): $R_t$=3.03 min; MS (ESIpos): m/z=433 [M+H]$^+$.

Example 44A

Ethyl 1-(3-chlorophenyl)-5-(3-hydroxyphenyl)-1H-pyrazole-3-carboxylate

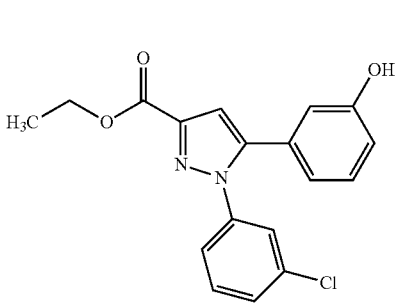 [SMILES: CCOC(=O)c1cc(-c2cccc(O)c2)n(-c2cccc(Cl)c2)n1]

19.1 g (44.1 mmol) of the compound of Example 43A are provided in 367 ml of conc. acetic acid, 23.5 g (11.0 mmol) of palladium on activated carbon (5%) are added, and the mixture is stirred under a hydrogen atmosphere at room temperature overnight. The reaction mixture is subsequently filtered, the filtrate is concentrated, the residue is taken up in dichloromethane and washed with an aqueous sodium bicarbonate solution, and the organic phase is dried over sodium sulfate and concentrated. 12.7 g of the title compound with 63% purity (53% of theory) are obtained.

LC-MS (Method 1): $R_t$=2.41 min; MS (ESIpos): m/z=343 [M+H]$^+$.

Example 45A

Ethyl 1-(3-chloro-4-fluorophenyl)-5-(3-cyanophenyl)-1H-pyrazole-3-carboxylate

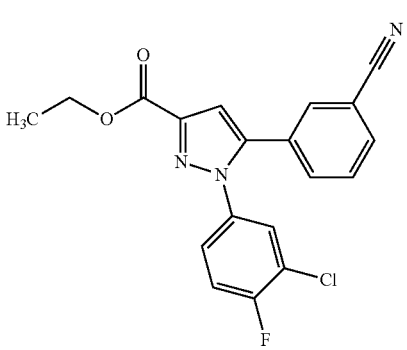 [SMILES: CCOC(=O)c1cc(-c2cccc(C#N)c2)n(-c2ccc(F)c(Cl)c2)n1]

The preparation of the title compound takes place starting from the compound of Example 4A in analogy to the synthesis of the compound of Example 21A. 0.50 g (80% of theory) of the title compound are obtained.

$^1$H-NMR (400 MHz, DMSO-d$_6$): δ=7.94-7.91 (m, 1H), 7.87 (dt, 1H), 7.77 (dd, 1H), 7.61-7.49 (m, 3H), 7.35 (ddd, 1H), 7.31 (s, 1H), 4.35 (q, 2H), 1.32 (t, 3H).

LC-MS (Method 1): R$_t$=2.61 min; MS (ESIpos): m/z=370 [M+H]$^+$.

Example 46A

Ethyl 1-(3-chloro-4-fluorophenyl)-5-(3-fluorophenyl)-1H-pyrazole-3-carboxylate

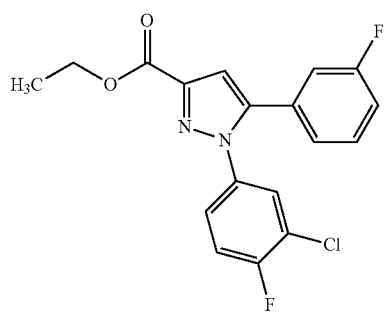 [SMILES: CCOC(=O)c1cc(-c2cccc(F)c2)n(-c2ccc(F)c(Cl)c2)n1]

The preparation of the title compound takes place starting from the compound of Example 8A in analogy to the synthesis of the compound of Example 21A. 0.60 g (93% of theory) of the title compound are obtained.

$^1$H-NMR (400 MHz, DMSO-d$_6$): δ=7.75 (dd, 1H), 7.53 (t, 1H), 7.47-7.39 (m, 1H), 7.35 (ddd, 1H), 7.29-7.22 (m, 3H), 7.09-7.05 (m, 1H), 4.34 (q, 2H), 1.32 (t, 3H).

LC-MS (Method 1): R$_t$=2.77 min; MS (ESIpos): m/z=363 [M+H]$^+$.

Example 47A

Ethyl 1-(3-chloro-4-fluorophenyl)-5-[3-(trifluoromethyl)phenyl]-1H-pyrazole-3-carboxylate

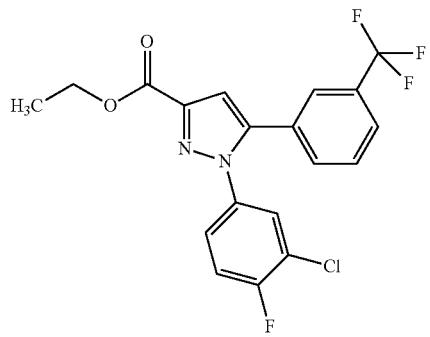 [SMILES: CCOC(=O)c1cc(-c2cccc(C(F)(F)F)c2)n(-c2ccc(F)c(Cl)c2)n1]

The preparation of the title compound takes place starting from the compound of Example 9A in analogy to the synthesis of the compound of Example 21A. 5.10 g (100% of theory) of the title compound are obtained.

$^1$H-NMR (400 MHz, DMSO-d$_6$): δ=7.80-7.74 (m, 2H), 7.72-7.50 (m, 4H), 7.37 (ddd, 1H), 7.33 (s, 1H), 4.35 (q, 2H), 1.33 (t, 3H).

LC-MS (Method 3): R$_t$=2.87 min; MS (ESIpos): m/z=413 [M+H]$^+$.

Example 48A

Ethyl 1-(3-chloro-4-fluorophenyl)-5-[3-fluoro-5-(trifluoromethyl)phenyl]-1H-pyrazole-3-carboxylate

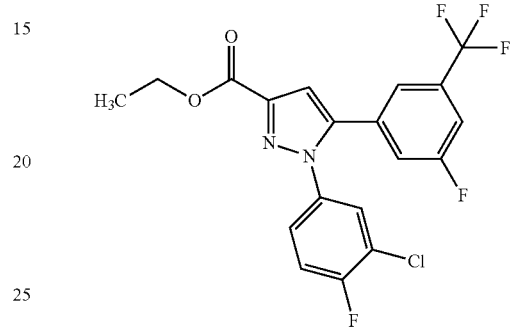

The preparation of the title compound takes place starting from the compound of Example 17A in analogy to the synthesis of the compound of Example 21A. 2.43 g of the title compound with 36% purity are obtained.

LC-MS (Method 1): R$_t$=2.95 min; MS (ESIpos): m/z=431 [M+H]$^+$.

Example 49A

Ethyl 1-(3-chlorophenyl)-5-[3-fluoro-5-(trifluoromethyl)phenyl]-1H-pyrazole-3-carboxylate

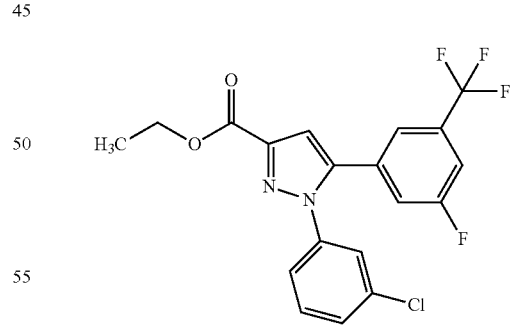

The preparation of the title compound takes place starting from the compound of Example 17A and 3-chlorophenylhydrazine hydrochloride in analogy to the synthesis of the compound of Example 21A. 2.08 g of the title compound are obtained.

LC-MS (Method 5): R$_t$=1.52 min; MS (ESIpos): m/z=413 [M+H]$^+$.

Example 50A

Ethyl 1-(3-bromophenyl)-5-(3-chlorophenyl)-1H-pyrazole-3-carboxylate

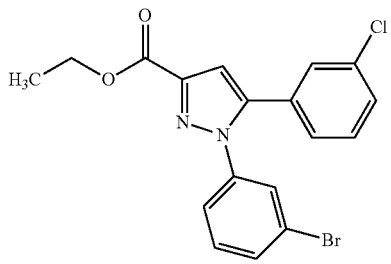

The preparation of the title compound takes place starting from the compound of Example 3A and 3-bromophenylhydrazine hydrochloride in analogy to the synthesis of the compound of Example 21A. 2.50 g of the title compound with 70% purity (67% of theory) are obtained.

LC-MS (Method 1): $R_t$=2.93 min; MS (ESIpos): m/z=405 [M+H]$^+$.

Example 51A

Ethyl 1-(3-bromophenyl)-5-(3-chloro-4-fluorophenyl)-1H-pyrazole-3-carboxylate

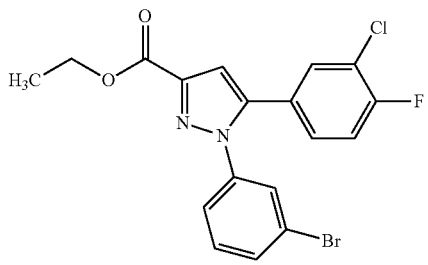 [SMILES: CCOC(=O)c1cc(-c2ccc(F)c(Cl)c2)n(-c2cccc(Br)c2)n1]

The preparation of the title compound takes place starting from the compound of Example 1A and 3-bromophenylhydrazine hydrochloride in analogy to the synthesis of the compound of Example 21A. 689 mg of the title compound with 76% purity (77% of theory) are obtained.

$^1$H-NMR (400 MHz, DMSO-d$_6$): δ=7.73-7.69 (m, 2H), 7.52 (dt, 1H), 7.43 (t, 1H), 7.35-7.30 (m, 2H), 7.25 (s, 1H), 7.18 (dt, 1H), 4.35 (q, 2H), 1.32 (t, 3H).

LC-MS (Method 7): $R_t$=2.55 min; MS (ESIpos): m/z=423 [M+H]$^+$.

Example 52A

Ethyl 5-(3-bromo-5-fluorophenyl)-1-(3-chloro-4-fluorophenyl)-1H-pyrazole-3-carboxylate

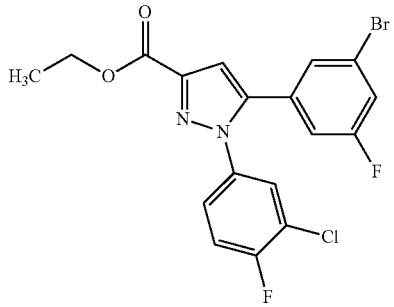 [SMILES: CCOC(=O)c1cc(-c2cc(F)cc(Br)c2)n(-c2ccc(F)c(Cl)c2)n1]

The preparation of the title compound takes place starting from the compound of Example 18A in analogy to the synthesis of the compound of Example 21A. 3.87 g (89% of theory) of the title compound are obtained.

$^1$H-NMR (400 MHz, DMSO-d$_6$): δ=7.80 (dd, 1H), 7.63 (dt, 1H), 7.55 (t, 1H), 7.41-7.35 (m, 2H), 7.31 (s, 1H), 7.24-7.20 (m, 1H), 4.34 (q, 2H), 1.32 (t, 3H).

LC-MS (Method 1): $R_t$=2.98 min; MS (ESIpos): m/z=441 [M+H]$^+$.

Example 53A

Ethyl 1-(3-chloro-4-fluorophenyl)-5-(3-methoxyphenyl)-1H-pyrazole-3-carboxylate

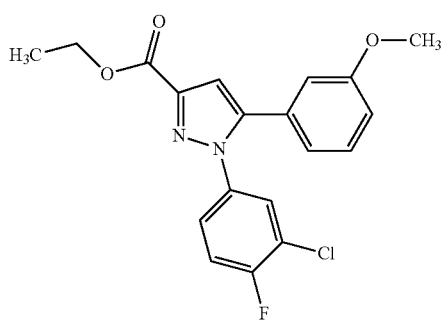 [SMILES: CCOC(=O)c1cc(-c2cccc(OC)c2)n(-c2ccc(F)c(Cl)c2)n1]

The preparation of the title compound takes place starting from the compound of Example 10A in analogy to the synthesis of the compound of Example 21A. 0.60 g (97% of theory) of the title compound are obtained.

$^1$H-NMR (400 MHz, DMSO-d$_6$): δ=7.74 (dd, 1H), 7.52 (t, 1H), 7.34 (ddd, 1H), 7.29 (t, 1H), 7.17 (s, 1H), 6.96 (dd, 1H), 6.91 (t, 1H), 6.79 (d, 1H), 4.34 (q, 2H), 3.71 (s, 3H), 1.32 (t, 3H).

LC-MS (Method 1): $R_t$=2.77 min; MS (ESIpos): m/z=375 [M+H]$^+$.

Example 54A

Ethyl 5-[3,5-bis(trifluoromethyl)phenyl]-1-(3-chlorophenyl)-1H-pyrazole-3-carboxylate

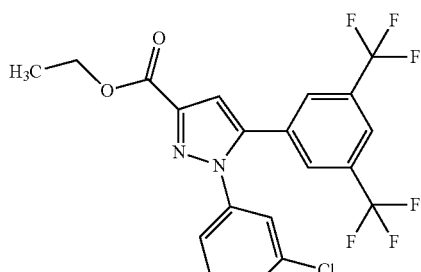

The preparation of the title compound takes place starting from the compound of Example 19A and 3-chlorophenylhydrazine hydrochloride in analogy to the synthesis of the compound of Example 21A. 2.42 g (62% of theory) of the title compound are obtained.

$^1$H-NMR (400 MHz, DMSO-d$_6$): δ=8.15 (s, 1H), 7.96 (s, 2H), 7.63-7.57 (m, 2H), 7.55 (s, 1H), 7.50 (t, 1H), 7.34 (d, 1H), 4.36 (q, 2H), 1.33 (t, 3H).

Example 55A

Ethyl 1-(4-chlorophenyl)-5-[3-(trifluoromethyl)phenyl]-1H-pyrazole-3-carboxylate

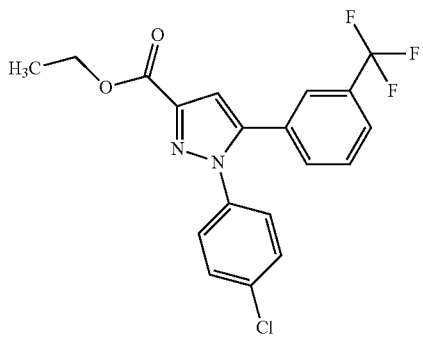 [SMILES: CCOC(=O)c1cc(-c2cccc(C(F)(F)F)c2)n(-c2ccc(Cl)cc2)n1]

The preparation of the title compound takes place starting from the compound of Example 9A and 4-chlorophenylhydrazine hydrochloride in analogy to the synthesis of the compound of Example 21A. 4.78 g (98% of theory) of the title compound are obtained.

$^1$H-NMR (400 MHz, DMSO-d$_6$): δ=7.76 (d, 1H), 7.67-7.59 (m, 2H), 7.58-7.53 (m, 3H), 7.43-7.38 (m, 2H), 7.33 (s, 1H), 4.35 (q, 2H), 1.33 (t, 3H).

LC-MS (Method 6): R$_t$=4.11 min; MS (ESIpos): m/z=395 [M+H]$^+$.

Example 56A

Ethyl 1-(4-chlorophenyl)-5-(3-fluorophenyl)-1H-pyrazole-3-carboxylate

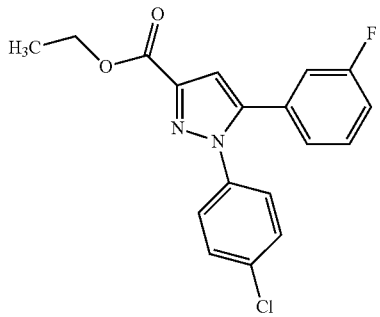 [SMILES: CCOC(=O)c1cc(-c2cccc(F)c2)n(-c2ccc(Cl)cc2)n1]

The preparation of the title compound takes place starting from the compound of Example 8A and 4-chlorophenylhydrazine hydrochloride in analogy to the synthesis of the compound of Example 21A. 43.4 g (87% of theory) of the title compound are obtained.

$^1$H-NMR (400 MHz, DMSO-d$_6$): δ=7.58-7.53 (m, 2H), 7.46-7.36 (m, 3H), 7.28-7.19 (m, 3H), 7.06 (d, 1H), 4.34 (q, 2H), 1.32 (t, 3H).

LC-MS (Method 6): R$_t$=3.93 min; MS (ESIpos): m/z=345 [M+H]$^+$.

Example 57A

Ethyl 1-(3-chloro-4-fluorophenyl)-5-(3-fluoro-5-methylphenyl)-1H-pyrazole-3-carboxylate

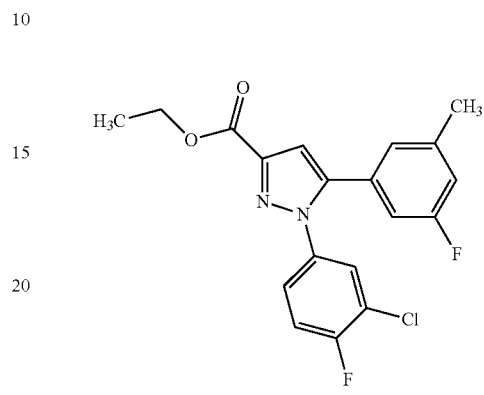

The preparation of the title compound takes place starting from the compound of Example 20A in analogy to the synthesis of the compound of Example 21A. 2.79 g of the title compound with 78% purity are obtained.

$^1$H-NMR (400 MHz, DMSO-d$_6$): δ=7.75 (dd, 1H), 7.53 (t, 1H), 7.34 (ddd, 1H), 7.19 (s, 1H), 7.10 (d, 1H), 7.01 (s, 1H), 6.91 (s, 1H), 4.34 (q, 2H), 2.27 (s, 3H), 1.32 (t, 3H).

LC-MS (Method 1): R$_t$=2.98 min; MS (ESIpos): m/z=377 [M+H]$^+$.

Example 58A

Ethyl 1-(3-chlorophenyl)-5-(3-fluoro-5-methylphenyl)-1H-pyrazole-3-carboxylate

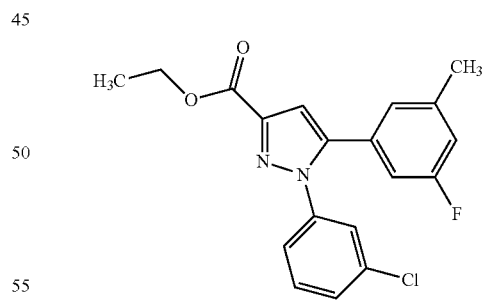

The preparation of the title compound takes place starting from the compound of Example 20A and 3-chlorophenylhydrazine hydrochloride in analogy to the synthesis of the compound of Example 21A. 1.75 g of the title compound are obtained.

$^1$H-NMR (400 MHz, DMSO-d$_6$): δ=7.58-7.53 (m, 2H), 7.48 (t, 1H), 7.29-7.25 (m, 1H), 7.19 (s, 1H), 7.12-7.07 (m, 1H), 7.01 (s, 1H), 6.91-6.86 (m, 1H), 4.34 (q, 2H), 2.27 (s, 3H), 1.32 (t, 3H).

LC-MS (Method 1): $R_t$=2.97 min; MS (ESIpos): m/z=359 [M+H]$^+$.

Example 59A

Ethyl 5-(3-chloro-4-fluorophenyl)-1-(3-cyanophenyl)-1H-pyrazole-3-carboxylate

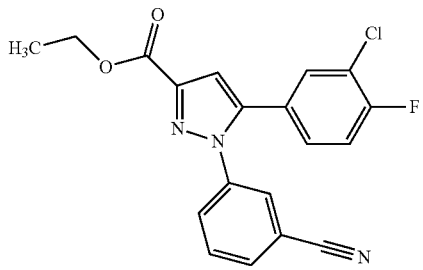 [SMILES: CCOC(=O)c1cc(-c2ccc(F)c(Cl)c2)n(-c2cccc(C#N)c2)n1]

100 mg (0.236 mmol) of the compound of Example 51A are provided in 1 ml of 1-methyl-2-pyrrolidone, 55.4 mg (0.472 mmol) of zinc cyanide and 27.3 mg (0.024 mmol) of tetrakis(triphenylphosphine)palladium(0) are added, and the mixture is heated in a closed glass vessel at 200° C. under microwave irradiation for 30 min. The reaction mixture is subsequently filtered through kieselguhr and eluted with methanol, the filtrate is rendered weakly acidic with a 1N aqueous hydrogen chloride solution and concentrated, and the residue is purified by preparative HPLC (RP18 column; mobile phase: acetonitrile/water gradient). 33 mg (34% of theory) of the title compound are obtained.

LC-MS (Method 1): $R_t$=2.72 min; MS (ESIpos): m/z=370 [M+H]$^+$.

Example 60A

Ethyl 5-(3-chlorophenyl)-1-(3-cyano-4-fluorophenyl)-1H-pyrazole-3-carboxylate

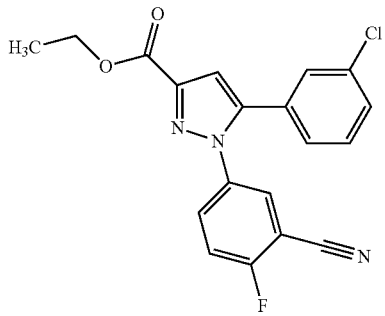 [SMILES: CCOC(=O)c1cc(-c2cccc(Cl)c2)n(-c2ccc(F)c(C#N)c2)n1]

The preparation of the title compound takes place starting from the compound of Example 3A and 3-cyano-4-fluorophenylhydrazine hydrochloride in analogy to the synthesis of the compound of Example 21A. 0.76 g of the title compound with 46% purity (23% of theory) are obtained.

LC-MS (Method 7): $R_t$=2.29 min; MS (ESIpos): m/z=370 [M+H]$^+$.

Example 61A

Ethyl 5-(3-chlorophenyl)-1-(3-cyanophenyl)-1H-pyrazole-3-carboxylate

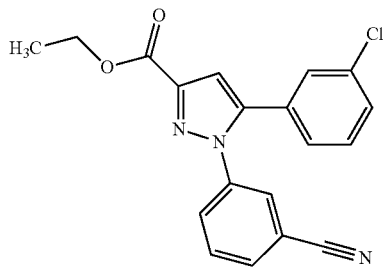 [SMILES: CCOC(=O)c1cc(-c2cccc(Cl)c2)n(-c2cccc(C#N)c2)n1]

The preparation of the title compound takes place starting from the compound of Example 3A and 3-cyanophenylhydrazine hydrochloride in analogy to the synthesis of the compound of Example 21A. 540 mg of the title compound with 69% purity (25% of theory) are obtained.

LC-MS (Method 7): $R_t$=2.24 min; MS (ESIpos): m/z=352 [M+H]$^+$.

Example 62A

Ethyl 1,5-bis(3-cyanophenyl)-1H-pyrazole-3-carboxylate

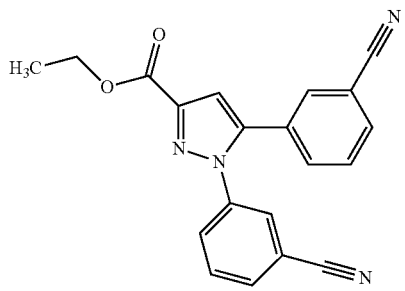 [SMILES: CCOC(=O)c1cc(-c2cccc(C#N)c2)n(-c2cccc(C#N)c2)n1]

The preparation of the title compound takes place starting from the compound of Example 4A and 3-cyanophenylhydrazine hydrochloride in analogy to the synthesis of the compound of Example 21A. 440 mg of the title compound with 26% purity are obtained.

LC-MS (Method 7): $R_t$=1.95 min; MS (ESIpos): m/z=343 [M+H]$^+$.

Example 63A

Ethyl 1-(3-cyano-4-fluorophenyl)-5-(3-cyanophenyl)-1H-pyrazole-3-carboxylate

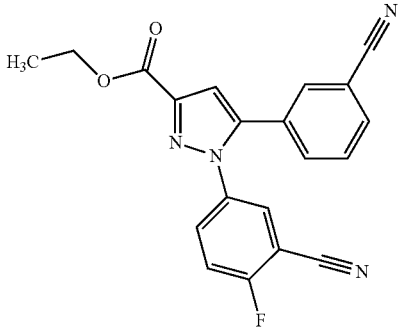 [SMILES: CCOC(=O)c1cc(-c2cccc(C#N)c2)n(-c2ccc(F)c(C#N)c2)n1]

The preparation of the title compound takes place starting from the compound of Example 4A and 3-cyano-4-fluorophenylhydrazine hydrochloride in analogy to the synthesis of the compound of Example 21A. 510 mg of the title compound with 27% purity are obtained.

LC-MS (Method 7): $R_t$=2.00 min; MS (ESIpos): m/z=361 [M+H]$^+$.

Example 64A

Ethyl 5-(3-chloro-5-fluorophenyl)-1-(3-cyanophenyl)-1H-pyrazole-3-carboxylate

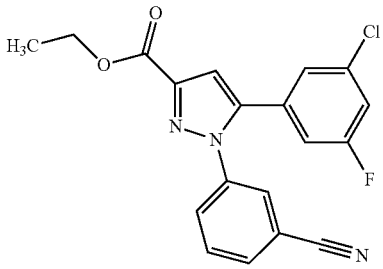 [SMILES: CCOC(=O)c1cc(-c2cc(F)cc(Cl)c2)n(-c2cccc(C#N)c2)n1]

The preparation of the title compound takes place starting from the compound of Example 1A and 3-cyanophenylhydrazine hydrochloride in analogy to the synthesis of the compound of Example 21A. 1.96 g of the title compound with 55% purity (86% of theory) are obtained.

LC-MS (Method 1): $R_t$=2.71 min; MS (ESIpos): m/z=370 [M+H]$^+$.

Example 65A

Ethyl 5-(3-chloro-5-fluorophenyl)-1-(3-cyano-4-fluorophenyl)-1H-pyrazole-3-carboxylate

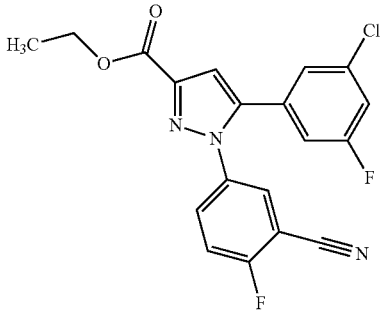 [SMILES: CCOC(=O)c1cc(-c2cc(F)cc(Cl)c2)n(-c2ccc(F)c(C#N)c2)n1]

The preparation of the title compound takes place starting from the compound of Example 1A and 3-cyano-4-fluorophenylhydrazine hydrochloride in analogy to the synthesis of the compound of Example 21A. 2.66 g of the title compound with 49% purity (100% of theory) are obtained.

LC-MS (Method 1): $R_t$=2.75 min; MS (ESIpos): m/z=388 [M+H]$^+$.

Example 66A

Ethyl 1-(3-chlorophenyl)-5-[3-(2-hydroxyethoxy)phenyl]-1H-pyrazole-3-carboxylate

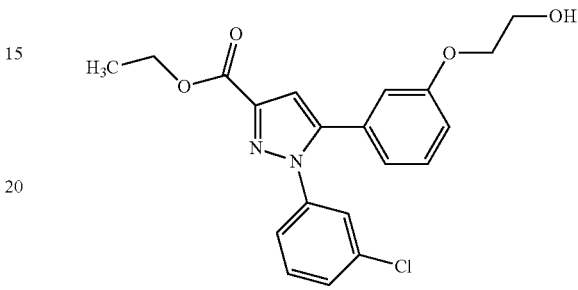

100 mg (0.29 mmol) of the compound of Example 44A are provided in 2 ml of dry acetone, 44.4 mg (0.32 mmol) of potassium carbonate and 36.5 mg (0.29 mmol) of 2-bromoethanol are added, and the mixture is heated under reflux overnight. The reaction mixture is subsequently purified by preparative HPLC (RP18 column; mobile phase: acetonitrile/water gradient with the addition of 0.1% formic acid) and 13.1 mg of the title compound are obtained.

$^1$H-NMR (400 MHz, DMSO-d$_6$): δ=7.56-7.44 (m, 3H), 7.30-7.24 (m, 2H), 7.16 (s, 1H), 6.96 (dd, 1H), 6.91-6.89 (m, 1H), 6.78 (d, 1H), 4.85 (t, 1H), 4.34 (q, 2H), 3.91 (t, 2H), 3.66 (q, 2H), 1.32 (t, 3H).

LC-MS (Method 1): $R_t$=2.35 min; MS (ESIpos): m/z=387 [M+H]$^+$.

Example 67A

Ethyl 5-{3-[3-(acetyloxy)propoxy]phenyl}-1-(3-chlorophenyl)-1H-pyrazole-3-carboxylate

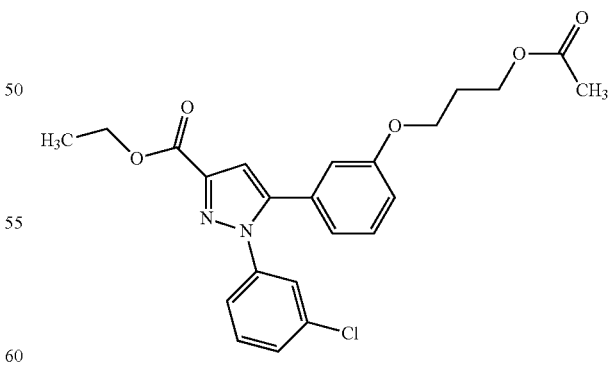

100 mg (0.292 mmol) of the compound of Example 44A are provided in 1 ml of dry DMF, 242 mg (1.75 mmol) of potassium carbonate and 158 mg (0.875 mmol) of 1-acetoxy-3-bromopropane are added, and the mixture is stirred at 90° C. for 4 h. The reaction mixture is subsequently purified by preparative HPLC (RP18 column; mobile phase: acetonitrile/ water gradient with the addition of 0.1% formic acid) and 109 mg (84% of theory) of the title compound are obtained.

LC-MS (Method 1): $R_t$=2.79 min; MS (ESIpos): m/z=443 [M+H]$^+$.

Example 68A

Ethyl 1-(3-chlorophenyl)-5-[3-(3-chloropropoxy)phenyl]-1H-pyrazole-3-carboxylate

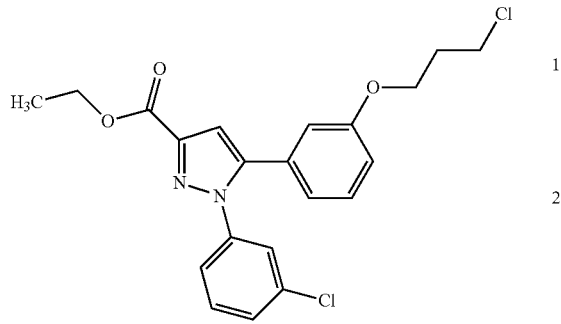

100 mg (0.292 mmol) of the compound of Example 44A are provided in 3 ml of dry DMF, 76.6 mg (0.554 mmol) of potassium carbonate and 133 mg (0.846 mmol) of 1-bromo-3-chloropropane are added, and the mixture is heated under reflux for 4 h. The reaction mixture is subsequently purified by preparative HPLC (RP18 column; mobile phase: acetonitrile/water gradient with the addition of 0.1% formic acid) and 42 mg of the title compound with 49% purity (17% of theory) are obtained.

LC-MS (Method 7): $R_t$=2.53 min; MS (ESIpos): m/z=419 [M+H]$^+$.

Example 69A

Ethyl 1-(3-chlorophenyl)-5-[3-(2-methoxyethoxy)phenyl]-1H-pyrazole-3-carboxylate

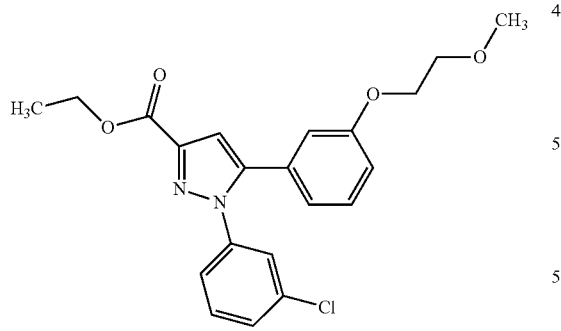

100 mg (0.292 mmol) of the compound of Example 44A are provided in 2 ml of dry acetone, 44.4 mg (0.321 mmol) of potassium carbonate and 40.6 mg (0.292 mmol) of 2-bromoethyl methyl ether are added, and the mixture is heated under reflux overnight. The reaction mixture is subsequently purified by preparative HPLC (RP18 column; mobile phase: acetonitrile/water gradient with the addition of 0.1% formic acid) and 48 mg (41% of theory) of the title compound are obtained.

$^1$H-NMR (400 MHz, DMSO-d$_6$): δ=7.56-7.44 (m, 3H), 7.30-7.24 (m, 2H), 7.17 (s, 1H), 6.97 (dd, 1H), 6.93-6.89 (m, 1H), 6.79 (d, 1H), 4.34 (q, 2H), 4.05-4.00 (m, 2H), 3.61-3.57 (m, 2H), 3.28 (s, 3H), 1.32 (t, 3H).

LC-MS (Method 1): $R_t$=2.68 min; MS (ESIpos): m/z=401 [M+H]$^+$.

Example 70A

Ethyl 1-(3-chlorophenyl)-5-[3-(3-pyrrolidin-1-ylpropoxy)phenyl]-1H-pyrazole-3-carboxylate

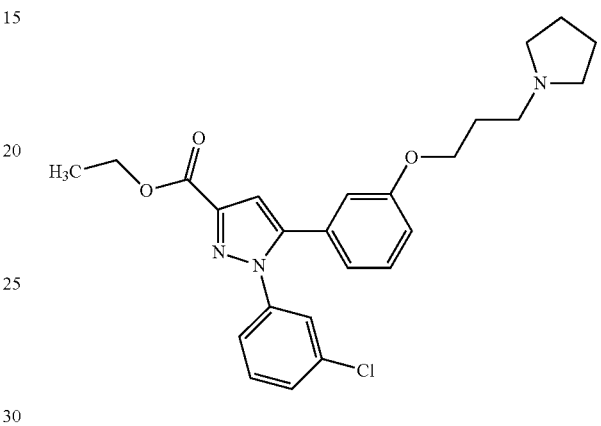

41.5 mg (0.10 mmol) of the compound of Example 68A and 83 μl (0.99 mmol) of pyrrolidine in 3 ml of ethanol are stirred at 80° C. overnight. The reaction mixture is subsequently purified by preparative HPLC (RP18 column; mobile phase: acetonitrile/water gradient). 18.3 mg of the title compound are obtained.

LC-MS (Method 7): $R_t$=1.51 min; MS (ESIpos): m/z=454 [M+H]$^+$.

Example 71A 1-(3-Chloro-4-fluorophenyl)-5-(3-chloro-5-fluorophenyl)-1H-pyrazole-3-carboxylic acid

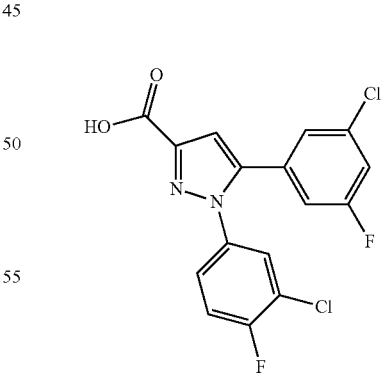

5.11 g (12.9 mmol) of the compound of Example 21A are provided in 142 ml of tetrahydrofuran and, at room temperature, 3.08 g (129 mmol) of lithium hydroxide and 47 ml of water are added. The mixture is stirred at room temperature overnight and a 1N aqueous hydrogen chloride solution is subsequently added until the pH is acidic, the mixture extracted with ethyl acetate, and the organic phase is washed ¹H-NMR (400 MHz, DMSO-d₆): δ=13.2 (s, 1H), 7.78 (dd, 1H), 7.58-7.49 (m, 2H), 7.36 (ddd, 1H), 7.28-7.25 (m, 1H), 7.24 (s, 1H), 7.21-7.16 (m, 1H).

LC-MS (Method 1): R$_t$=2.52 min; MS (ESIpos): m/z=369 [M+H]⁺.

Example 72A 5-(3-Chloro-5-fluorophenyl)-1-(3-chlorophenyl)-1H-pyrazole-3-carboxylic acid

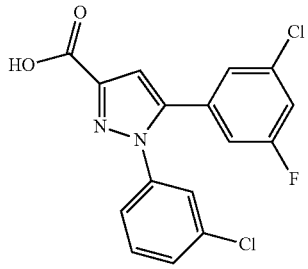 [SMILES: O=C(O)c1cc(-c2cc(F)cc(Cl)c2)n(-c2cccc(Cl)c2)n1]

The preparation of the title compound takes place starting from the compound of Example 22A in analogy to the synthesis of the compound of Example 71A. 4.18 g (78% of theory) of the title compound are obtained.

¹H-NMR (400 MHz, DMSO-d₆): δ=13.1 (s, 1H), 7.59-7.55 (m, 2H), 7.54-7.45 (m, 2H), 7.30-7.26 (m, 1H), 7.26-7.23 (m, 2H), 7.20-7.15 (m, 1H).

LC-MS (Method 1): R$_t$=2.49 min; MS (ESIpos): m/z=351 [M+H]⁺.

Example 73A 1-(3-Chlorophenyl)-5-(3,5-difluorophenyl)-1H-pyrazole-3-carboxylic acid

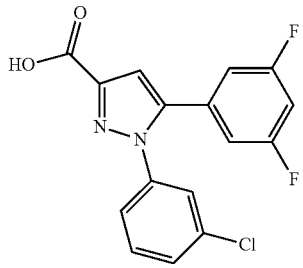 [SMILES: O=C(O)c1cc(-c2cc(F)cc(F)c2)n(-c2cccc(Cl)c2)n1]

2.50 g (6.89 mmol) of the compound of Example 23A are provided in 62 ml of a 2:1 mixture of 1,4-dioxane and water, 35 ml (70 mmol) of a 2N solution of lithium hydroxide in water are added, and the mixture is stirred at room temperature overnight. The mixture is concentrated and a 2N aqueous hydrogen chloride solution is subsequently added to the residue until the pH is acidic, the mixture is extracted with ethyl acetate, and the organic phase is dried over sodium sulfate, filtered and concentrated. 2.28 g (99% of theory) of the title compound are obtained.

¹H-NMR (400 MHz, DMSO-d₆): δ=13.2 (s, 1H), 7.59-7.54 (m, 2H), 7.53-7.47 (m, 1H), 7.33 (tt, 1H), 7.30-7.26 (m, 1H), 7.24 (s, 1H), 7.10-7.02 (m, 2H).

LC-MS (Method 3): R$_t$=2.21 min; MS (ESIpos): m/z=335 [M+H]⁺.

Example 74A 1,5-Bis(3-chlorophenyl)-1H-pyrazole-3-carboxylic acid

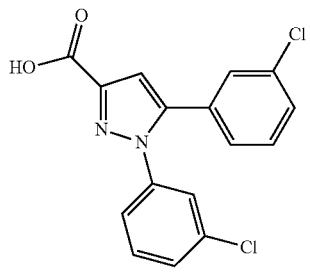 [SMILES: O=C(O)c1cc(-c2cccc(Cl)c2)n(-c2cccc(Cl)c2)n1]

The preparation of the title compound takes place starting from the compound of Example 24A in analogy to the synthesis of the compound of Example 71A. 5.97 g (94% of theory) of the title compound are obtained.

¹H-NMR (400 MHz, DMSO-d₆): δ=13.1 (s, 1H), 7.57-7.37 (m, 6H), 7.28-7.24 (m, 1H), 7.21-7.18 (m, 1H), 7.17 (s, 1H).

LC-MS (Method 3): R$_t$=2.28 min; MS (ESIpos): m/z=333 [M+H]⁺.

Example 75A 1,5-Bis(3-chloro-4-fluorophenyl)-1H-pyrazole-3-carboxylic acid

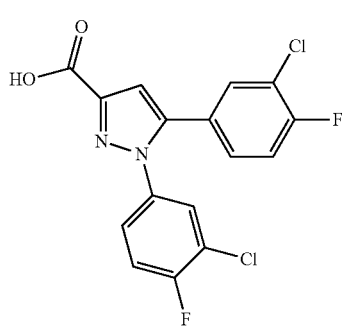 [SMILES: O=C(O)c1cc(-c2ccc(F)c(Cl)c2)n(-c2ccc(F)c(Cl)c2)n1]

The preparation of the title compound takes place starting from the compound of Example 25A in analogy to the synthesis of the compound of Example 71A. 5.15 g (96% of theory) of the title compound are obtained.

¹H-NMR (400 MHz, DMSO-d₆): δ=13.1 (s, 1H), 7.76 (dd, 1H), 7.65 (dd, 1H), 7.52 (t, 1H), 7.44 (t, 1H), 7.33 (ddd, 1H), 7.23 (ddd, 1H), 7.18 (s, 1H)

LC-MS (Method 1): $R_t$=2.49 min; MS (ESIpos): m/z=369 [M+H]$^+$.

Example 76A 1-(3-Chlorophenyl)-5-[3-(trifluoromethoxy)phenyl]-1H-pyrazole-3-carboxylic acid

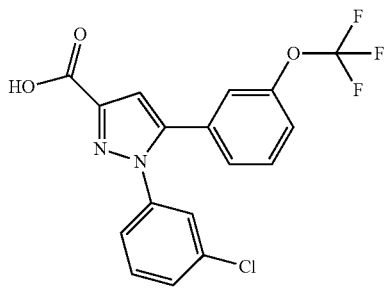 [SMILES: O=C(O)c1cc(-c2cccc(OC(F)(F)F)c2)n(-c2cccc(Cl)c2)n1]

10.8 g (26.2 mmol) of the compound of Example 26A are provided in 236 ml of 1,4-dioxane, 236 ml (472 mmol) of a 2N solution of lithium hydroxide in water are added, and the mixture is stirred at 70° C. for 2 h. The mixture is concentrated and a 2N aqueous hydrogen chloride solution is subsequently added to the residue until the pH is acidic, the mixture is extracted with dichloromethane, and the organic phase is dried over magnesium sulfate, filtered and concentrated. 9.90 g (99% of theory) of the title compound are obtained.

$^1$H-NMR (400 MHz, DMSO-d$_6$): δ=13.1 (s, 1H), 7.59-7.45 (m, 4H), 7.44-7.38 (m, 2H), 7.31-7.26 (m, 1H), 7.22-7.18 (m, 2H).

LC-MS (Method 1): $R_t$=2.77 min; MS (ESIpos): m/z=383 [M+H]$^+$.

Example 77A 1-(3-Chlorophenyl)-5-[4-fluoro-3-(trifluoromethyl)phenyl]-1H-pyrazole-3-carboxylic acid

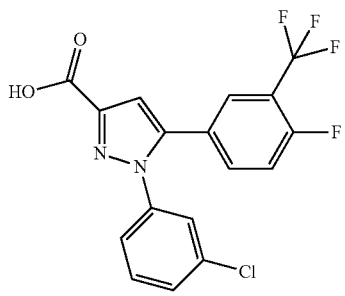 [SMILES: O=C(O)c1cc(-c2ccc(F)c(C(F)(F)F)c2)n(-c2cccc(Cl)c2)n1]

3.60 g (8.72 mmol) of the compound of Example 27A are provided in 50 ml of 1,4-dioxane, 50 ml (50 mmol) of a 1N solution of lithium hydroxide in water are added, and the mixture is heated under reflux for 1 h. The mixture is concentrated, the residue is diluted with water, a conc. aqueous hydrogen chloride solution is subsequently added until the pH is acidic, the mixture is extracted with ethyl acetate, and the organic phase is dried over magnesium sulfate, filtered and concentrated. 3.30 g (98% of theory) of the title compound are obtained.

$^1$H-NMR (400 MHz, DMSO-d$_6$): δ=7.70 (d, 1H), 7.55-7.44 (m, 3H), 7.40 (t, 1H), 7.30 (s, 1H), 7.18 (d, 1H), 6.99 (s, 1H).

LC-MS (Method 3): $R_t$=2.41 min; MS (ESIpos): m/z=385 [M+H]$^+$.

Example 78A 1-(3-Chloro-4-fluorophenyl)-5-[3-(trifluoromethoxy)phenyl]-1H-pyrazole-3-carboxylic acid

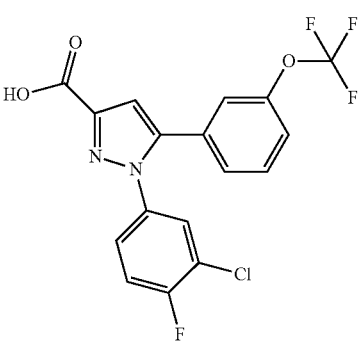 [SMILES: O=C(O)c1cc(-c2cccc(OC(F)(F)F)c2)n(-c2ccc(F)c(Cl)c2)n1]

The preparation of the title compound takes place starting from the compound of Example 28A in analogy to the synthesis of the compound of Example 71A. 3.14 g (96% of theory) of the title compound are obtained.

$^1$H-NMR (400 MHz, DMSO-d$_6$): δ=13.1 (s, 1H), 7.72 (dd, 1H), 7.59-7.50 (m, 2H), 7.44-7.34 (m, 3H), 7.23-7.18 (m, 2H).

LC-MS (Method 1): $R_t$=2.56 min; MS (ESIpos): m/z=401 [M+H]$^+$.

Example 79A 5-(3-Chloro-4-fluorophenyl)-1-(3-chlorophenyl)-1H-pyrazole-3-carboxylic acid

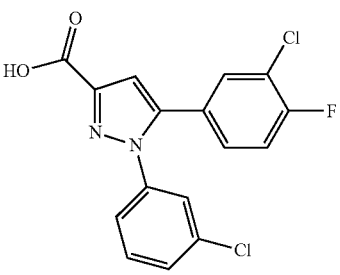 [SMILES: O=C(O)c1cc(-c2ccc(F)c(Cl)c2)n(-c2cccc(Cl)c2)n1]

The preparation of the title compound takes place starting from the compound of Example 29A in analogy to the synthesis of the compound of Example 71A. 5.30 g (100% of theory) of the title compound are obtained.

$^1$H-NMR (400 MHz, DMSO-d$_6$): δ=13.1 (s, 1H), 7.63 (dd, 1H), 7.57-7.52 (m, 2H), 7.51-7.42 (m, 2H), 7.28-7.21 (m, 2H), 7.17 (s, 1H).

Example 80A 5-(3-Fluorophenyl)-1-(3-methoxyphenyl)-1H-pyrazole-3-carboxylic acid

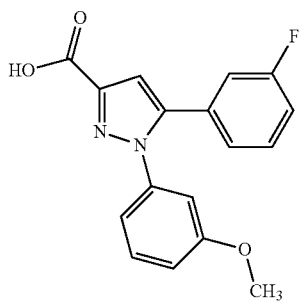 [SMILES: COc1cccc(-n2nc(C(=O)O)cc2-c2cccc(F)c2)c1]

34.0 g (99.9 mmol) of the compound of Example 30A are provided in 150 ml of 1,4-dioxane, 150 ml (300 mmol) of a 2N solution of lithium hydroxide in water are added, and the mixture is stirred at 70° C. for 1 h. The mixture is concentrated, a conc. aqueous hydrogen chloride solution is subsequently added to the residue until the pH is acidic, the mixture is extracted with dichloromethane, and the organic phase is dried over magnesium sulfate, filtered and concentrated. The residue is recrystallized from diethyl ether. 26.1 g (84% of theory) of the title compound are obtained.

$^1$H-NMR (400 MHz, DMSO-d$_6$): δ=13.0 (s, 1H), 7.45-7.32 (m, 2H), 7.26-7.13 (m, 3H), 7.08 (d, 1H), 7.03 (dd, 1H), 6.95 (t, 1H), 6.85 (d, 1H), 3.72 (s, 3H).

LC-MS (Method 1): R$_t$=2.33 min; MS (ESIpos): m/z=313 [M+H]$^+$.

Example 81A 1-(3-Chlorophenyl)-5-(3-methoxyphenyl)-1H-pyrazole-3-carboxylic acid

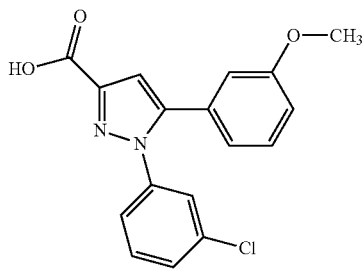 [SMILES: COc1cccc(-c2cc(C(=O)O)nn2-c2cccc(Cl)c2)c1]

1.50 g (4.20 mmol) of the compound of Example 31A are provided in 20 ml of 1,4-dioxane, 20 ml (20 mmol) of a 1N solution of lithium hydroxide in water are added, and the mixture is stirred at 70° C. for 1 h. The mixture is concentrated, a 1N aqueous hydrogen chloride solution is subsequently added to the residue until the pH is acidic, the mixture is extracted with ethyl acetate, and the combined organic phases are dried over magnesium sulfate, filtered and concentrated. 1.32 g (92% of theory) of the title compound are obtained.

$^1$H-NMR (400 MHz, DMSO-d$_6$): δ=13.1 (s, 1H), 7.56-7.44 (m, 3H), 7.32-7.23 (m, 2H), 7.11 (s, 1H), 6.96 (dd, 1H), 6.88 (s, 1H), 6.80 (d, 1H), 3.69 (s, 3H).

LC-MS (Method 3): R$_t$=2.14 min; MS (ESIpos): m/z=329 [M+H]$^+$.

Example 82A 5-(3-Chlorophenyl)-1-[3-(trifluoromethyl)phenyl]-1H-pyrazole-3-carboxylic acid

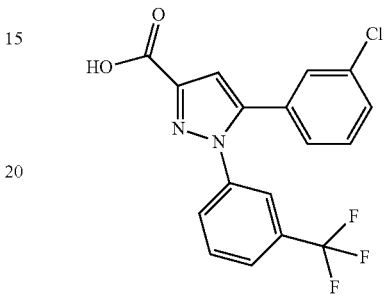

2.00 g (5.07 mmol) of the compound of Example 32A are provided in 37 ml of 1,4-dioxane, a solution of 1.07 g (20.0 mmol) of lithium hydroxide in 37 ml of water is added, and the mixture is stirred at room temperature overnight. The mixture is concentrated, a 1N aqueous hydrogen chloride solution is subsequently added to the residue until the pH is acidic, the mixture is extracted with ethyl acetate, and the combined organic phases are dried over sodium sulfate, filtered and concentrated. 0.74 g (40% of theory) of the title compound are obtained.

$^1$H-NMR (500 MHz, DMSO-d$_6$): δ=7.75 (d, 1H), 7.70-7.62 (m, 2H), 7.54 (d, 1H), 7.45 (d, 1H), 7.42-7.36 (m, 2H), 7.19 (d, 1H), 6.92 (s, 1H).

LC-MS (Method 1): R$_t$=2.65 min; MS (ESIpos): m/z=367 [M+H]$^+$.

Example 83A 1-(3-Chlorophenyl)-5-(3,4-difluorophenyl)-1H-pyrazole-3-carboxylic acid

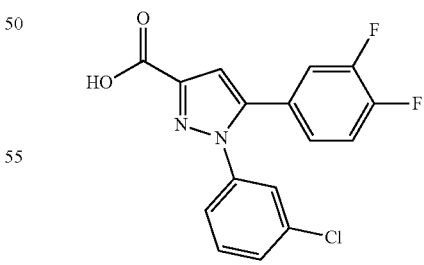

The preparation of the title compound takes place starting from the compound of Example 33A in analogy to the synthesis of the compound of Example 73A. 2.49 g (96% of theory) of the title compound are obtained.

$^1$H-NMR (400 MHz, DMSO-d$_6$): δ=13.1 (s, 1H), 7.57-7.43 (m, 5H), 7.27-7.22 (m, 1H), 7.16 (s, 1H), 7.12-7.06 (m, 1H).

LC-MS (Method 3): $R_t$=2.21 min; MS (ESIpos): m/z=335 [M+H]$^+$.

Example 84A 5-(3-Bromo-4-fluorophenyl)-1-(3-chlorophenyl)-1H-pyrazole-3-carboxylic acid

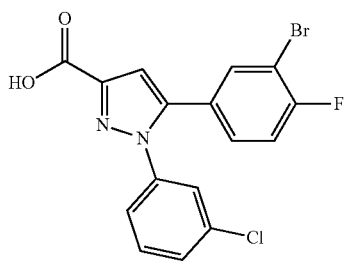 [SMILES: O=C(O)c1cc(-c2ccc(F)c(Br)c2)n(-c2cccc(Cl)c2)n1]

The preparation of the title compound takes place starting from the compound of Example 34A in analogy to the synthesis of the compound of Example 77A. 3.30 g (98% of theory) of the title compound are obtained.

$^1$H-NMR (400 MHz, DMSO-d$_6$): δ=13.1 (s, 1H), 7.72 (dd, 1H), 7.58-7.52 (m, 2H), 7.48 (t, 1H), 7.41 (t, 1H), 7.31-7.22 (m, 2H), 7.17 (s, 1H).

LC-MS (Method 3): $R_t$=2.34 min; MS (ESIpos): m/z=395 [M+H]$^+$.

Example 85A 5-(3-Chlorophenyl)-1-(4-fluorophenyl)-1H-pyrazole-3-carboxylic acid

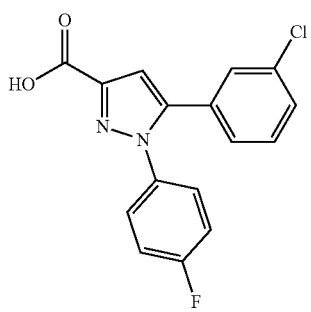 [SMILES: O=C(O)c1cc(-c2cccc(Cl)c2)n(-c2ccc(F)cc2)n1]

23.0 g (66.7 mmol) of the compound of Example 35A are provided in 100 ml of 1,4-dioxane, 100 ml (200 mmol) of a 2N solution of lithium hydroxide in water are added, and the mixture is stirred at 50° C. for 2 h. The mixture is concentrated, a conc. aqueous hydrogen chloride solution is subsequently added until the pH is acidic, the mixture is extracted with dichloromethane, and the organic phase is dried over magnesium sulfate, filtered and concentrated. The residue is stirred in a little diethyl ether, collected by filtration and dried under high vacuum. 17.8 g (84% of theory) of the title compound are obtained.

$^1$H-NMR (400 MHz, DMSO-d$_6$): δ=13.1 (s, 1H), 7.46-7.29 (m, 7H), 7.19-7.14 (m, 2H).

LC-MS (Method 4): $R_t$=3.46 min; MS (ESIpos): m/z=317 [M+H]$^+$.

Example 86A 1-(3-Chlorophenyl)-5-(2-fluorophenyl)-1H-pyrazole-3-carboxylic acid

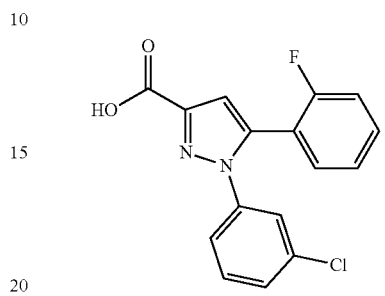

2.30 g (6.67 mmol) of the compound of Example 36A are provided in 32 ml of a 2:1 mixture of 1,4-dioxane and water, 17 ml (33.4 mmol) of a 2N solution of lithium hydroxide in water are added, and the mixture is stirred at 50° C. for 2 h. The mixture is concentrated, a 2N aqueous hydrogen chloride solution is subsequently added to the residue until the pH is acidic, the mixture is extracted with ethyl acetate, and the organic phase is dried over sodium sulfate, filtered and concentrated. The residue is stirred in a little of a mixture of petroleum ether and diethyl ether, collected by filtration and dried under high vacuum. 1.58 g (75% of theory) of the title compound are obtained.

$^1$H-NMR (400 MHz, DMSO-d$_6$): δ=13.1 (s, 1H), 7.56-7.40 (m, 5H), 7.34-7.20 (m, 3H), 7.11 (s, 1H).

LC-MS (Method 1): $R_t$=2.35 min; MS (ESIpos): m/z=317 [M+H]$^+$.

Example 87A 1-(4-Fluorophenyl)-5-[3-(trifluoromethyl)phenyl]-1H-pyrazole-3-carboxylic acid

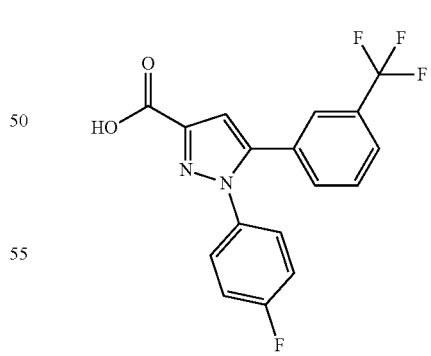

4.50 g (11.9 mmol) of the compound of Example 37A are provided in 107 ml of 1,4-dioxane, 107 ml (214 mmol) of a 2N solution of lithium hydroxide in water are added, and the mixture is stirred at 70° C. for 2 h. The mixture is concentrated, a 2N aqueous hydrogen chloride solution is subsequently added to the residue until the pH is acidic, the mixture is extracted with dichloromethane, and the organic phase is dried over magnesium sulfate, filtered and concentrated. 4.11 g (99% of theory) of the title compound are obtained.

¹H-NMR (400 MHz, DMSO-d₆): δ=13.1 (s, 1H), 7.73 (d, 1H), 7.64-7.54 (m, 3H), 7.46-7.40 (m, 2H), 7.37-7.29 (m, 2H), 7.25 (s, 1H).

LC-MS (Method 4): R$_t$=3.53 min; MS (ESIpos): m/z=351 [M+H]⁺.

Example 88A 1-(3-Chlorophenyl)-5-(2,3-difluorophenyl)-1H-pyrazole-3-carboxylic acid

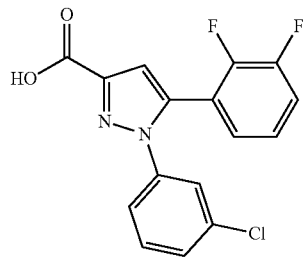 [SMILES: O=C(O)c1cc(-c2cccc(F)c2F)n(-c2cccc(Cl)c2)n1]

0.21 g (0.526 mmol) of the compound of Example 38A are provided in 3.5 ml of methanol and, at room temperature, 295 mg (5.26 mmol) of potassium hydroxide are added. The mixture is heated under reflux for 5 min, a 1N aqueous hydrogen chloride solution is subsequently added until the pH is 5, and the resulting precipitate is collected by suction filtration, washed with diethyl ether and dried under high vacuum. 145 mg (82% of theory) of the title compound are obtained.

¹H-NMR (400 MHz, DMSO-d₆): δ=13.2 (s, 1H), 7.60-7.43 (m, 4H), 7.33-7.19 (m, 3H), 7.18 (s, 1H).

LC-MS (Method 2): R$_t$=2.32 min; MS (ESIpos): m/z=335 [M+H]⁺.

Example 89A 5-(3-Chlorophenyl)-1-(4-chlorophenyl)-1H-pyrazole-3-carboxylic acid

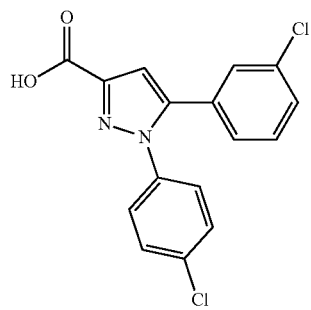 [SMILES: O=C(O)c1cc(-c2cccc(Cl)c2)n(-c2ccc(Cl)cc2)n1]

26.8 g (74.2 mmol) of the compound of Example 39A are provided in 300 ml of 1,4-dioxane, 56 ml (111 mmol) of a 2N solution of lithium hydroxide in water are added, and the mixture is stirred at 70° C. for 2 h. The mixture is concentrated, a 1N aqueous hydrogen chloride solution is subsequently added to the residue until the pH is acidic, the mixture is extracted with dichloromethane, and the combined organic phases are dried over magnesium sulfate, filtered and concentrated. 24.5 g (99% of theory) of the title compound are obtained.

¹H-NMR (400 MHz, DMSO-d₆): δ=13.1 (s, 1H), 7.58-7.52 (m, 2H), 7.48-7.35 (m, 5H), 7.19-7.14 (m, 2H).

LC-MS (Method 6): R$_t$=3.51 min; MS (ESIpos): m/z=333 [M+H]⁺.

Example 90A 5-(3-Fluorophenyl)-1-(4-fluorophenyl)-1H-pyrazole-3-carboxylic acid

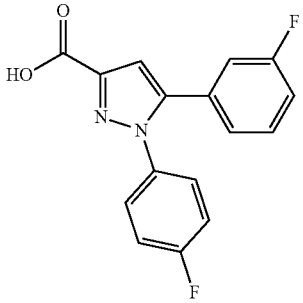 [SMILES: O=C(O)c1cc(-c2cccc(F)c2)n(-c2ccc(F)cc2)n1]

23.9 g (72.8 mmol) of the compound of Example 40A are provided in 100 ml of 1,4-dioxane, 100 ml (200 mmol) of a 2N solution of lithium hydroxide in water are added, and the mixture is stirred at 50° C. for 1 h. The mixture is concentrated, the residue is diluted with water, a conc. aqueous hydrogen chloride solution is subsequently added until the pH is acidic, the mixture is extracted with dichloromethane, and the organic phase is dried over magnesium sulfate, filtered and concentrated. The residue is stirred in a little diethyl ether, collected by filtration and dried under high vacuum. 22.0 g (100% of theory) of the title compound are obtained.

¹H-NMR (400 MHz, DMSO-d₆): δ=7.44-7.37 (m, 3H), 7.36-7.28 (m, 2H), 7.22 (dt, 1H), 7.16 (dt, 1H), 7.12 (s, 1H), 7.05 (d, 1H).

LC-MS (Method 1): R$_t$=2.32 min; MS (ESIpos): m/z=301 [M+H]⁺.

Example 91A 1-(3-Chlorophenyl)-5-(3-fluoro-5-methoxyphenyl)-1H-pyrazole-3-carboxylic acid

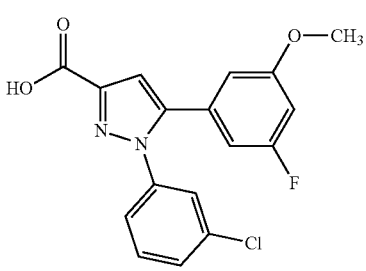 [SMILES: COc1cc(F)cc(-c2cc(C(=O)O)nn2-c2cccc(Cl)c2)c1]

The preparation of the title compound takes place starting from the compound of Example 41A in analogy to the synthesis of the compound of Example 71A. 1.31 g of the title compound are obtained.

¹H-NMR (400 MHz, DMSO-d₆): δ=13.1 (s, 1H), 7.58-7.53 (m, 2H), 7.52-7.46 (m, 1H), 7.30-7.25 (m, 1H), 7.18 (s, 1H), 6.88 (dt, 1H) 6.73-6.69 (m, 2H), 3.70 (s, 3H).

LC-MS (Method 1): R_t=2.37 min; MS (ESIpos): m/z=347 [M+H]⁺.

Example 92A 1-(3-Chloro-4-fluorophenyl)-5-(3-fluoro-5-methoxyphenyl)-1H-pyrazole-3-carboxylic acid

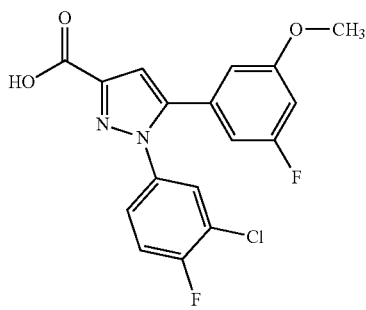 [SMILES: COc1cc(F)cc(-c2cc(C(=O)O)nn2-c2ccc(F)c(Cl)c2)c1]

The preparation of the title compound takes place starting from the compound of Example 42A in analogy to the synthesis of the compound of Example 71A but with stiffing for 6 hours. 1.38 g of the title compound are obtained.

¹H-NMR (400 MHz, DMSO-d₆): δ=13.1 (s, 1H), 7.76 (dd, 1H), 7.54 (t, 1H), 7.35 (ddd, 1H), 7.17 (s, 1H), 6.89 (dt, 1H), 6.74-6.69 (m, 2H), 3.71 (s, 3H).

LC-MS (Method 7): R_t=1.95 min; MS (ESIpos): m/z=365 [M+H]⁺.

Example 93A 1-(3-Chloro-4-fluorophenyl)-5-(3-cyanophenyl)-1H-pyrazole-3-carboxylic acid

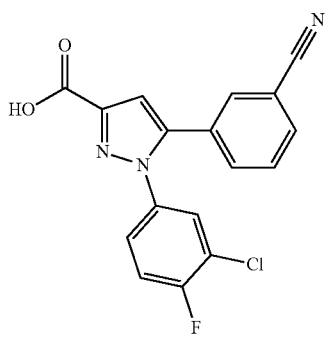 [SMILES: N#Cc1cccc(-c2cc(C(=O)O)nn2-c2ccc(F)c(Cl)c2)c1]

The preparation of the title compound takes place starting from the compound of Example 45A in analogy to the synthesis of the compound of Example 71A. 348 mg (68% of theory) of the title compound are obtained.

¹H-NMR (400 MHz, DMSO-d₆): δ=13.1 (s, 1H), 7.91 (s, 1H), 7.87 (dt, 1H), 7.75 (dd, 1H), 7.61-7.49 (m, 3H), 7.33 (ddd, 1H), 7.24 (s, 1H).

LC-MS (Method 1): R_t=2.21 min; MS (ESIpos): m/z=342 [M+H]⁺.

Example 94A 1-(3-Chloro-4-fluorophenyl)-5-(3-fluorophenyl)-1H-pyrazole-3-carboxylic acid

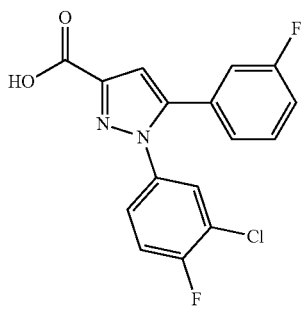 [SMILES: O=C(O)c1cc(-c2cccc(F)c2)n(-c2ccc(F)c(Cl)c2)n1]

The preparation of the title compound takes place starting from the compound of Example 46A in analogy to the synthesis of the compound of Example 71A. 550 mg (99% of theory) of the title compound are obtained.

¹H-NMR (400 MHz, DMSO-d₆): δ=13.1 (s, 1H), 7.73 (dd, 1H), 7.52 (t, 1H), 7.46-7.39 (m, 1H), 7.34 (ddd, 1H), 7.28-7.21 (m, 2H), 7.16 (s, 1H), 7.07 (dt, 1H).

LC-MS (Method 1): R_t=2.36 min; MS (ESIpos): m/z=335 [M+H]⁺.

Example 95A 1-(3-Chloro-4-fluorophenyl)-5-[3-(trifluoromethyl)phenyl]-1H-pyrazole-3-carboxylic acid

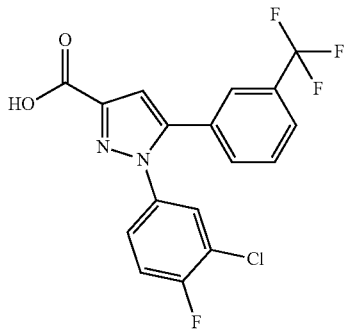 [SMILES: O=C(O)c1cc(-c2cccc(C(F)(F)F)c2)n(-c2ccc(F)c(Cl)c2)n1]

The preparation of the title compound takes place starting from the compound of Example 47A in analogy to the synthesis of the compound of Example 71A. 344 mg (97% of theory) of the title compound are obtained.

¹H-NMR (400 MHz, DMSO-d₆): δ=13.1 (s, 1H), 7.82-7.74 (m, 2H), 7.67-7.50 (m, 4H), 7.36 (ddd, 1H), 7.26 (s, 1H).

LC-MS (Method 1): R_t=2.53 min; MS (ESIpos): m/z=385 [M+H]⁺.

Example 96A 1-(3-Chloro-4-fluorophenyl)-5-[3-fluoro-5-(trifluoromethyl)phenyl]-1H-pyrazole-3-carboxylic acid

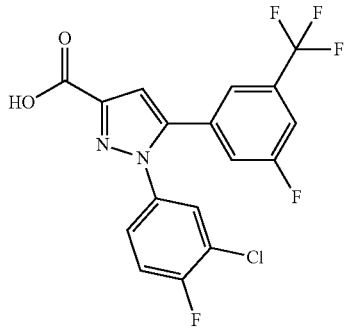 [SMILES: O=C(O)c1cc(-c2cc(F)cc(C(F)(F)F)c2)n(-c2ccc(F)c(Cl)c2)n1]

The preparation of the title compound takes place starting from the compound of Example 48A in analogy to the synthesis of the compound of Example 71A. 851 mg of the title compound with 51% purity are obtained.

LC-MS (Method 1): $R_t$=2.58 min; MS (ESIpos): m/z=403 [M+H]$^+$.

Example 97A 1-(3-Chlorophenyl)-5-[3-fluoro-5-(trifluoromethyl)phenyl]-1H-pyrazole-3-carboxylic acid

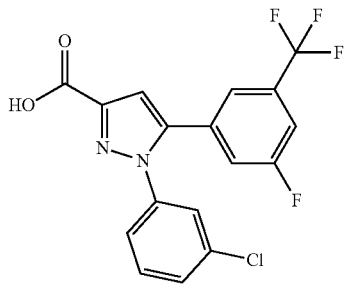 [SMILES: O=C(O)c1cc(-c2cc(F)cc(C(F)(F)F)c2)n(-c2cccc(Cl)c2)n1]

The preparation of the title compound takes place starting from the compound of Example 49A in analogy to the synthesis of the compound of Example 71A. 1.82 g (85% of theory) of the title compound are obtained.

LC-MS (Method 1): $R_t$=2.55 min; MS (ESIpos): m/z=385 [M+H]$^+$.

Example 98A 1-(3-Bromophenyl)-5-(3-chlorophenyl)-1H-pyrazole-3-carboxylic acid

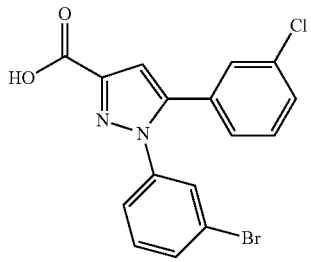 [SMILES: O=C(O)c1cc(-c2cccc(Cl)c2)n(-c2cccc(Br)c2)n1]

The preparation of the title compound takes place starting from the compound of Example 51A in analogy to the synthesis of the compound of Example 71A. 1.74 g of the title compound are obtained.

LC-MS (Method 1): $R_t$=2.47 min; MS (ESIpos): m/z=377 [M+H]$^+$.

Example 99A 1-(3-Bromophenyl)-5-(3-chloro-4-fluorophenyl)-1H-pyrazole-3-carboxylic acid

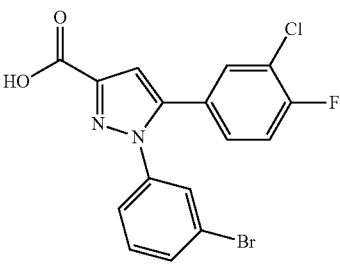 [SMILES: O=C(O)c1cc(-c2ccc(F)c(Cl)c2)n(-c2cccc(Br)c2)n1]

688 mg of the compound of Example 51A with 76% purity (1.23 mmol) are provided in 29 ml of tetrahydrofuran and, at room temperature, 389 mg (16.2 mmol) of lithium hydroxide and 10 ml of water are added. The mixture is stirred at room temperature for 5 h, a 1N aqueous hydrogen chloride solution is subsequently added until the pH is acidic, and the mixture is extracted with ethyl acetate, dried over sodium sulfate, filtered and concentrated. The residue is stirred in a little cyclohexane and the precipitate is collected by suction filtration. 413 mg (83% of theory) of the title compound are obtained.

$^1$H-NMR (400 MHz, DMSO-d$_6$): δ=13.1 (s, 1H), 7.72-7.68 (m, 2H), 7.51 (dt, 1H), 7.42 (t, 1H), 7.33-7.29 (m, 1H), 7.26-7.23 (m, 2H), 7.18 (dt, 1H).

LC-MS (Method 1): $R_t$=2.53 min; MS (ESIpos): m/z=395 [M+H]$^+$.

Example 100A

5-[3-(Benzyloxy)phenyl]-1-(3-chlorophenyl)-1H-pyrazole-3-carboxylic acid

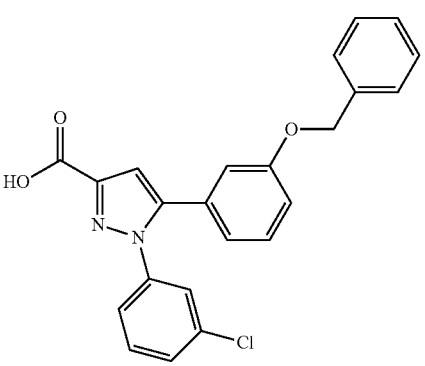 [SMILES: O=C(O)c1cc(-c2cccc(OCc3ccccc3)c2)n(-c2cccc(Cl)c2)n1]

The preparation of the title compound takes place starting from the compound of Example 43A in analogy to the synthesis of the compound of Example 71A. 60.0 g (85% of theory) of the title compound are obtained.

$^1$H-NMR (400 MHz, DMSO-d$_6$): δ=13.1 (s, 1H), 7.55-7.43 (m, 3H), 7.40-7.22 (m, 7H), 7.10 (s, 1H), 7.04 (dd, 1H), 7.00-6.97 (m, 1H), 6.80 (d, 1H), 5.04 (s, 2H).

Example 101A 1-(3-Chloro-4-fluorophenyl)-5-(3-fluoro-5-hydroxyphenyl)-1H-pyrazole-3-carboxylic acid

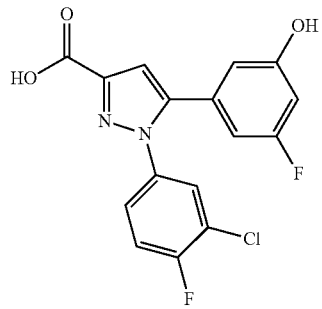 [SMILES: O=C(O)c1cc(-c2cc(O)cc(F)c2)n(-c2ccc(F)c(Cl)c2)n1]

200 mg (0.453 mmol) of the compound of Example 52A are provided in a mixture of 1.5 ml of 1,4-dioxane and 0.9 ml of degassed water under argon, 152 mg (2.72 mmol) of potassium hydroxide, 23.1 mg (0.054 mmol) of 2-di-tert-butylphosphino-2',4',6'-triisopropylbiphenyl and 16.6 mg (0.018 mmol) of tris(dibenzylideneacetone)dipalladium(0) are added, and the mixture is heated at 80° C. overnight. A 1N aqueous hydrogen chloride solution is subsequently added until the pH is acidic, and the reaction mixture is purified by preparative HPLC (RP18 column; mobile phase: acetonitrile/water gradient). 100 mg (63% of theory) of the title compound are obtained.

$^1$H-NMR (400 MHz, DMSO-$d_6$): δ=13.1 (s, 1H), 10.2 (s, 1H), 7.75 (dd, 1H), 7.54 (t, 1H), 7.33 (ddd, 1H), 7.09 (s, 1H), 6.63 (dt, 1H), 6.59 (dt, 1H), 6.44 (t, 1H).

LC-MS (Method 1): $R_t$=2.14 min; MS (ESIpos): m/z=351 [M+H]$^+$.

Example 102A 1-(3-Chloro-4-fluorophenyl)-5-(3-methoxyphenyl)-1H-pyrazole-3-carboxylic acid

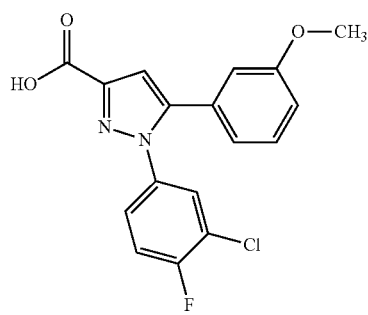 [SMILES: COc1cccc(-c2cc(C(=O)O)nn2-c2ccc(F)c(Cl)c2)c1]

The preparation of the title compound takes place starting from the compound of Example 53A in analogy to the synthesis of the compound of Example 71A. 515 mg (93% of theory) of the title compound are obtained.

$^1$H-NMR (400 MHz, DMSO-$d_6$): δ=13.1 (s, 1H), 7.72 (dd, 1H), 7.52 (t, 1H), 7.35-7.26 (m, 2H), 7.11 (s, 1H), 6.96 (dd, 1H), 6.90 (t, 1H), 6.79 (d, 1H), 3.70 (s, 3H).

LC-MS (Method 1): $R_t$=2.34 min; MS (ESIpos): m/z=347 [M+H]$^+$.

Example 103A

5-[3,5-Bis(trifluoromethyl)phenyl]-1-(3-chlorophenyl)-1H-pyrazole-3-carboxylic acid

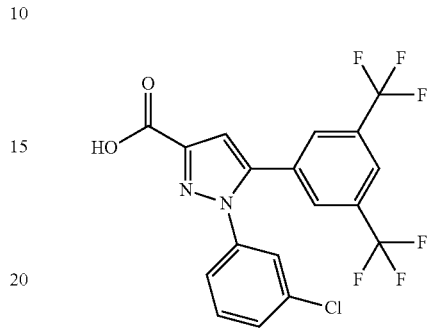

The preparation of the title compound takes place starting from the compound of Example 54A in analogy to the synthesis of the compound of Example 86A. 1.78 g (79% of theory) of the title compound are obtained.

$^1$H-NMR (400 MHz, DMSO-$d_6$): δ=13.1 (s, 1H), 8.15 (s, 1H), 7.96 (s, 2H), 7.62-7.56 (m, 2H), 7.52-7.45 (m, 2H), 7.35-7.30 (m, 1H).

LC-MS (Method 1): $R_t$=2.80 min; MS (ESIpos): m/z=435 [M+H]$^+$.

Example 104A 1-(4-Chlorophenyl)-5-[3-(trifluoromethyl)phenyl]-1H-pyrazole-3-carboxylic acid

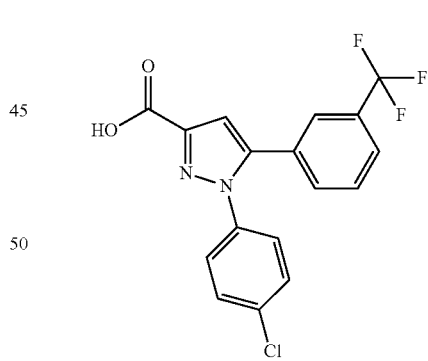

4.75 g (12.0 mmol) of the compound of Example 55A are provided in 108 ml of 1,4-dioxane, 108 ml (216 mmol) of a 2N solution of lithium hydroxide in water are added, and the mixture is stirred at 70° C. for 2 h. The mixture is concentrated, a conc. aqueous hydrogen chloride solution is subsequently added to the residue until the pH is acidic, the mixture is extracted with dichloromethane, and the organic phase is dried over magnesium sulfate, filtered and concentrated. 4.40 g (100% of theory) of the title compound are obtained.

$^1$H-NMR (400 MHz, DMSO-$d_6$): δ=13.1 (s, 1H), 7.75 (d, 1H), 7.65-7.52 (m, 5H), 7.42-7.36 (m, 2H), 7.25 (s, 1H).

Example 105A 1-(4-Chlorophenyl)-5-(3-fluorophenyl)-1H-pyrazole-3-carboxylic acid

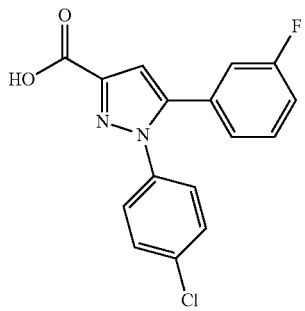 [SMILES: O=C(O)c1cc(-c2cccc(F)c2)n(-c2ccc(Cl)cc2)n1]

43.0 g (125 mmol) of the compound of Example 56A are provided in 504 ml of 1,4-dioxane, 94 ml (188 mmol) of a 2N solution of lithium hydroxide in water are added, and the mixture is stirred at 70° C. for 2 h. The mixture is concentrated, a conc. aqueous hydrogen chloride solution is subsequently added to the residue until the pH is acidic, the mixture is extracted with dichloromethane, and the organic phase is dried over magnesium sulfate, filtered and concentrated. 39.5 g (100% of theory) of the title compound are obtained.

$^1$H-NMR (400 MHz, DMSO-d$_6$): δ=7.56-7.51 (m, 2H), 7.46-7.34 (m, 3H), 7.27-7.16 (m, 2H), 7.10 (s, 1H), 7.06 (d, 1H).

LC-MS (Method 1): R$_t$=2.49 min; MS (ESIpos): m/z=317 [M+H]$^+$.

Example 106A 1-(3-Chloro-4-fluorophenyl)-5-(3-fluoro-5-methylphenyl)-1H-pyrazole-3-carboxylic acid

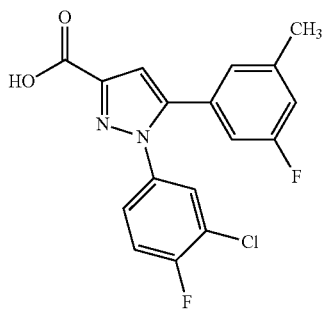 [SMILES: Cc1cc(F)cc(-c2cc(C(=O)O)nn2-c2ccc(F)c(Cl)c2)c1]

The preparation of the title compound takes place starting from the compound of Example 57A in analogy to the synthesis of the compound of Example 71A but with stiffing for 6 hours. 2.34 g of the title compound with 79% purity are obtained.

$^1$H-NMR (400 MHz, DMSO-d$_6$): δ=13.1 (s, 1H), 7.73 (dd, 1H), 7.52 (t, 1H), 7.32 (ddd, 1H), 7.13 (s, 1H), 7.09 (d, 1H), 7.00 (s, 1H), 6.94-6.89 (m, 1H), 2.27 (s, 3H).

LC-MS (Method 1): R$_t$=2.52 min; MS (ESIpos): m/z=349 [M+H]$^+$.

Example 107A 1-(3-Chlorophenyl)-5-(3-fluoro-5-methylphenyl)-1H-pyrazole-3-carboxylic acid

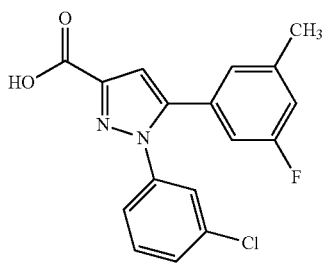 [SMILES: Cc1cc(F)cc(-c2cc(C(=O)O)nn2-c2cccc(Cl)c2)c1]

The preparation of the title compound takes place starting from the compound of Example 58A in analogy to the synthesis of the compound of Example 71A but with stiffing for 6 hours. 1.64 g (100% of theory) of the title compound are obtained.

$^1$H-NMR (400 MHz, DMSO-d$_6$): δ=13.1 (s, 1H), 7.57-7.52 (m, 2H), 7.48 (t, 1H), 7.25 (ddd, 1H), 7.13 (s, 1H), 7.09 (d, 1H), 7.01 (s, 1H), 6.89 (d, 1H), 2.27 (s, 3H).

LC-MS (Method 1): R$_t$=2.49 min; MS (ESIpos): m/z=331 [M+H]$^+$.

Example 108A 5-(3-Chloro-4-fluorophenyl)-1-(3-cyanophenyl)-1H-pyrazole-3-carboxylic acid

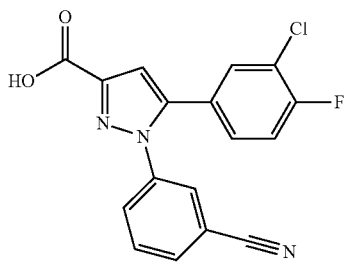 [SMILES: N#Cc1cccc(-n2nc(C(=O)O)cc2-c2ccc(F)c(Cl)c2)c1]

The preparation of the title compound takes place starting from the compound of Example 59A in analogy to the synthesis of the compound of Example 71A. 21 mg of the title compound with 83% purity (64% of theory) are obtained.

$^1$H-NMR (400 MHz, DMSO-d$_6$): δ=13.2 (s, 1H), 7.99-7.95 (m, 2H), 7.70-7.66 (m, 2H), 7.52 (dt, 1H), 7.27 (s, 1H), 7.26-7.23 (m, 1H), 7.20-7.15 (m, 1H).

LC-MS (Method 7): R$_t$=1.78 min; MS (ESIpos): m/z=342 [M+H]$^+$.

Example 109A 5-(3-Chlorophenyl)-1-(3-cyano-4-fluorophenyl)-1H-pyrazole-3-carboxylic acid

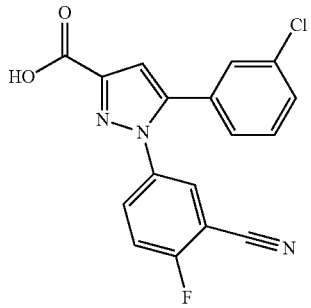 [SMILES: N#Cc1cc(-n2nc(C(=O)O)cc2-c2cccc(Cl)c2)ccc1F]

The preparation of the title compound takes place starting from the compound of Example 60A in analogy to the synthesis of the compound of Example 71A but with stiffing for 6 hours. 672 mg of the title compound with 61% purity are obtained.

LC-MS (Method 7): $R_t$=1.86 min; MS (ESIpos): m/z=342 [M+H]$^+$.

Example 110A 5-(3-Chlorophenyl)-1-(3-cyanophenyl)-1H-pyrazole-3-carboxylic acid

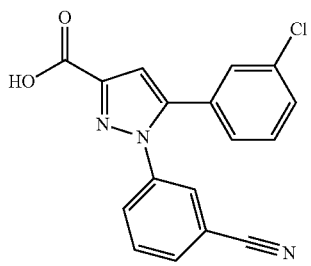 [SMILES: N#Cc1cccc(-n2nc(C(=O)O)cc2-c2cccc(Cl)c2)c1]

The preparation of the title compound takes place starting from the compound of Example 61A in analogy to the synthesis of the compound of Example 71A but with stiffing for 6 hours. 470 mg of the title compound with 77% purity are obtained.

LC-MS (Method 7): $R_t$=1.76 min; MS (ESIpos): m/z=324 [M+H]$^+$.

Example 111A 1,5-Bis(3-cyanophenyl)-1H-pyrazole-3-carboxylic acid

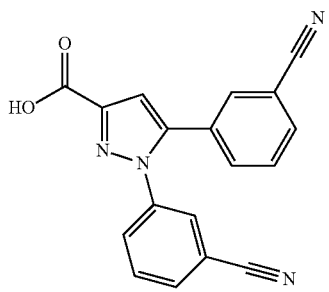 [SMILES: N#Cc1cccc(-c2cc(C(=O)O)nn2-c2cccc(C#N)c2)c1]

The preparation of the title compound takes place starting from the compound of Example 62A in analogy to the synthesis of the compound of Example 71A but with stiffing for 6 hours. 397 mg of the title compound with 36% purity are obtained.

LC-MS (Method 7): $R_t$=1.48 min; MS (ESIpos): m/z=315 [M+H]$^+$.

Example 112A 1-(3-Cyano-4-fluorophenyl)-5-(3-cyanophenyl)-1H-pyrazole-3-carboxylic acid

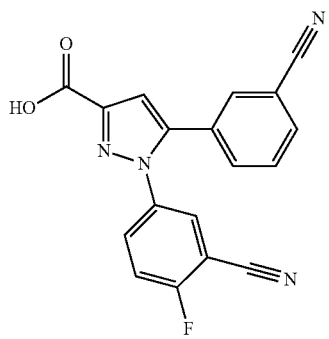 [SMILES: N#Cc1cccc(-c2cc(C(=O)O)nn2-c2ccc(F)c(C#N)c2)c1]

The preparation of the title compound takes place starting from the compound of Example 63A in analogy to the synthesis of the compound of Example 71A but with stiffing for 6 hours. 430 mg of the title compound with 43% purity are obtained.

LC-MS (Method 7): $R_t$=1.58 min; MS (ESIpos): m/z=333 [M+H]$^+$.

Example 113A 5-(3-Chloro-5-fluorophenyl)-1-(3-cyanophenyl)-1H-pyrazole-3-carboxylic acid

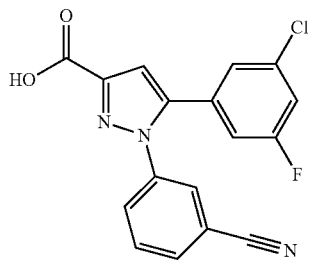 [SMILES: N#Cc1cccc(-n2nc(C(=O)O)cc2-c2cc(F)cc(Cl)c2)c1]

The preparation of the title compound takes place starting from the compound of Example 64A in analogy to the synthesis of the compound of Example 71A but with stiffing for 6 hours. 1.21 g of the title compound with 53% purity are obtained.

LC-MS (Method 7): $R_t$=1.83 min; MS (ESIpos): m/z=342 [M+H]$^+$.

Example 114A 5-(3-Chloro-5-fluorophenyl)-1-(3-cyano-4-fluorophenyl)-1H-pyrazole-3-carboxylic acid

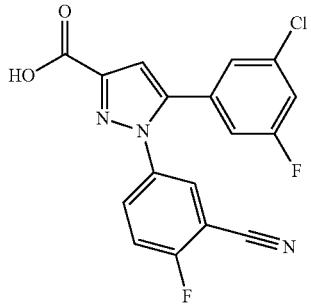 [SMILES: N#Cc1cc(-n2nc(C(=O)O)cc2-c2cc(F)cc(Cl)c2)ccc1F]

The preparation of the title compound takes place starting from the compound of Example 65A in analogy to the synthesis of the compound of Example 71A but with stiffing for 6 hours. 1.88 g of the title compound with 64% purity are obtained.

LC-MS (Method 7): $R_t$=1.91 min; MS (ESIpos): m/z=360 [M+H]$^+$.

Example 115A 1-(3-Chlorophenyl)-5-[3-(2-hydroxyethoxy)phenyl]-1H-pyrazole-3-carboxylic acid

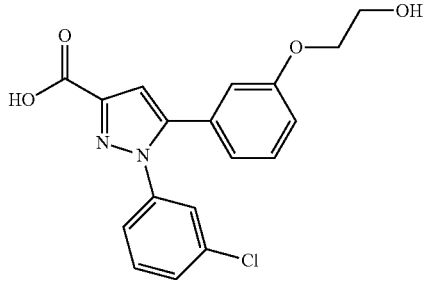 [SMILES: O=C(O)c1cc(-c2cccc(OCCO)c2)n(-c2cccc(Cl)c2)n1]

The preparation of the title compound takes place starting from the compound of Example 66A in analogy to the synthesis of the compound of Example 71A. 11 mg (82% of theory) of the title compound are obtained.

LC-MS (Method 1): $R_t$=1.94 min; MS (ESIpos): m/z=359 [M+H]$^+$.

Example 116A 1-(3-Chlorophenyl)-5-[3-(3-hydroxypropoxy)phenyl]-1H-pyrazole-3-carboxylic acid

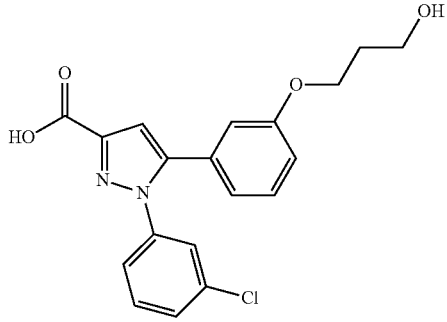 [SMILES: O=C(O)c1cc(-c2cccc(OCCCO)c2)n(-c2cccc(Cl)c2)n1]

The preparation of the title compound takes place starting from the compound of Example 67A in analogy to the synthesis of the compound of Example 71A. 99 mg of the title compound with 65% purity (70% of theory) are obtained.

$^1$H-NMR (400 MHz, DMSO-$d_6$): δ=13.0 (s, 1H), 7.55-7.43 (m, 3H), 7.30-7.23 (m, 2H), 7.10 (s, 1H), 6.94 (dd, 1H), 6.90-6.86 (m, 1H), 6.77 (d, 1H), 4.52 (t, 1H), 3.97 (t, 2H), 3.50 (q, 2H), 1.82-1.74 (m, 2H).

LC-MS (Method 1): $R_t$=2.04 min; MS (ESIpos): m/z=373 [M+H]$^+$.

Example 117A 1-(3-Chlorophenyl)-5-[3-(2-methoxyethoxy)phenyl]-1H-pyrazole-3-carboxylic acid

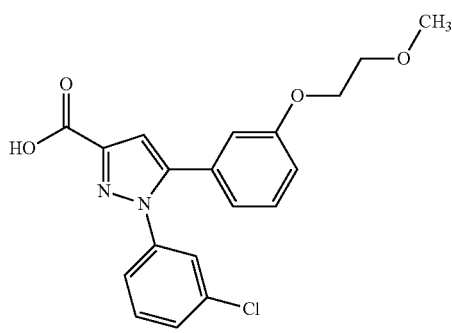 [SMILES: COCCOc1cccc(-c2cc(C(=O)O)nn2-c2cccc(Cl)c2)c1]

The preparation of the title compound takes place starting from the compound of Example 69A in analogy to the synthesis of the compound of Example 71A and with purification by preparative HPLC (RP18 column; mobile phase: acetonitrile/water gradient with the addition of 0.1% formic acid). 46 mg (100% of theory) of the title compound are obtained.

$^1$H-NMR (400 MHz, DMSO-$d_6$): δ=13.0 (s, 1H), 7.55-7.44 (m, 3H), 7.31-7.23 (m, 2H), 7.10 (s, 1H), 6.96 (dd, 1H), 6.91-6.88 (m, 1H), 6.80 (d, 1H), 4.05-4.00 (m, 2H), 3.61-3.54 (m, 2H), 3.28 (s, 3H).

LC-MS (Method 1): $R_t$=2.23 min; MS (ESIpos): m/z=373 [M+H]$^+$.

Example 118A 1-(3-Chlorophenyl)-5-[3-(3-pyrrolidin-1-ylpropoxy)phenyl]-1H-pyrazole-3-carboxylic acid

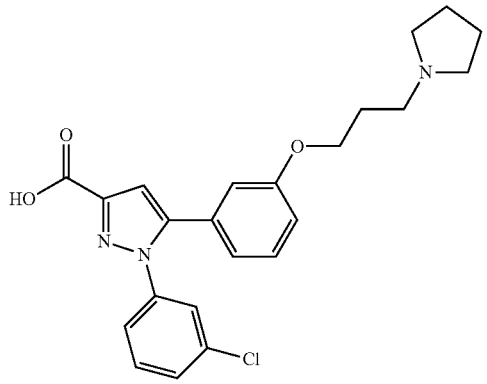 [SMILES: O=C(O)c1cc(-c2cccc(OCCCN3CCCC3)c2)n(-c2cccc(Cl)c2)n1]

The preparation of the title compound takes place starting from the compound of Example 70A in analogy to the synthesis of the compound of Example 71A. 10 mg of the title compound with 79% purity (44% of theory) are obtained.

LC-MS (Method 1): $R_t$=1.44 min; MS (ESIpos): m/z=426 [M+H]$^+$.

Example 119A 1-({5-[3-(2-Chloroethoxy)-5-fluorophenyl]-1-(3-chloro-4-fluorophenyl)-1H-pyrazol-3-yl}carbonyl)imidazolidin-4-one

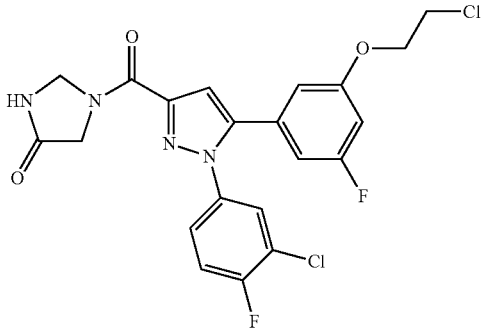 [SMILES: O=C1CN(C(=O)c2cc(-c3cc(F)cc(OCCCl)c3)n(-c3ccc(F)c(Cl)c3)n2)CN1]

1.66 g (4.73 mmol) of the compound of Example 101A, 1.04 g (5.21 mmol) of the compound of Example 125A and 3.69 g (7.10 mmol) of PyBOP are provided in 80 ml of tetrahydrofuran and, at room temperature, 1.73 ml (9.94 mmol) of N,N-diisopropylethylamine are added. The mixture is stirred at room temperature overnight, water is added, the tetrahydrofuran is removed in vacuo, the residue is extracted with ethyl acetate, the organic phase is concentrated and the residue is purified by flash chromatography (mobile phase: ethyl acetate/methanol 200/1). 1.24 g (63% of theory) of 1-{[1-(3-chloro-4-fluorophenyl)-5-(3-fluoro-5-hydroxyphenyl)-1H-pyrazol-3-yl]carbonyl}imidazolidin-4-one are obtained.

LC-MS (Method 7): $R_t$=1.59 min; MS (ESIpos): m/z=419 [M+H]$^+$.

200 mg (0.48 mmol) of 1-{[1-(3-chloro-4-fluorophenyl)-5-(3-fluoro-5-hydroxyphenyl)-1H-pyrazol-3-yl]carbonyl}imidazolidin-4-one are provided in 2.2 ml of tetrahydrofuran and, at room temperature, 48 μl (0.72 mmol) of 2-chloroethanol, 188 mg (0.72 mmol) of triphenylphosphine and 145 mg (0.72 mmol) of diisopropyl azodicarboxylate are added. The reaction mixture is stirred at room temperature overnight and subsequently purified by preparative HPLC (RP18 column; mobile phase: acetonitrile/water gradient). 24 mg (10% of theory) of the title compound are obtained.

$^1$H-NMR (400 MHz, DMSO-d$_6$): δ=8.72 (s, 0.6H), 8.62 (s, 0.4H), 7.80 (dd, 1H), 7.54 (dt, 1H), 7.37 (ddd, 1H), 7.20 (d, 1H), 6.95 (dt, 1H), 6.79 (s, 1H), 6.77-6.71 (m, 1H), 5.32 (s, 0.8H), 4.90 (s, 1.2), 4.44 (s, 1.2H), 4.24 (t, 2H), 3.98 (s, 0.8H), 3.90 (t, 2H).

LC-MS (Method 1): $R_t$=2.40 min; MS (ESIpos): m/z=481 [M+H]$^+$.

Example 120A 3-(3-{1-(3-Chlorophenyl)-3-[(4-oxoimidazolidin-1-yl)carbonyl]-1H-pyrazol-5-yl}phenoxy)propyl methanesulfonate

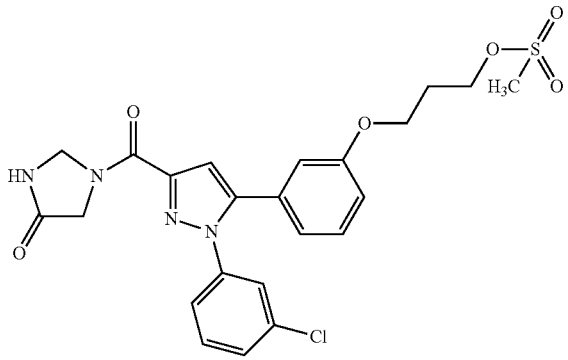 [SMILES: CS(=O)(=O)OCCCOc1cccc(-c2cc(C(=O)N3CNC(=O)C3)nn2-c2cccc(Cl)c2)c1]

3.63 g (8.23 mmol) of the compound of Example 24 are provided in 24 ml of dichloromethane and, at room temperature, 2.2 ml (19.3 mmol) of 2,6-dimethylpyridine and 0.75 ml (9.63 mmol) of methanesulfonyl chloride are added. The mixture is stirred at room temperature overnight, diluted with dichloromethane, washed with water and an aqueous sodium carbonate solution, dried over sodium sulfate and concentrated. 4.33 g of the title compound with 55% purity (56% of theory) are obtained.

LC-MS (Method 1): $R_t$=2.15 min; MS (ESIpos): m/z=519 [M+H]$^+$.

Example 121A 2-(3-{1-(3-Chlorophenyl)-3-[(4-oxoimidazolidin-1-yl)carbonyl]-1H-pyrazol-5-yl}phenoxy)ethyl methanesulfonate

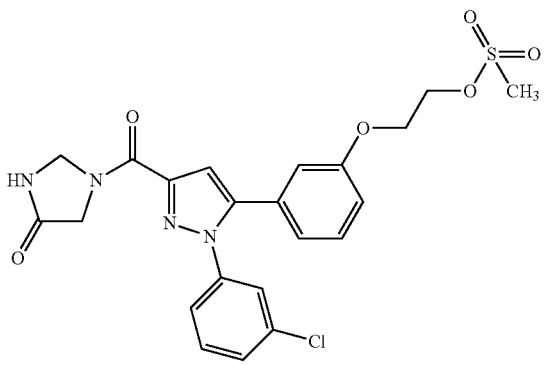 [SMILES: CS(=O)(=O)OCCOc1cccc(-c2cc(C(=O)N3CNC(=O)C3)nn2-c2cccc(Cl)c2)c1]

The preparation of the title compound takes place starting from the compound of Example 23 in analogy to the synthesis of the compound of Example 120A. 6.14 g of the title compound with 51% purity (57% of theory) are obtained.

LC-MS (Method 1): $R_t$=2.08 min; MS (ESIpos): m/z=505 [M+H]$^+$.

Example 122A

N$^2$-Benzylglycinamide

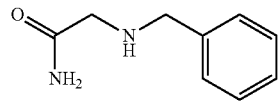 [SMILES: NC(=O)CNCc1ccccc1]

44.2 g (0.40 mol) of glycinamide hydrochloride are provided in 2.21 of dichloromethane at room temperature under argon, 112 ml (0.80 mol) of triethylamine are added and the mixture is stirred at room temperature overnight. 42.5 g (0.40 mol) of benzaldehyde are then added, and the mixture is heated under reflux with a water trap overnight. The mixture is concentrated, the residue is dissolved in 400 ml of tetrahydrofuran/methanol (1:1) and, at 0° C., 16.7 g (0.44 mol) of sodium borohydride are added in portions, and the mixture is stirred at room temperature for 2 days. The suspension is filtered with suction, and the filtrate is concentrated and dried under high vacuum. The residue is stirred in ethyl acetate, the precipitate is filtered off, the filtrate is concentrated, and the residue is stirred in toluene overnight. After the collection of the solid by filtration and subsequent drying under high vacuum 56.5 g (84% of theory) of the title compound are obtained.

$^1$H-NMR (400 MHz, DMSO-d$_6$): δ=7.36-7.28 (m, 4H), 7.27-7.19 (m, 1H), 3.68-3.64 (m, 2H), 3.03-3.00 (m, 2H).

LC-MS (Method 10): R$_t$=0.40 min; MS (ESIpos): m/z=165 [M+H]$^+$.

Example 123A

1-Benzyl-3-(hydroxymethyl)imidazolidin-4-one

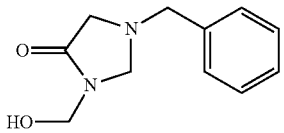 [SMILES: O=C1CN(Cc2ccccc2)CN1CO]

172 ml (6.20 mol) of a 37% formaldehyde solution are added to 56.5 g (0.34 mol) of the compound of Example 122A and the mixture is heated under reflux for 30 minutes. The mixture is extracted with dichloromethane, and the combined organic phases are dried over sodium sulfate, filtered and concentrated. 74.5 g (100% of theory) of the title compound are obtained.

LC-MS (Method 5): R$_t$=0.51 min; MS (ESIpos): m/z=207 [M+H]$^+$.

Example 124A

1-Benzylimidazolidin-4-one trifluoroacetate

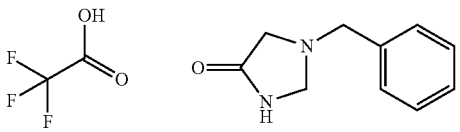 [SMILES: O=C(O)C(F)(F)F ; O=C1CN(Cc2ccccc2)CN1]

74.5 g (0.36 mol) of the compound of Example 123A are heated at 150° C. under high vacuum for 6 h while distilling out volatile reaction products. The residue is purified by HPLC (column: Sunfire C18 5µ, 250×20 mm; eluent: 0.2% trifluoroacetic acid/water-acetonitrile gradient). 28.4 g (27% of theory) of the title compound are obtained.

$^1$H-NMR (400 MHz, DMSO-d$_6$): δ=8.75 (s, 1H), 7.48-7.39 (m, 5H), 4.41 (s, 2H), 4.22 (s, 2H), 3.54 (s, 2H).

LC-MS (Method 10): R$_t$=0.94 min; MS (ESIpos): m/z=177 [M-CF$_3$COOH+H]$^+$.

Example 125A

Imidazolidin-4-one trifluoroacetate

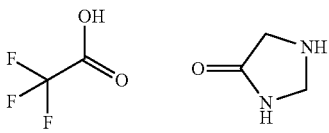 [SMILES: O=C(O)C(F)(F)F ; O=C1CNCN1]

28.4 g (97.9 mmol) of the compound of Example 124A are dissolved in 750 ml of ethanol and, under argon, 4.5 g (42.3 mmol) of palladium on activated carbon (5%) are added. The mixture is stirred under a hydrogen atmosphere at room temperature for 24 h. The suspension is filtered through Celite, concentrated and dried under high vacuum. 19.2 g (98% of theory) of the title compound are obtained.

$^1$H-NMR (400 MHz, DMSO-d$_6$): δ=10.1 (s, 2H), 8.89 (s, 1H), 4.55 (s, 2H), 3.63 (s, 2H).

GC-MS (Method 11): R$_t$=3.92 min MS (EIpos): m/z=86 [M-CF$_3$COOH]$^+$.

Example 126A

3-Acetyl-5-fluorobenzenecarbonitrile

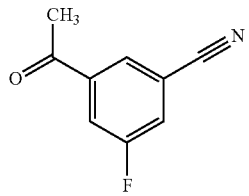

824 mg (0.900 mmol) of tris(dibenzylideneacetone)dipalladium and 1.23 g (1.98 mmol) of rac-1,1'-binaphthalene-2,2'-diylbis(diphenylphosphane) are added to 9.00 g (45.0 mmol) of 3-bromo-5-fluorobenzenecarbonitrile in toluene (300 ml) under an argon atmosphere. After the addition of 19.5 g (54.0 mmol) of (1-ethoxyvinyl)tributylstannane, the mixture is stirred under reflux overnight. The reaction mixture is subsequently concentrated and the residue is taken up in 300 ml of THF. After the addition of 100 ml of an aqueous 2N hydrogen chloride solution the mixture is stirred at room temperature for 2 h. The reaction mixture is subsequently neutralized with a saturated aqueous sodium bicarbonate solution and extracted with ethyl acetate. The combined organic phases are dried over magnesium sulfate, filtered and concentrated in vacuo. The crude product is purified by flash chromatography (mobile phase: cyclohexane/ethyl acetate 9:1). 7.11 g (97% of theory) of the title compound are obtained.

$^1$H-NMR (400 MHz, DMSO-d$_6$): δ=8.28 (t, 1H), 8.18-8.14 (m, 1H), 8.08-8.04 (m, 1H), 2.65 (s, 3H).

GC-MS (Method 11): R$_t$=3.97 min; MS (EIpos): m/z=163 [M]$^+$.

Example 127A

Ethyl 4-(3-cyano-5-fluorophenyl)-2,4-dioxobutyrate

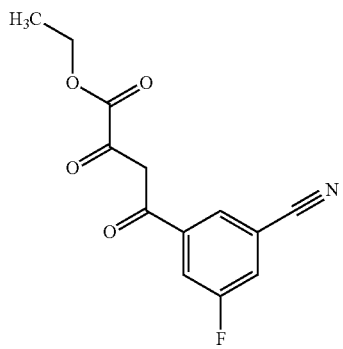 [SMILES: CCOC(=O)C(=O)CC(=O)c1cc(F)cc(C#N)c1]

A solution of 5.00 g (30.6 mmol) of the acetophenone of Example 126A in 50 ml of diethyl ether is added to 42.9 ml (42.9 mmol, 1M in hexane) of lithium bis(trimethylsilyl)amide in 130 ml of diethyl ether at −78° C. and under an argon atmosphere. The mixture is stirred at −78° C. for 1 h and 5.00 ml (36.8 mmol) of diethyl oxalate are subsequently slowly added dropwise. The mixture is slowly warmed to RT and stirred overnight. A 1N aqueous hydrogen chloride solution is slowly added to the resulting suspension, which is then diluted with water and extracted with dichloromethane. The combined organic phases are dried over magnesium sulfate, filtered and concentrated in vacuo. The crude product is suspended in diethyl ether and stirred for 30 min. After filtration and drying under high vacuum 6.50 g (81% of theory) of the title compound are obtained as an approx. 9:1 keto/enol mixture.

LC-MS (Method 12): $R_t$=0.73, 1.04 min; MS (ESIneg): m/z=262 [M−H]⁻.

Example 128A

Ethyl 1-(3-chloro-4-fluorophenyl)-5-(3-cyano-5-fluorophenyl)-1H-pyrazole-3-carboxylate

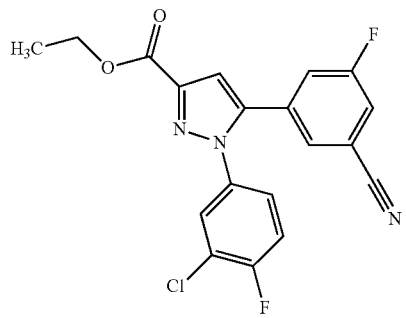 [SMILES: CCOC(=O)c1cc(-c2cc(F)cc(C#N)c2)n(-c2ccc(F)c(Cl)c2)n1]

898 mg (4.56 mmol) of 3-chloro-4-fluorophenylhydrazine hydrochloride are added to 1.00 g (3.80 mmol) of the 1,3-diketo compound of Example 127A in 15 ml of N,N-dimethylacetamide and 0.190 ml of a 10N aqueous hydrogen chloride solution are subsequently added to the resulting solution. The mixture is stirred at RT for 24 h and subsequently purified directly by preparative HPLC (RP18 column; mobile phase: acetonitrile/water gradient). 1.22 g (83% of theory) of the title compound are obtained.

¹H-NMR (400 MHz, DMSO-d₆): δ=7.93 (d, 1H), 7.80 (dd, 1H), 7.72 (s, 1H), 7.58-7.49 (m, 2H), 7.41-7.33 (m, 2H), 4.35 (q, 2H), 1.32 (t, 3H).

LC-MS (Method 5): $R_t$=1.37 min; MS (ESIpos): m/z=388 [M+H]⁺.

Example 129A 1-(3-Chloro-4-fluorophenyl)-5-(3-cyano-5-fluorophenyl)-1H-pyrazole-3-carboxylic acid

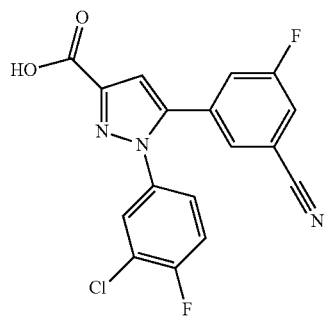 [SMILES: N#Cc1cc(F)cc(-c2cc(C(=O)O)nn2-c2ccc(F)c(Cl)c2)c1]

12.0 ml of water and 741 mg (30.1 mmol) of lithium hydroxide are added to 1.20 g (3.10 mmol) of the carboxylic ester of Example 128A in 36.0 ml of THF. The mixture is stirred at RT for 6 h and a 1N aqueous hydrogen chloride solution is subsequently added to the reaction solution. The mixture is extracted with dichloromethane and the combined organic phases are dried over magnesium sulfate, filtered and concentrated in vacuo. 1.10 g (95% of theory) of the title compound are obtained.

¹H-NMR (400 MHz, DMSO-d₆): δ=13.2 (s, 1H), 7.97-7.88 (m, 1H), 7.78 (dd, 1H), 7.71 (s, 1H), 7.59-7.46 (m, 2H), 7.35 (ddd, 1H), 7.29 (s, 1H).

LC-MS (Method 5): $R_t$=1.15 min; MS (ESIpos): m/z=360 [M+H]⁺.

Example 130A

Ethyl 1-(3-chlorophenyl)-5-(3-cyano-5-fluorophenyl)-1H-pyrazole-3-carboxylate

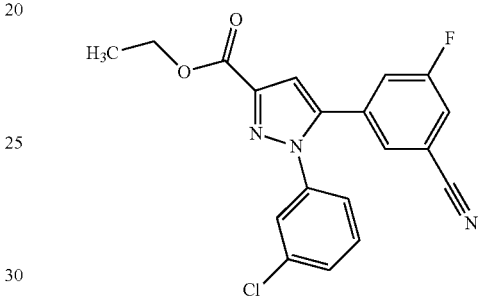

1.87 g (6.28 mmol) of 3-chlorophenylhydrazine hydrochloride with 60% purity are added to 1.30 g (4.83 mmol) of the 1,3-diketo compound of Example 127A in 50 ml of ethanol and the mixture is subsequently stirred at RT for 2 h. 40 ml of conc. acetic acid are thereafter added to the reaction solution and the mixture is stirred at RT for 2 h and then at 60° C. for 1 h. A 1N aqueous 1N hydrogen chloride solution is added to the mixture, which is then extracted with dichloromethane. The combined organic phases are dried over magnesium sulfate, filtered and concentrated in vacuo. The residue is purified by flash chromatography (mobile phase: cyclohexane/ethyl acetate 20:1→1:1). 1.16 g (65% of theory) of the title compound are obtained.

¹H-NMR (400 MHz, DMSO-d₆): δ=7.93 (d, 1H), 7.70 (s, 1H), 7.63-7.56 (m, 2H), 7.57-7.41 (m, 2H), 7.37 (s, 1H), 7.28 (d, 1H), 4.35 (q, 2H), 1.33 (t, 3H).

LC-MS (Method 10): $R_t$=2.51 min; MS (ESIpos): m/z=370 [M+H]⁺.

Example 131A 1-(3-Chlorophenyl)-5-(3-cyano-5-fluorophenyl)-1H-pyrazole-3-carboxylic acid

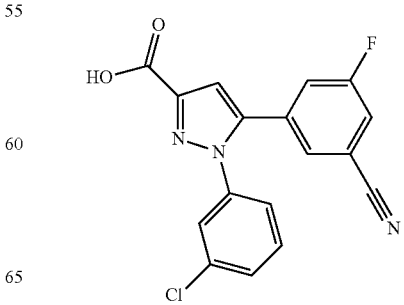

20.0 ml of water and 453 mg (18.9 mmol) of lithium hydroxide are added to 700 mg (1.89 mmol) of the carboxylic ester of Example 130A in 60.0 ml of THF. The mixture is stirred at RT overnight and a 1N aqueous hydrogen chloride solution is subsequently added to the reaction solution. The mixture is extracted with dichloromethane, and the combined organic phases are dried over magnesium sulfate, filtered and concentrated in vacuo. The crude product is purified by preparative HPLC (RP18 column; mobile phase: acetonitrile/water gradient). 712 mg (89% of theory) of the title compound are obtained in 81% purity.

LC-MS (Method 10): $R_t$=2.11 min; MS (ESIpos): m/z=342 [M+H]$^+$.

Example 132A

Ethyl 1-(3-cyano-4-fluorophenyl)-5-(3-cyano-5-fluorophenyl)-1H-pyrazole-3-carboxylate

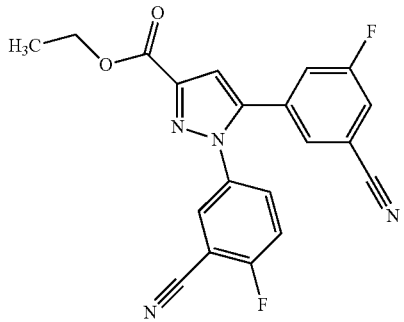 [SMILES: CCOC(=O)c1cc(-c2cc(F)cc(C#N)c2)n(-c2ccc(F)c(C#N)c2)n1]

1.96 g (3.65 mmol) of 2-fluoro-5-hydrazinylbenzenecarbonitrile with 35% purity are added to 800 mg (3.04 mmol) of the 1,3-diketo compound of Example 127A in 12 ml of N,N-dimethylacetamide and 0.152 ml of a 10N aqueous hydrogen chloride solution are subsequently added to the resulting solution. The mixture is stirred at RT for 20 h and subsequently purified directly by preparative HPLC (RP18 column; mobile phase: acetonitrile/water gradient). 931 mg (61% of theory) of the title compound with 75% purity are obtained.

LC-MS (Method 5): $R_t$=1.25 min; MS (ESIpos): m/z=379 [M+H]$^+$.

Example 133A 1-(3-Cyano-4-fluorophenyl)-5-(3-cyano-5-fluorophenyl)-1H-pyrazole-3-carboxylic acid

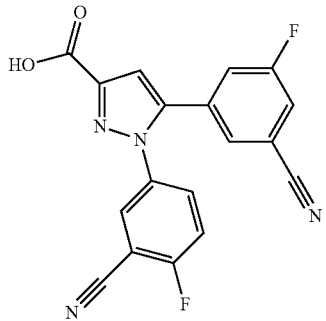 [SMILES: N#Cc1cc(F)cc(-c2cc(C(=O)O)nn2-c2ccc(F)c(C#N)c2)c1]

10.0 ml of water and 570 mg (23.8 mmol) of lithium hydroxide are added to 900 mg (1.78 mmol) of the carboxylic ester of Example 132A with 75% purity in 30.0 ml of THF. The mixture is stirred at RT for 5 h and a 1N aqueous hydrogen chloride solution is subsequently added to the reaction solution. The mixture is extracted with dichloromethane, and the combined organic phases are dried over magnesium sulfate, filtered and concentrated in vacuo. The crude product is purified by preparative HPLC (RP18 column; mobile phase: acetonitrile/water gradient). 527 mg (86% of theory) of the title compound are obtained.

$^1$H-NMR (400 MHz, DMSO-d$_6$): δ=8.09 (br. s., 1H), 7.93 (d, 1H), 7.81-7.69 (m, 2H), 7.69-7.60 (m, 1H), 7.55 (d, 1H), 7.28 (br. s., 1H).

LC-MS (Method 5): $R_t$=1.03 min; MS (ESIpos): m/z=351 [M+H]$^+$.

Example 134A

Ethyl 5-(3-cyano-5-fluorophenyl)-1-(3-cyanophenyl)-1H-pyrazole-3-carboxylate

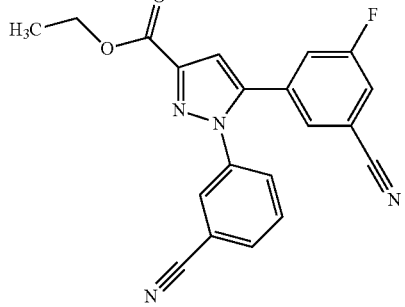

985 mg (4.56 mmol) of 3-hydrazinylbenzonitrile with 79% purity are added to 1.00 g (3.80 mmol) of the 1,3-diketo compound of Example 127A in 20 ml of N,N-dimethylacetamide and 0.190 ml of a 10N aqueous hydrogen chloride solution are subsequently added to the resulting solution. The mixture is stirred at RT for 20 h and subsequently purified directly by preparative HPLC (RP18 column; mobile phase: acetonitrile/water gradient). 1.22 g (80% of theory) of the title compound with 90% purity are obtained.

LC-MS (Method 7): $R_t$=2.04 min; MS (ESIpos): m/z=361 [M+H]$^+$.

Example 135A 5-(3-Cyano-5-fluorophenyl)-1-(3-cyanophenyl)-1H-pyrazole-3-carboxylic acid

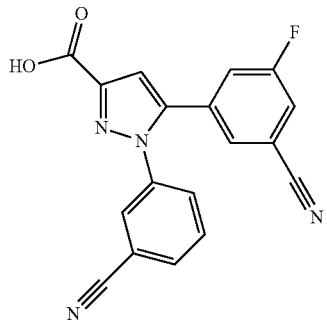 [SMILES: N#Cc1cc(F)cc(-c2cc(C(=O)O)nn2-c2cccc(C#N)c2)c1]

15.0 ml of water and 797 mg of lithium hydroxide (33.3 mmol) are added to 1.20 g (3.00 mmol) of the carboxylic ester of Example 134A with 90% purity in 45.0 ml of THF. The mixture is stirred at RT for 5 h and a 1N aqueous hydrogen chloride solution is subsequently added to the reaction solution. The mixture is extracted with dichloromethane and the combined organic phases are dried over magnesium sulfate, filtered and concentrated in vacuo. The crude product is purified by preparative HPLC (RP18 column; mobile phase: acetonitrile/water gradient). 821 mg (82% of theory) of the title compound are obtained.

$^1$H-NMR (400 MHz, DMSO-$d_6$): δ=13.23 (br. s., 1H), 8.01-7.88 (m, 3H), 7.73-7.63 (m, 3H), 7.55 (d, 1H), 7.32 (s, 1H).

LC-MS (Method 7): $R_t$=1.57 min; MS (ESIpos): m/z=332 [M+H]$^+$.

Exemplary Embodiments

Example 1

1-{[1-(3-Chloro-4-fluorophenyl)-5-(3-chloro-5-fluorophenyl)-1H-pyrazol-3-yl]carbonyl}imidazolidin-4-one

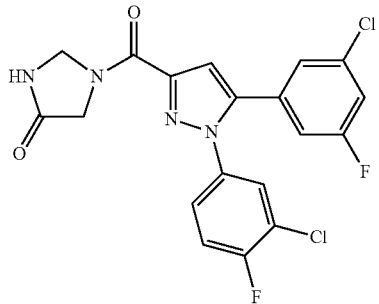 [SMILES: O=C1CN(C(=O)c2cc(-c3cc(F)cc(Cl)c3)n(-c3ccc(F)c(Cl)c3)n2)CN1]

50.0 mg (0.14 mmol) of the compound of Example 71A, 12.8 mg (0.15 mmol) of imidazolidin-4-one and 106 mg (0.20 mmol) of PyBOP are provided in 2.5 ml of tetrahydrofuran and, at room temperature, 50 μl (0.28 mmol) of N,N-diisopropylethylamine are added. The reaction mixture is stirred at room temperature overnight and subsequently purified by preparative HPLC (RP18 column; mobile phase: acetonitrile/water gradient). 49.0 mg (83% of theory) of the title compound are obtained.

$^1$H-NMR (400 MHz, DMSO-$d_6$): δ=8.73 (s, 0.6H), 8.63 (s, 0.4H), 7.85-7.81 (m, 1H), 7.58-7.51 (m, 2H), 7.41-7.34 (m, 1H), 7.29-7.26 (m, 2H), 7.22-7.17 (m, 1H), 5.32 (s, 0.8H), 4.90 (s, 1.2H), 4.43 (s, 1.2H), 3.98 (s, 0.8H).

LC-MS (Method 7): $R_t$=1.94 min; MS (ESIpos): m/z=437 [M+H]$^+$.

Example 2

1-{[5-(3-Chloro-5-fluorophenyl)-1-(3-chlorophenyl)-1H-pyrazol-3-yl]carbonyl}imidazolidin-4-one

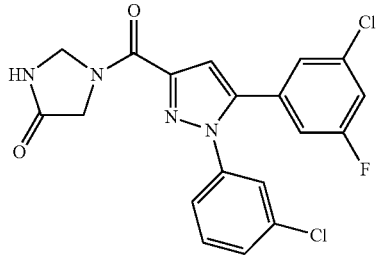 [SMILES: O=C1CN(C(=O)c2cc(-c3cc(F)cc(Cl)c3)n(-c3cccc(Cl)c3)n2)CN1]

The preparation of the title compound takes place starting from the compound of Example 72A in analogy to the synthesis of the compound of Example 1. 50 mg (84% of theory) of the title compound are obtained.

$^1$H-NMR (400 MHz, DMSO-$d_6$): δ=8.73 (s, 0.6H), 8.63 (s, 0.4H), 7.63-7.61 (m, 1H), 7.59-7.55 (m, 1H), 7.55-7.47 (m, 2H), 7.33-7.29 (m, 1H), 7.29-7.26 (m, 1H), 7.26-7.24 (m, 1H), 7.21-7.16 (m, 1H), 5.32 (s, 0.8H), 4.90 (s, 1.2H), 4.44 (s, 1.2H), 3.98 (s, 0.8H).

LC-MS (Method 7): $R_t$=1.90 min; MS (ESIpos): m/z=419 [M+H]$^+$.

Example 3

1-{[1-(3-Chlorophenyl)-5-(3,5-difluorophenyl)-1H-pyrazol-3-yl]carbonyl}imidazolidin-4-one

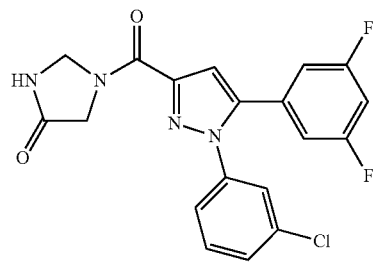 [SMILES: O=C1CN(C(=O)c2cc(-c3cc(F)cc(F)c3)n(-c3cccc(Cl)c3)n2)CN1]

The preparation of the title compound takes place starting from the compound of Example 73A in analogy to the synthesis of the compound of Example 1. 28 mg (73% of theory) of the title compound are obtained.

$^1$H-NMR (400 MHz, DMSO-$d_6$): δ=8.73 (s, 0.6H), 8.62 (s, 0.4H), 7.61 (t, 1H), 7.59-7.54 (m, 1H), 7.53-7.47 (m, 1H), 7.38-7.27 (m, 2H), 7.27-7.25 (m, 1H), 7.10-7.04 (m, 2H), 5.33 (s, 0.8H), 4.90 (s, 1.2H), 4.44 (s, 1.2H), 3.98 (s, 0.8H).

LC-MS (Method 5): $R_t$=1.15 min; MS (ESIpos): m/z=403 [M+H]$^+$.

Example 4

1-{[1,5-Bis(3-chlorophenyl)-1H-pyrazol-3-yl]carbonyl}imidazolidin-4-one

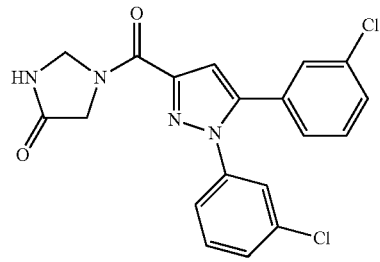 [SMILES: O=C1CN(C(=O)c2cc(-c3cccc(Cl)c3)n(-c3cccc(Cl)c3)n2)CN1]

The preparation of the title compound takes place starting from the compound of Example 74A in analogy to the synthesis of the compound of Example 1. 110 mg (91% of theory) of the title compound are obtained.

$^1$H-NMR (400 MHz, DMSO-$d_6$): δ=8.72 (s, 0.6H), 8.62 (s, 0.4H), 7.58 (t, 1H), 7.56-7.52 (m, 1H), 7.51-7.39 (m, 4H), 7.31-7.25 (m, 1H), 7.22-7.18 (m, 2H), 5.34 (s, 0.8H), 4.91 (s, 1.2H), 4.45 (s, 1.2H), 3.98 (s, 0.8H).

LC-MS (Method 9): $R_t$=2.03 min; MS (ESIpos): m/z=401 [M+H]$^+$.

Example 5

1-{[1,5-Bis(3-chloro-4-fluorophenyl)-1H-pyrazol-3-yl]carbonyl}imidazolidin-4-one

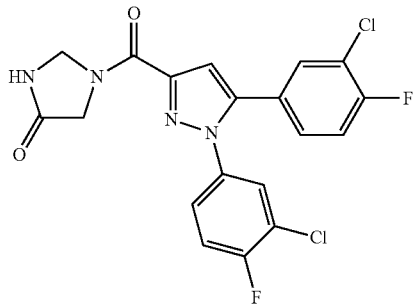 [SMILES: O=C1CN(C(=O)c2cc(-c3ccc(F)c(Cl)c3)n(-c3ccc(F)c(Cl)c3)n2)CN1]

The preparation of the title compound takes place starting from the compound of Example 75A in analogy to the synthesis of the compound of Example 1. 23 mg (39% of theory) of the title compound are obtained.

$^1$H-NMR (400 MHz, DMSO-d$_6$): δ=8.73 (s, 0.6H), 8.63 (s, 0.4H), 7.82 (dd, 1H), 7.68 (dt, 1H), 7.53 (dt, 1H), 7.45 (t, 1H), 7.38-7.32 (m, 1H), 7.25-7.19 (m, 2H), 5.33 (s, 0.8H), 4.90 (s, 1.2H), 4.44 (s, 1.2H), 3.98 (s, 0.8H).

LC-MS (Method 7): $R_t$=1.93 min; MS (ESIpos): m/z=437 [M+H]$^+$.

Example 6

1-({1-(3-Chlorophenyl)-5-[3-(trifluoromethoxy)phenyl]-1H-pyrazol-3-yl}carbonyl)imidazolidin-4-one

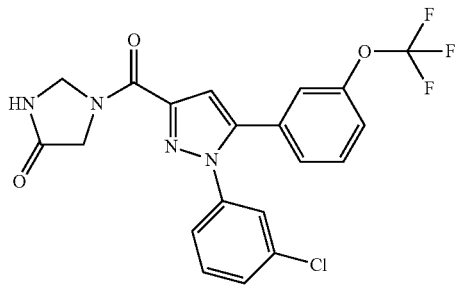 [SMILES: O=C1CN(C(=O)c2cc(-c3cccc(OC(F)(F)F)c3)n(-c3cccc(Cl)c3)n2)CN1]

The preparation of the title compound takes place starting from the compound of Example 76A in analogy to the synthesis of the compound of Example 1. 24 mg (64% of theory) of the title compound are obtained.

$^1$H-NMR (400 MHz, DMSO-d$_6$): δ=8.72 (s, 0.6H), 8.63 (s, 0.4H), 7.60-7.53 (m, 3H), 7.52-7.46 (m, 1H), 7.45-7.40 (m, 2H), 7.34-7.27 (m, 1H), 7.24-7.22 (m, 1H), 7.21-7.18 (m, 1H) 5.34 (s, 0.8H), 4.91 (s, 1.2H), 4.45 (s, 1.2H), 3.99 (s, 0.8H).

LC-MS (Method 7): $R_t$=1.97 min; MS (ESIpos): m/z=451 [M+H]$^+$.

Example 7

1-({1-(3-Chlorophenyl)-5-[4-fluoro-3-(trifluoromethyl)phenyl]-1H-pyrazol-3-yl}carbonyl)imidazolidin-4-one

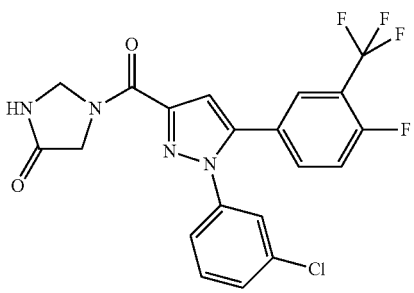 [SMILES: O=C1CN(C(=O)c2cc(-c3ccc(F)c(C(F)(F)F)c3)n(-c3cccc(Cl)c3)n2)CN1]

The preparation of the title compound takes place starting from the compound of Example 77A in analogy to the synthesis of the compound of Example 1. 28 mg (74% of theory) of the title compound are obtained.

$^1$H-NMR (400 MHz, DMSO-d$_6$): δ=8.73 (s, 0.6H), 0.4H), 7.77 (ddd, 1H), 7.65-7.55 (m, 3H), 7.53-7.46 (m, 1H), 7.44-7.40 (m, 1H), 7.38-7.36 (m, 1H), 7.35-7.29 (m, 1H), 5.33 (s, 0.8H), 4.91 (s, 1.2H), 4.45 (s, 1.2H), 3.99 (s, 0.8H).

LC-MS (Method 5): $R_t$=1.25 min; MS (ESIpos): m/z=453 [M+H]$^+$.

Example 8

1-({1-(3-Chloro-4-fluorophenyl)-5-[3-(trifluoromethoxy)phenyl]-1H-pyrazol-3-yl}carbonyl)imidazolidin-4-one

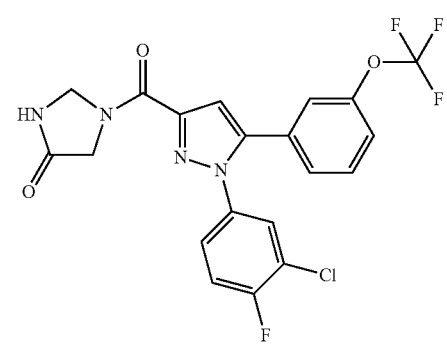 [SMILES: O=C1CN(C(=O)c2cc(-c3cccc(OC(F)(F)F)c3)n(-c3ccc(F)c(Cl)c3)n2)CN1]

The preparation of the title compound takes place starting from the compound of Example 78A in analogy to the synthesis of the compound of Example 1. 53 mg (91% of theory) of the title compound are obtained.

$^1$H-NMR (400 MHz, DMSO-d$_6$): δ=8.73 (s, 0.6H), 8.63 (s, 0.4H), 7.78-7.74 (m, 1H), 7.60-7.51 (m, 2H), 7.45-7.35 (m, 3H), 7.24-7.19 (m, 2H), 5.33 (s, 0.8H), 4.91 (s, 1.2H), 4.44 (s, 1.2H), 3.99 (s, 0.8H).

Example 9

1-{[5-(3-Chloro-4-fluorophenyl)-1-(3-chlorophenyl)-1H-pyrazol-3-yl]carbonyl}imidazolidin-4-one

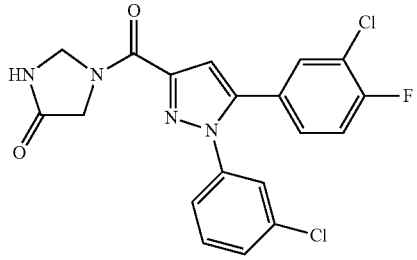

The preparation of the title compound takes place starting from the compound of Example 79A in analogy to the synthesis of the compound of Example 1. 52 mg (87% of theory) of the title compound are obtained.

$^1$H-NMR (400 MHz, DMSO-d$_6$): δ=8.73 (s, 0.6H), 8.62 (s, 0.4H), 7.67-7.63 (m, 1H), 7.61 (t, 1H), 7.57-7.52 (m, 1H), 7.51-7.41 (m, 2H), 7.30-7.21 (m, 2H), 7.21-7.19 (m, 1H), 5.33 (s, 0.8H), 4.91 (s, 1.2H), 4.45 (s, 1.2H), 3.98 (s, 0.8H).

LC-MS (Method 7): R$_t$=1.89 min; MS (ESIpos): m/z=419 [M+H]$^+$.

Example 10

1-{[5-(3-Fluorophenyl)-1-(3-methoxyphenyl)-1H-pyrazol-3-yl]carbonyl}imidazolidin-4-one

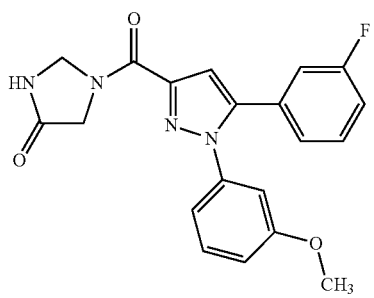 [SMILES: COc1cccc(-n2nc(C(=O)N3CNC(=O)C3)cc2-c2cccc(F)c2)c1]

The preparation of the title compound takes place starting from the compound of Example 80A in analogy to the synthesis of the compound of Example 1. 27 mg (70% of theory) of the title compound are obtained.

$^1$H-NMR (400 MHz, DMSO-d$_6$): δ=8.71 (s, 0.6H), 8.62 (s, 0.4H), 7.45-7.34 (m, 2H), 7.27-7.15 (m, 3H), 7.09 (d, 1H), 7.06-7.01 (m, 1H), 6.98-6.95 (m, 1H), 6.92-6.86 (m, 1H), 5.33 (s, 0.8H), 4.90 (s, 1.2H), 4.44 (s, 1.2H), 3.98 (s, 0.8H), 3.72 (s, 3H).

LC-MS (Method 7): R$_t$=2.02 min; MS (ESIpos): m/z=469 [M+H]$^+$.

Example 11

1-{[1-(3-Chlorophenyl)-5-(3-methoxyphenyl)-1H-pyrazol-3-yl]carbonyl}imidazolidin-4-one

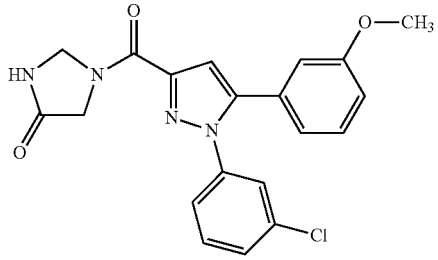 [SMILES: COc1cccc(-c2cc(C(=O)N3CNC(=O)C3)nn2-c2cccc(Cl)c2)c1]

The preparation of the title compound takes place starting from the compound of Example 81A in analogy to the synthesis of the compound of Example 1. 31 mg (84% of theory) of the title compound are obtained.

$^1$H-NMR (400 MHz, DMSO-d$_6$): δ=8.72 (s, 0.6H), 8.62 (s, 0.4H), 7.57-7.44 (m, 3H), 7.33-7.25 (m, 2H), 7.14-7.12 (m, 1H), 7.00-6.95 (m, 1H), 6.91-6.87 (m, 1H), 6.83-6.78 (m, 1H), 5.34 (s, 0.8H), 4.90 (s, 1.2H), 4.46 (s, 1.2H), 3.98 (s, 0.8H), 3.70 (s, 3H).

LC-MS (Method 7): R$_t$=1.63 min; MS (ESIpos): m/z=381 [M+H]$^+$.

Example 12

1-({5-(3-Chlorophenyl)-1-[3-(trifluoromethyl)phenyl]-1H-pyrazol-3-yl}carbonyl)imidazolidin-4-one

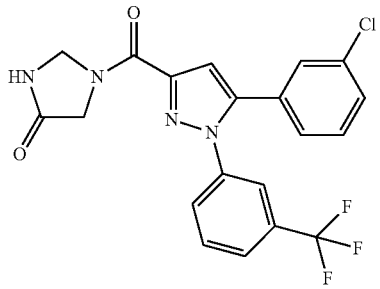 [SMILES: O=C1CN(C(=O)c2cc(-c3cccc(Cl)c3)n(-c3cccc(C(F)(F)F)c3)n2)CN1]

The preparation of the title compound takes place starting from the compound of Example 82A in analogy to the synthesis of the compound of Example 1. 22 mg (58% of theory) of the title compound are obtained.

$^1$H-NMR (400 MHz, DMSO-d$_6$): δ=8.73 (s, 0.6H), 8.64 (s, 0.4H), 7.86-7.81 (m, 1H), 7.76-7.66 (m, 3H), 7.51-7.47 (m, 1H), 7.46-7.38 (m, 2H), 7.24-7.18 (m, 2H), 5.35 (s, 0.8H), 4.91 (s, 1.2H), 4.46 (s, 1.2H), 3.99 (s, 0.8H).

LC-MS (Method 7): R$_t$=1.73 min; MS (ESIpos): m/z=397 [M+H]$^+$.

LC-MS (Method 5): $R_t$=1.23 min; MS (ESIpos): m/z=435 [M+H]$^+$.

Example 13

1-{[1-(3-Chlorophenyl)-5-(3,4-difluorophenyl)-1H-pyrazol-3-yl]carbonyl}imidazolidin-4-one

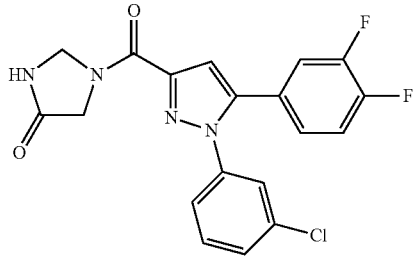 [SMILES: O=C1CN(C(=O)c2cc(-c3ccc(F)c(F)c3)n(-c3cccc(Cl)c3)n2)CN1]

The preparation of the title compound takes place starting from the compound of Example 83A in analogy to the synthesis of the compound of Example 1. 16 mg (41% of theory) of the title compound are obtained.

$^1$H-NMR (400 MHz, DMSO-d$_6$): δ=8.72 (s, 0.6H), 8.62 (s, 0.4H), 7.60 (t, 1H), 7.56-7.44 (m, 4H), 7.30-7.24 (m, 1H), 7.19-7.17 (m, 1H), 7.12-7.06 (m, 1H), 5.34 (s, 0.8H), 4.90 (s, 1.2H), 4.45 (s, 1.2H), 3.98 (s, 0.8H).

LC-MS (Method 5): $R_t$=1.16 min; MS (ESIpos): m/z=403 [M+H]$^+$.

Example 14

1-{[5-(3-Bromo-4-fluorophenyl)-1-(3-chlorophenyl)-1H-pyrazol-3-yl]carbonyl}imidazolidin-4-one

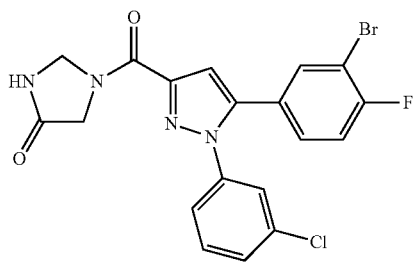

The preparation of the title compound takes place starting from the compound of Example 84A in analogy to the synthesis of the compound of Example 1. 26 mg (70% of theory) of the title compound are obtained.

$^1$H-NMR (400 MHz, DMSO-d$_6$): δ=8.72 (s, 0.6H), 8.62 (s, 0.4H), 7.77-7.72 (m, 1H), 7.60 (t, 1H), 7.57-7.52 (m, 1H), 7.51-7.45 (m, 1H), 7.41 (t, 1H), 7.31-7.24 (m, 2H), 7.21-7.19 (m, 1H), 5.33 (s, 0.8H), 4.90 (s, 1.2H), 4.44 (s, 1.2H), 3.98 (s, 0.8H).

LC-MS (Method 7): $R_t$=1.92 min; MS (ESIpos): m/z=463 [M+H]$^+$.

Example 15

1-{[5-(3-Chlorophenyl)-1-(4-fluorophenyl)-1H-pyrazol-3-yl]carbonyl}imidazolidin-4-one

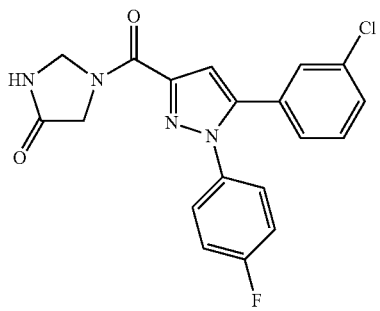 [SMILES: O=C1CN(C(=O)c2cc(-c3cccc(Cl)c3)n(-c3ccc(F)cc3)n2)CN1]

The preparation of the title compound takes place starting from the compound of Example 85A in analogy to the synthesis of the compound of Example 1. 53 mg (42% of theory) of the title compound are obtained.

$^1$H-NMR (400 MHz, DMSO-d$_6$): δ=8.71 (s, 0.6H), 8.63 (s, 0.4H), 7.48-7.31 (m, 7H), 7.20-7.15 (m, 2H), 5.32 (s, 0.8H), 4.90 (s, 1.2H), 4.43 (s, 1.2H), 3.98 (s, 0.8H).

LC-MS (Method 7): $R_t$=1.77 min; MS (ESIpos): m/z=385 [M+H]$^+$.

Example 16

1-{[1-(3-Chlorophenyl)-5-(2-fluorophenyl)-1H-pyrazol-3-yl]carbonyl}imidazolidin-4-one

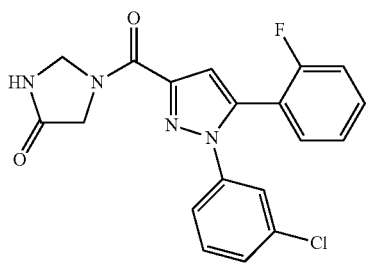 [SMILES: O=C1CN(C(=O)c2cc(-c3ccccc3F)n(-c3cccc(Cl)c3)n2)CN1]

The preparation of the title compound takes place starting from the compound of Example 86A in analogy to the synthesis of the compound of Example 1. 34 mg (88% of theory) of the title compound are obtained.

$^1$H-NMR (400 MHz, DMSO-d$_6$): δ=8.73 (s, 0.6H), 8.64 (s, 0.4H), 7.57-7.40 (m, 5H), 7.35-7.21 (m, 3H), 7.14-7.11 (m, 1H), 5.38 (s, 0.8H), 4.91 (s, 1.2H), 4.49 (s, 1.2H), 3.99 (s, 0.8H).

Example 17

1-({1-(4-Fluorophenyl)-5-[3-(trifluoromethyl)phenyl]-1H-pyrazol-3-yl}carbonyl)imidazolidin-4-one

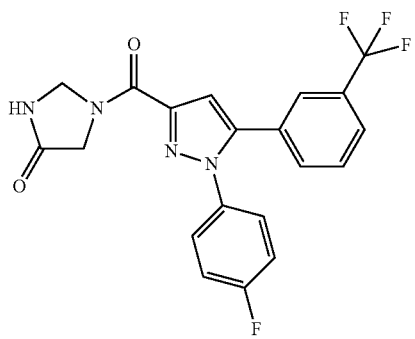 [SMILES: O=C1CN(C(=O)c2cc(-c3cccc(C(F)(F)F)c3)n(-c3ccc(F)cc3)n2)CN1]

The preparation of the title compound takes place starting from the compound of Example 87A in analogy to the synthesis of the compound of Example 1. 28 mg (74% of theory) of the title compound are obtained.

$^1$H-NMR (400 MHz, DMSO-d$_6$): δ=8.72 (s, 0.6H), 8.63 (s, 0.4H), 7.75 (d, 1H), 7.65-7.56 (m, 3H), 7.49-7.43 (m, 2H), 7.37-7.30 (m, 2H), 7.29-7.26 (m, 1H), 5.33 (s, 0.8H), 4.91 (s, 1.2H), 4.44 (s, 1.2H), 3.99 (s, 0.8H).

LC-MS (Method 5): R$_t$=1.17 min; MS (ESIpos): m/z=419 [M+H]$^+$.

Example 18

1-{[1-(3-Chlorophenyl)-5-(2,3-difluorophenyl)-1H-pyrazol-3-yl]carbonyl}imidazolidin-4-one

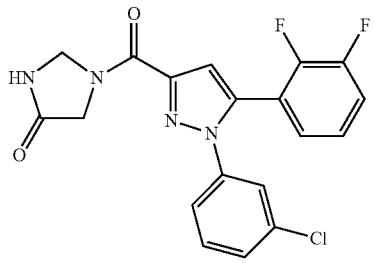 [SMILES: O=C1CN(C(=O)c2cc(-c3cccc(F)c3F)n(-c3cccc(Cl)c3)n2)CN1]

The preparation of the title compound takes place starting from the compound of Example 88A in analogy to the synthesis of the compound of Example 1. 8 mg (100% of theory) of the title compound are obtained.

$^1$H-NMR (400 MHz, DMSO-d$_6$): δ=8.73 (s, 0.6H), 8.64 (s, 0.4H), 7.61-7.43 (m, 4H), 7.35-7.21 (m, 3H), 7.21-7.19 (m, 1H), 5.38 (s, 0.8H), 4.91 (s, 1.2H), 4.49 (s, 1.2H), 3.99 (s, 0.8H).

Example 19

1-{[5-(3-Chlorophenyl)-1-(4-chlorophenyl)-1H-pyrazol-3-yl]carbonyl}imidazolidin-4-one

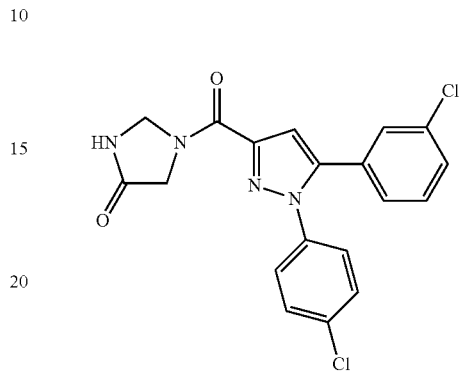

The preparation of the title compound takes place starting from the compound of Example 89A in analogy to the synthesis of the compound of Example 1. 31 mg (80% of theory) of the title compound are obtained.

$^1$H-NMR (400 MHz, DMSO-d$_6$): δ=8.72 (s, 0.6H), 8.65 (s, 0.4H), 7.58-7.53 (m, 2H), 7.50-7.38 (m, 5H), 7.20-7.16 (m, 2H), 5.32 (s, 0.8H), 4.90 (s, 1.2H), 4.43 (s, 1.2H), 3.98 (s, 0.8H).

LC-MS (Method 5): R$_t$=1.22 min; MS (ESIpos): m/z=401 [M+H]$^+$.

Example 20

1-{[5-(3-Fluorophenyl)-1-(4-fluorophenyl)-1H-pyrazol-3-yl]carbonyl}imidazolidin-4-one

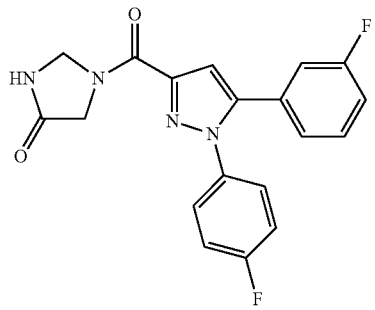 [SMILES: O=C1CN(C(=O)c2cc(-c3cccc(F)c3)n(-c3ccc(F)cc3)n2)CN1]

The preparation of the title compound takes place starting from the compound of Example 90A in analogy to the synthesis of the compound of Example 1. 18 mg (47% of theory) of the title compound are obtained.

$^1$H-NMR (400 MHz, DMSO-d$_6$): δ=8.72 (s, 0.6H), 8.63 (s, 0.4H), 7.48-7.39 (m, 3H), 7.37-7.30 (m, 2H), 7.27-7.16 (m, 3H), 7.08-7.04 (m, 1H), 5.32 (s, 0.8H), 4.90 (s, 1.2H), 4.43 (s, 1.2H), 3.98 (s, 0.8H).

Example 21

1-{[1-(3-Chlorophenyl)-5-(3-fluoro-5-methoxyphenyl)-1H-pyrazol-3-yl]carbonyl}imidazolidin-4-one

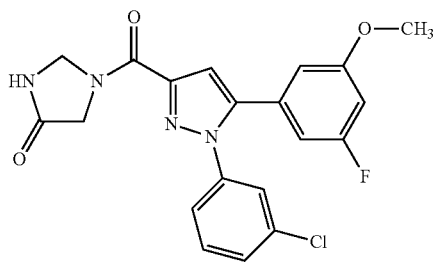 [SMILES: COc1cc(F)cc(-c2cc(C(=O)N3CNC(=O)C3)nn2-c2cccc(Cl)c2)c1]

800 mg (2.31 mmol) of the compound of Example 91A are provided in 19 ml of dry toluene and, at room temperature, 0.48 ml (6.58 mmol) of thionyl chloride are added, and the mixture is heated under reflux for 2.5 h. After cooling, the residue is taken up in 6 ml of dichloromethane, and one eighth of the solution is mixed at 0° C. with 0.13 ml (0.92 mmol) of triethylamine and 92.3 mg (0.46 mmol) of the compound of Example 125A and stirred at RT overnight. The reaction mixture is concentrated, and the residue is purified by preparative HPLC (RP18 column; mobile phase: acetonitrile/water gradient) and by preparative thin-layer chromatography (silica gel; mobile phase: ethyl acetate). 11 mg (9% of theory) of the title compound are obtained.

$^1$H-NMR (400 MHz, DMSO-$d_6$): δ=8.72 (s, 0.6H), 8.61 (s, 0.4H), 7.59 (t, 1H), 7.57-7.53 (m, 1H), 7.53-7.46 (m, 1H), 7.33-7.26 (m, 1H), 7.21-7.19 (m, 1H), 6.90 (dt, 1H), 6.74-6.69 (m, 2H), 5.33 (s, 0.8H), 4.90 (s, 1.2H), 4.44 (s, 1.2H), 3.98 (s, 0.8H), 3.71 (s, 3H).

LC-MS (Method 1): $R_t$=2.23 min; MS (ESIpos): m/z=415 [M+H]$^+$.

Example 22

1-{[1-(3-Chloro-4-fluorophenyl)-5-(3-fluoro-5-methoxyphenyl)-1H-pyrazol-3-yl]carbonyl}imidazolidin-4-one

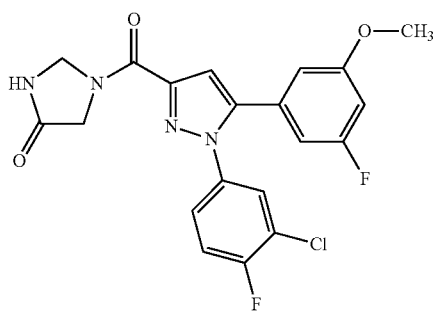 [SMILES: COc1cc(F)cc(-c2cc(C(=O)N3CNC(=O)C3)nn2-c2ccc(F)c(Cl)c2)c1]

The preparation of the title compound takes place starting from the compound of Example 92A in analogy to the synthesis of the compound of Example 21. 29 mg (24% of theory) of the title compound are obtained.

$^1$H-NMR (400 MHz, DMSO-$d_6$): δ=8.72 (s, 0.6H), 8.62 (s, 0.4H), 7.81 (dd, 1H), 7.54 (dt, 1H), 7.40-7.33 (m, 1H), 7.20-7.18 (m, 1H), 6.90 (dt, 1H), 6.75-6.70 (m, 2H), 5.32 (s, 0.8H), 4.90 (s, 1.2H), 4.44 (s, 1.2H), 3.98 (s, 0.8H), 3.72 (s, 3H).

LC-MS (Method 1): $R_t$=2.27 min; MS (ESIpos): m/z=433 [M+H]$^+$.

Example 23

1-({1-(3-Chlorophenyl)-5-[3-(2-hydroxyethoxy)phenyl]-1H-pyrazol-3-yl}carbonyl)imidazolidin-4-one

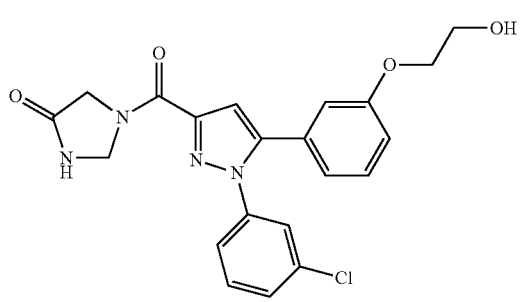 [SMILES: O=C1CN(C(=O)c2cc(-c3cccc(OCCO)c3)n(-c3cccc(Cl)c3)n2)CN1]

11.1 mg (0.031 mmol) of the compound of Example 115A, 6.8 mg (0.034 mmol) of the compound of Example 125A and 24.2 mg (0.046 mmol) of PyBOP are provided in 0.6 ml of tetrahydrofuran and, at room temperature, 11 μl (0.065 mmol) of N,N-diisopropylethylamine are added. The reaction mixture is stirred at room temperature overnight and subsequently purified by preparative HPLC (RP18 column; mobile phase: acetonitrile/water gradient). 3.5 mg (27% of theory) of the title compound are obtained.

$^1$H-NMR (400 MHz, DMSO-$d_6$): δ=8.72 (s, 0.6H), 8.62 (s, 0.4H), 7.57-7.43 (m, 3H), 7.32-7.24 (m, 2H), 7.12-7.10 (m, 1H), 7.00-6.95 (m, 1H), 6.92-6.89 (m, 1H), 6.78 (d, 1H), 5.35 (s, 0.8H), 4.90 (s, 1.2H), 4.85 (t, 1H), 4.46 (s, 1.2H), 3.98 (s, 0.8H), 3.92 (t, 2H), 3.67 (q, 2H).

LC-MS (Method 7): $R_t$=1.38 min; MS (ESIpos): m/z=427 [M+H]$^+$.

Example 24

1-({1-(3-Chlorophenyl)-5-[3-(3-hydroxypropoxy)phenyl]-1H-pyrazol-3-yl}carbonyl)imidazolidin-4-one

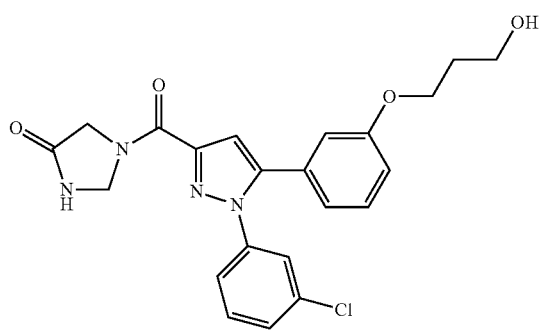 [SMILES: O=C1CN(C(=O)c2cc(-c3cccc(OCCCO)c3)n(-c3cccc(Cl)c3)n2)CN1]

The preparation of the title compound takes place starting from the compound of Example 116A in analogy to the synthesis of the compound of Example 23. 54 mg (69% of theory) of the title compound are obtained.

$^1$H-NMR (400 MHz, DMSO-$d_6$): δ=8.72 (s, 0.6H), 8.62 (s, 0.4H), 7.56-7.44 (m, 3H), 7.31-7.24 (m, 2H), 7.12-7.10 (m, 1H), 6.99-6.94 (m, 1H), 6.91-6.88 (m, 1H), 6.80-6.76 (m, 1H), 5.34 (s, 0.8H), 4.90 (s, 1.2H), 4.52 (t, 1H), 4.46 (s, 1.2H), 4.01-3.95 (m, 2.8H), 3.51 (q, 2H), 1.83-1.75 (m, 2H).

LC-MS (Method 1): $R_t$=1.95 min; MS (ESIpos): m/z=441 [M+H]$^+$.

Example 25

3-{1-(3-Chloro-4-fluorophenyl)-3-[4-oxoimidazolidin-1-yl)carbonyl]-1H-pyrazol-5-yl}benzenecarbonitrile

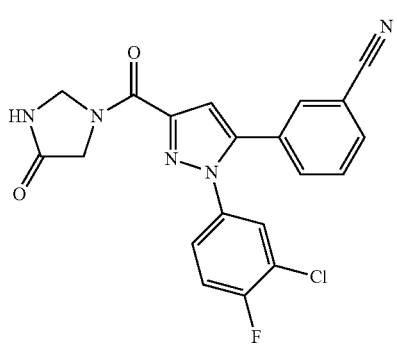 [SMILES: N#Cc1cccc(-c2cc(C(=O)N3CNC(=O)C3)nn2-c2ccc(F)c(Cl)c2)c1]

The preparation of the title compound takes place starting from the compound of Example 93A in analogy to the synthesis of the compound of Example 23. The product is additionally purified by preparative thin-layer chromatography (silica gel; mobile phase: ethyl acetate) and 8 mg (16% of theory) of the title compound are obtained.

$^1$H-NMR (400 MHz, DMSO-$d_6$): δ=8.73 (s, 0.6H), 8.63 (s, 0.4H), 7.95-7.92 (m, 1H), 7.89 (dt, 1H), 7.81 (dd, 1H), 7.59 (t, 1H), 7.56-7.49 (m, 2H), 7.38-7.31 (m, 1H), 7.27-7.25 (m, 1H), 5.34 (s, 0.8H), 4.91 (s, 1.2H), 4.45 (s, 1.2H), 3.99 (s, 0.8H).

LC-MS (Method 7): $R_t$=1.64 min; MS (ESIpos): m/z=410 [M+H]$^+$.

Example 26

1-{[1-(3-Chloro-4-fluorophenyl)-5-(3-fluorophenyl)-1H-pyrazol-3-yl]carbonyl}imidazolidin-4-one

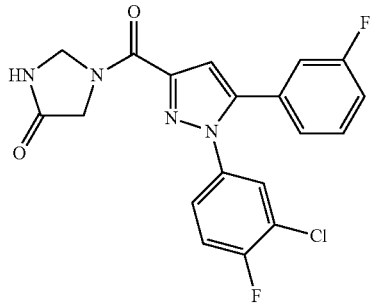 [SMILES: O=C1CN(C(=O)c2cc(-c3cccc(F)c3)n(-c3ccc(F)c(Cl)c3)n2)CN1]

The preparation of the title compound takes place starting from the compound of Example 94A in analogy to the synthesis of the compound of Example 23. The product is additionally purified by preparative thin-layer chromatography (silica gel; mobile phase: ethyl acetate) and 10 mg (16% of theory) of the title compound are obtained.

$^1$H-NMR (400 MHz, DMSO-$d_6$): δ=8.72 (s, 0.6H), 8.63 (s, 0.4H), 7.79 (dd, 1H), 7.55 (dt, 1H), 7.48-7.40 (m, 1H), 7.39-7.32 (m, 1H), 7.30-7.23 (m, 2H), 7.19-7.17 (m, 1H), 7.10-7.05 (m, 1H), 5.33 (s, 0.8H), 4.90 (s, 1.2H), 4.45 (s, 1.2H), 3.98 (s, 0.8H).

LC-MS (Method 7): $R_t$=1.78 min; MS (ESIpos): m/z=403 [M+H]$^+$.

Example 27

1-({1-(3-Chloro-4-fluorophenyl)-5-[3-(trifluoromethyl)phenyl]-1H-pyrazol-3-yl}carbonyl)imidazolidin-4-one

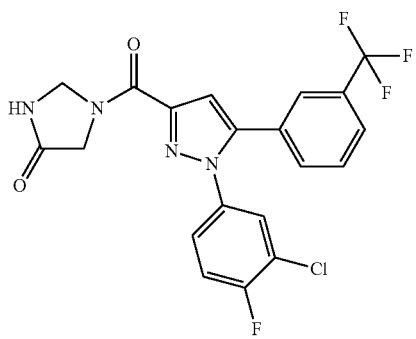 [SMILES: O=C1CN(C(=O)c2cc(-c3cccc(C(F)(F)F)c3)n(-c3ccc(F)c(Cl)c3)n2)CN1]

The preparation of the title compound takes place starting from the compound of Example 95A in analogy to the synthesis of the compound of Example 23. The product is additionally purified by preparative thin-layer chromatography (silica gel; mobile phase: ethyl acetate) and 17 mg (29% of theory) of the title compound are obtained.

$^1$H-NMR (400 MHz, DMSO-$d_6$): δ=8.73 (s, 0.6H), 8.63 (s, 0.4H), 7.83-7.75 (m, 2H), 7.69-7.50 (m, 4H), 7.41-7.34 (m, 1H), 7.30-7.27 (d, 1H), 5.34 (s, 0.8H), 4.91 (s, 1.2H), 4.45 (s, 1.2H), 3.99 (s, 0.8H).

LC-MS (Method 7): $R_t$=1.95 min; MS (ESIpos): m/z=453 [M+H]$^+$.

Example 28

1-({1-(3-Chloro-4-fluorophenyl)-5-[3-fluoro-5-(trifluoromethyl)phenyl]-1H-pyrazol-3-yl}carbonyl)imidazolidin-4-one

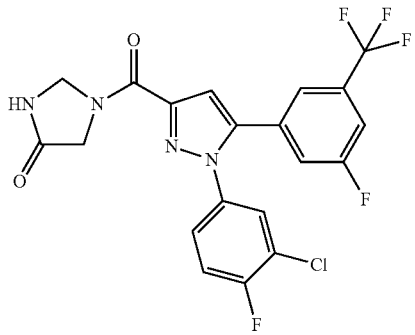 [SMILES: O=C1CN(C(=O)c2cc(-c3cc(F)cc(C(F)(F)F)c3)n(-c3ccc(F)c(Cl)c3)n2)CN1]

The preparation of the title compound takes place starting from the compound of Example 96A in analogy to the synthesis of the compound of Example 23. 17 mg (27% of theory) of the title compound are obtained.

$^1$H-NMR (400 MHz, DMSO-d$_6$): δ=8.73 (s, 0.6H), 8.63 (s, 0.4H), 7.84 (dd, 1H), 7.77 (d, 1H), 7.60 (d, 1H), 7.55 (dt, 1H), 7.46-7.37 (m, 2H), 7.37-7.35 (m, 1H), 5.33 (s, 0.8H), 4.91 (s, 1.2H), 4.44 (s, 1.2H), 3.99 (s, 0.8H).

LC-MS (Method 7): R$_t$=2.01 min; MS (ESIpos): m/z=471 [M+H]$^+$.

Example 29

1-{[1-(3-Chlorophenyl)-5-{3-[3-(dimethylamino)propoxy]phenyl}-1H-pyrazol-3-yl]carbonyl}imidazolidin-4-one formate

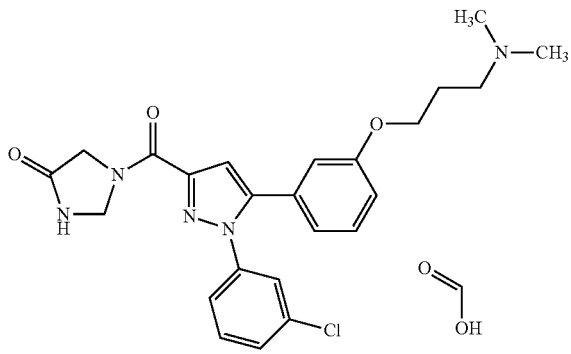 [SMILES: CN(C)CCCOc1cccc(-c2cc(C(=O)N3CNC(=O)C3)nn2-c2cccc(Cl)c2)c1 ; O=CO]

49.6 mg (0.096 mmol) of the compound of Example 120A and 0.48 ml (0.96 mmol) of a 2M solution of dimethylamine in tetrahydrofuran are stirred in 3 ml of ethanol at 80° C. overnight. The reaction mixture is subsequently purified by preparative HPLC (RP18 column; mobile phase: acetonitrile/water gradient with the addition of 0.1% formic acid). 6.2 mg (23% of theory) of the title compound are obtained.

$^1$H-NMR (400 MHz, DMSO-d$_6$): δ=8.72 (s, 0.6H), 8.62 (s, 0.4H), 8.18 (s, 1H), 7.57-7.43 (m, 3H), 7.31-7.24 (m, 2H), 7.13-7.11 (m, 1H), 6.98-6.93 (m, 1H), 6.88-6.86 (m, 1H), 6.80 (d, 1H), 5.34 (s, 0.8H), 4.90 (s, 1.2H), 4.46 (s, 1.2H), 3.98 (s, 0.8H), 3.92 (t, 2H), 2.33 (t, 2H), 2.15 (s, 6H), 1.82-1.74 (m, 2H).

LC-MS (Method 5): R$_t$=0.83 min; MS (ESIpos): m/z=468 [M+H]$^+$.

Example 30

1-({1-(3-Chlorophenyl)-5-[3-fluoro-5-(trifluoromethyl)phenyl]-1H-pyrazol-3-yl}carbonyl)imidazolidin-4-one

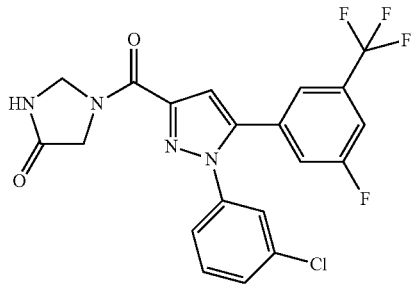 [SMILES: O=C1CN(C(=O)c2cc(-c3cc(F)cc(C(F)(F)F)c3)n(-c3cccc(Cl)c3)n2)CN1]

The preparation of the title compound takes place starting from the compound of Example 97A in analogy to the synthesis of the compound of Example 23 with the addition of 0.1% formic acid in the preparative HPLC. 60 mg (51% of theory) of the title compound are obtained.

$^1$H-NMR (400 MHz, DMSO-d$_6$): δ=8.73 (s, 0.6H), 8.63 (s, 0.4H), 7.77 (d, 1H), 7.64-7.55 (m, 3H), 7.53-7.46 (m, 1H), 7.44-7.40 (m, 1H), 7.39-7.29 (m, 2H), 5.33 (s, 0.8H), 4.91 (s, 1.2H), 4.45 (s, 1.2H), 3.99 (s, 0.8H).

LC-MS (Method 1): R$_t$=2.38 min; MS (ESIpos): m/z=453 [M+H]$^+$.

Example 31

1-({1-(3-Chlorophenyl)-5-[3-(3-pyrrolidin-1-ylpropoxy)phenyl]-1H-pyrazol-3-yl}carbonyl)imidazolidin-4-one formate

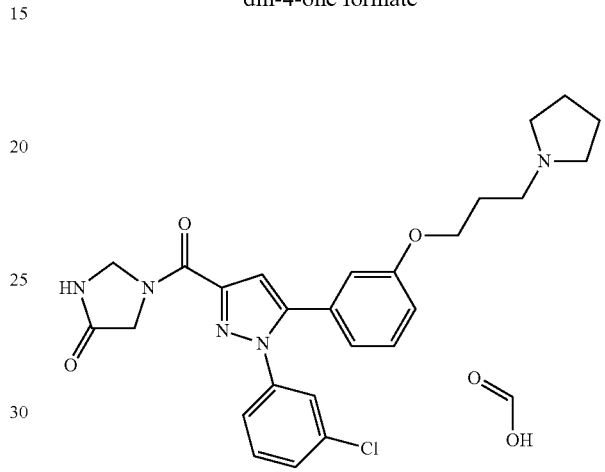

The preparation of the title compound takes place starting from the compound of Example 118A in analogy to the synthesis of the compound of Example 23. 3.2 mg (33% of theory) of the title compound are obtained.

$^1$H-NMR (400 MHz, DMSO-d$_6$): δ=8.71 (s, 0.6H), 8.61 (s, 0.4H), 8.17 (s, 1H), 7.56-7.44 (m, 3H), 7.32-7.24 (m, 2H), 7.13-7.11 (m, 1H), 6.98-6.94 (m, 1H), 6.89-6.86 (m, 1H), 6.82-6.78 (m, 1H), 5.34 (s, 0.8H), 4.90 (s, 1.2H), 4.45 (s, 1.2H), 3.98 (s, 0.8H), 3.94 (t, 2H), 2.49-2.43 (m, 6H), 1.86-1.78 (m, 2H), 1.71-1.66 (m, 4H).

LC-MS (Method 5): R$_t$=0.86 min; MS (ESIpos): m/z=494 [M+H]$^+$.

Example 32

1-{[1-(3-Bromophenyl)-5-(3-chlorophenyl)-1H-pyrazol-3-yl]carbonyl}imidazolidin-4-one

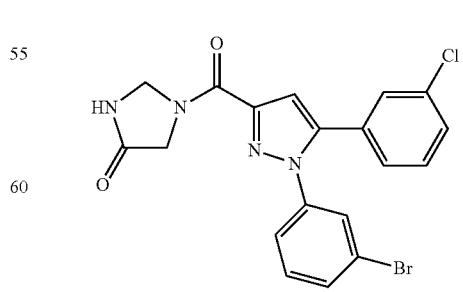

The preparation of the title compound takes place starting from the compound of Example 98A in analogy to the synthesis of the compound of Example 23. 122 mg (52% of theory) of the title compound are obtained.

$^1$H-NMR (400 MHz, DMSO-d$_6$): δ=8.72 (s, 0.6H), 8.62 (s, 0.4H), 7.71-7.65 (m, 2H), 7.51-7.38 (m, 4H), 7.36-7.29 (m, 1H), 7.22-7.17 (m, 2H), 5.34 (s, 0.8H), 4.90 (s, 1.2H), 4.45 (s, 1.2H), 3.98 (s, 0.8H).

LC-MS (Method 5): R$_t$=1.19 min; MS (ESIpos): m/z=445 [M+H]$^+$.

Example 33

1-{[1-(3-Bromophenyl)-5-(3-chloro-4-fluorophenyl)-1H-pyrazol-3-yl]carbonyl}imidazolidin-4-one

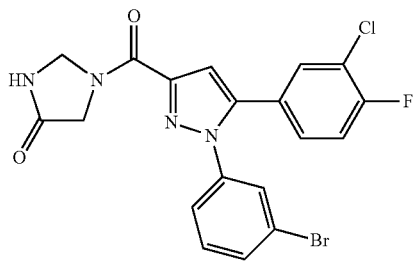

The preparation of the title compound takes place starting from the compound of Example 99A in analogy to the synthesis of the compound of Example 23. 186 mg (79% of theory) of the title compound are obtained.

$^1$H-NMR (400 MHz, DMSO-d$_6$): δ=8.72 (s, 0.6H), 8.62 (s, 0.4H), 7.73 (t, 1H), 7.69 (d, 1H), 7.52 (dt, 1H), 7.47-7.40 (m, 1H), 7.37-7.31 (m, 1H), 7.28-7.24 (m, 2H), 7.21-7.16 (m, 1H), 5.33 (s, 0.8H), 4.90 (s, 1.2H), 4.44 (s, 1.2H), 3.98 (s, 0.8H).

LC-MS (Method 7): R$_t$=1.93 min; MS (ESIpos): m/z=463 [M+H]$^+$.

Example 34

1-{[1-(3-Chlorophenyl)-5-(3-hydroxyphenyl)-1H-pyrazol-3-yl]carbonyl}imidazolidin-4-one

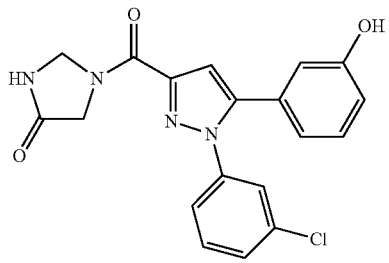 [SMILES: O=C1CN(C(=O)c2cc(-c3cccc(O)c3)n(-c3cccc(Cl)c3)n2)CN1]

100 mg (0.25 mmol) of the compound of Example 100A, 25.5 mg (0.30 mmol) of imidazolidin-4-one and 141 mg (0.27 mmol) of PyBOP are provided in 2 ml of tetrahydrofuran and, at room temperature, 47 μl (0.27 mmol) of N,N-diisopropylethylamine are added. The reaction mixture is stirred at room temperature overnight and subsequently purified by preparative HPLC (RP18 column; mobile phase: acetonitrile/water gradient). 83.5 mg (72% of theory) of 1-({5-[3-(benzyloxy)phenyl]-1-(3-chlorophenyl)-1H-pyrazol-3-yl}carbonyl)imidazolidin-4-one are obtained.

$^1$H-NMR (400 MHz, DMSO-d$_6$): δ=8.72 (s, 0.6H), 8.62 (s, 0.4H), 7.56-7.43 (m, 3H), 7.41-7.24 (m, 7H), 7.13-7.11 (m, 1H), 7.07-7.03 (m, 1H), 7.01-6.98 (m, 1H), 6.80 (d, 1H), 5.34 (s, 0.8H), 5.06 (s, 2H), 4.90 (s, 1.2H), 4.46 (s, 1.2H), 3.98 (s, 0.8H).

LC-MS (Method 9): R$_t$=2.25 min; MS (ESIpos): m/z=473 [M+H]$^+$.

317 mg (0.671 mmol) of 1-({5-[3-(benzyloxy)phenyl]-1-(3-chlorophenyl)-1H-pyrazol-3-yl}carbonyl)imidazolidin-4-one are provided in 5.6 ml of conc. acetic acid, 357 mg (0.168 mmol) of palladium on activated carbon (5%) are added, and the mixture is stirred at room temperature under a hydrogen atmosphere overnight. The reaction mixture is subsequently filtered, the filtrate is concentrated, and the residue is purified by preparative HPLC (RP18 column; mobile phase: acetonitrile/water gradient). 119 mg (46% of theory) of the title compound are obtained.

$^1$H-NMR (400 MHz, DMSO-d$_6$): δ=9.67 (s, 1H), 8.71 (s, 0.6H), 8.62 (s, 0.4H), 7.55-7.43 (m, 3H), 7.30-7.16 (m, 2H), 7.03-7.01 (m, 1H), 6.82-6.77 (m, 1H), 6.72-6.65 (m, 2H), 5.34 (s, 0.8H), 4.90 (s, 1.2H), 4.46 (s, 1.2H), 3.98 (s, 0.8H).

LC-MS (Method 1): R$_t$=1.90 min; MS (ESIpos): m/z=383 [M+H]$^+$.

Example 35

1-({1-(3-Chlorophenyl)-5-[3-(2-methoxyethoxy)phenyl]-1H-pyrazol-3-yl}carbonyl)imidazolidin-4-one

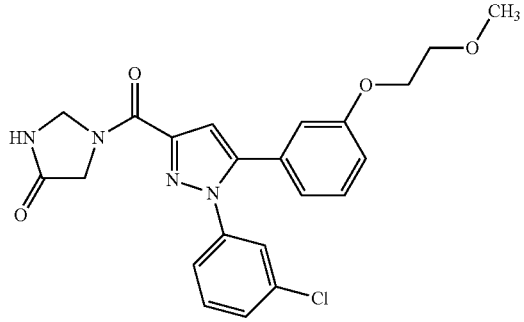 [SMILES: COCCOc1cccc(-c2cc(C(=O)N3CNC(=O)C3)nn2-c2cccc(Cl)c2)c1]

The preparation of the title compound takes place starting from the compound of Example 117A in analogy to the synthesis of the compound of Example 23. In order to remove the 1,1',1"-phosphoryltripyrrolidine the product is taken up in a little tetrahydrofuran, water is added to the mixture until a precipitate forms, the tetrahydrofuran is removed in vacuo, and the precipitate is collected by suction filtration, and dried under high vacuum. 10 mg (19% of theory) of the title compound are obtained.

$^1$H-NMR (400 MHz, DMSO-d$_6$): δ=8.72 (s, 0.6H), 8.62 (s, 0.4H), 7.56-7.44 (m, 3H), 7.32-7.24 (m, 2H), 7.13-7.11 (m, 1H), 7.00-6.96 (m, 1H), 6.91 (s, 1H), 6.80 (d, 1H), 5.34 (s, 0.8H), 4.90 (s, 1.2H), 4.46 (s, 1.2H), 4.03 (t, 2H), 3.98 (s, 0.8H), 3.60 (t, 2H), 3.28 (s, 3H).

LC-MS (Method 1): R$_t$=2.13 min; MS (ESIpos): m/z=441 [M+H]$^+$.

Example 36

1-({1-(3-Chloro-4-fluorophenyl)-5-{3-(2-hydroxyethoxy)phenyl}-1H-pyrazol-3-yl}carbonyl)imidazolidin-4-one

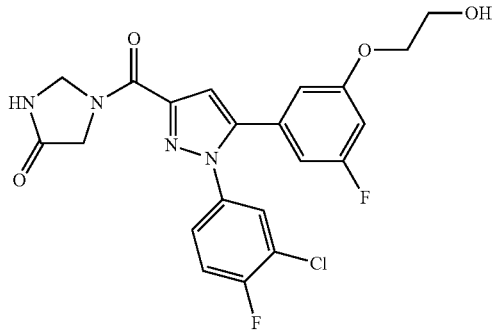 [SMILES: O=C1CN(C(=O)c2cc(-c3cc(F)cc(OCCO)c3)n(-c3ccc(F)c(Cl)c3)n2)CN1]

1.66 g (4.73 mmol) of the compound of Example 101A, 1.04 g (5.21 mmol) of the compound of Example 125A and 3.69 g (7.10 mmol) of PyBOP are provided in 80 ml of tetrahydrofuran and, at room temperature, 1.73 ml (9.94 mmol) of N,N-diisopropylethylamine are added. The mixture is stirred at room temperature overnight, water is added, the tetrahydrofuran is removed in vacuo, the residue is extracted with ethyl acetate and concentrated, and the residue is purified by flash chromatography (mobile phase: ethyl acetate/methanol 200/1). 1.24 g (63% of theory) of 1-{[1-(3-chloro-4-fluorophenyl)-5-(3-fluoro-5-hydroxyphenyl)-1H-pyrazol-3-yl]carbonyl}imidazolidin-4-one are obtained.

LC-MS (Method 7): $R_t$=1.59 min; MS (ESIpos): m/z=419 [M+H]$^+$.

100 mg (0.239 mmol) of 1-{[1-(3-chloro-4-fluorophenyl)-5-(3-fluoro-5-hydroxyphenyl)-1H-pyrazol-3-yl]carbonyl}imidazolidin-4-one are provided in 2.5 ml of dry acetone, 36.3 mg (0.263 mmol) of potassium carbonate and 149 mg (1.19 mmol) of 2-bromoethanol are added, and the mixture is heated under reflux overnight. The reaction mixture is subsequently purified by preparative HPLC (RP18 column; mobile phase: acetonitrile/water gradient). 30 mg (26% of theory) of the title compound are obtained.

$^1$H-NMR (400 MHz, DMSO-d$_6$): δ=8.72 (s, 0.6H), 8.62 (s, 0.4H), 7.80 (dd, 1H), 7.53 (dt, 1H), 7.40-7.32 (m, 1H), 7.19-7.17 (m, 1H), 6.90 (dt, 1H), 6.75-6.68 (m, 2H), 5.32 (s, 0.8H), 4.92-4.85 (m, 2.2H), 4.44 (s, 1.2H), 4.01-3.92 (m, 2.8H), 3.65 (q, 2H).

LC-MS (Method 7): $R_t$=1.53 min; MS (ESIpos): m/z=463 [M+H]$^+$.

Example 37

1-({1-(3-Chlorophenyl)-5-[3-(3-morpholin-1-ylpropoxy)phenyl]-1H-pyrazol-3-yl}carbonyl)imidazolidin-4-one

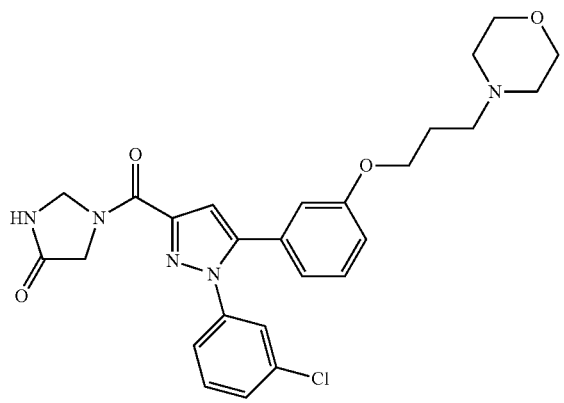 [SMILES: O=C1CN(C(=O)c2cc(-c3cccc(OCCCN4CCOCC4)c3)n(-c3cccc(Cl)c3)n2)CN1]

The preparation of the title compound takes place starting from the compound of Example 120A and morpholine without the addition of tetrahydrofuran in analogy to the synthesis of the compound of Example 29. 40 mg (36% of theory) of the title compound are obtained.

$^1$H-NMR (400 MHz, DMSO-d$_6$): δ=8.72 (s, 0.6H), 8.62 (s, 0.4H), 7.56-7.44 (m, 3H), 7.32-7.25 (m, 2H), 7.13-7.11 (m, 1H), 6.96 (dd, 1H), 6.88-6.85 (m, 1H), 6.81 (d, 1H), 5.34 (s, 0.8H), 4.90 (s, 1.2H), 4.46 (s, 1.2H), 3.98 (s, 0.8H), 3.93 (t, 2H), 3.56 (t, 4H), 2.39-2.30 (m, 6H), 1.84-1.75 (m, 2H).

LC-MS (Method 1): $R_t$=1.62 min; MS (ESIpos): m/z=510 [M+H]$^+$.

Example 38

1-{[1-(3-Chloro-4-fluorophenyl)-5-(3-methoxyphenyl)-1H-pyrazol-3-yl]carbonyl}imidazolidin-4-one

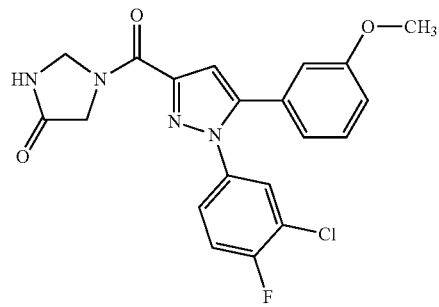 [SMILES: COc1cccc(-c2cc(C(=O)N3CNC(=O)C3)nn2-c2ccc(F)c(Cl)c2)c1]

The preparation of the title compound takes place starting from the compound of Example 102A in analogy to the synthesis of the compound of Example 23. 7 mg (12% of theory) of the title compound are obtained.

$^1$H-NMR (400 MHz, DMSO-d$_6$): δ=8.72 (s, 0.6H), 8.62 (s, 0.4H), 7.79-7.74 (m, 1H), 7.52 (dt, 1H), 7.38-7.27 (m, 2H), 7.14-7.11 (m, 1H), 7.00-6.95 (m, 1H), 6.93-6.90 (m, 1H), 6.80 (d, 1H), 5.34 (s, 0.8H), 4.90 (s, 1.2H), 4.45 (s, 1.2H), 3.98 (s, 0.8H), 3.71 (s, 3H).

LC-MS (Method 7): $R_t$=1.77 min; MS (ESIpos): m/z=415 [M+H]$^+$.

Example 39

1-({1-(3-Chlorophenyl)-5-[3-(3-(methylamino)propoxy)phenyl]-1H-pyrazol-3-yl}carbonyl)imidazolidin-4-one formate

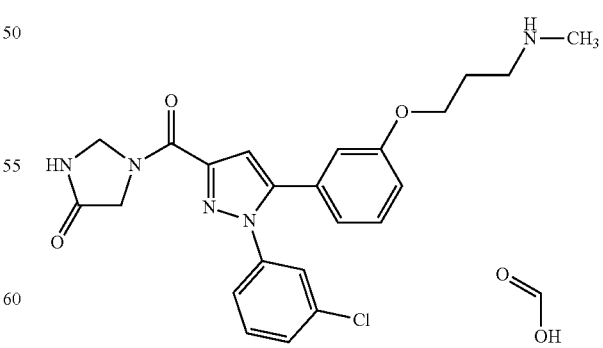

The preparation of the title compound takes place starting from the compound of Example 120A and methylamine without the addition of tetrahydrofuran in analogy to the synthesis of the compound of Example 29. 46 mg (44% of theory) of the title compound are obtained.

$^1$H-NMR (400 MHz, DMSO-d$_6$): δ=8.73 (s, 0.6H), 8.63 (s, 0.4H), 8.28 (s, 1H), 7.56-7.44 (m, 3H), 7.32-7.25 (m, 2H), 7.13-7.11 (m, 1H), 7.00-6.94 (m, 1H), 6.92 (t, 1H), 6.81-6.75 (m, 1H), 5.35 (s, 0.8H), 4.90 (s, 1.2H), 4.46 (s, 1.2H), 4.02-3.96 (m, 2.8H), 2.78 (t, 2H), 2.42 (s, 3H), 1.94-1.85 (m, 2H).

LC-MS (Method 1): R$_t$=1.62 min; MS (ESIpos): m/z=454 [M+H]$^+$.

Example 40

1-({1-(3-Chlorophenyl)-5-[3-(3-(ethylamino)propoxy)phenyl]-1H-pyrazol-3-yl}carbonyl)imidazolidin-4-one formate

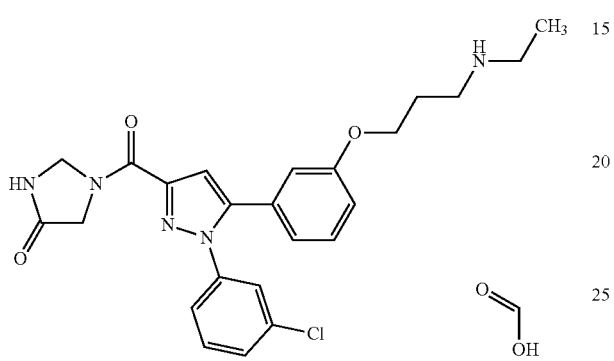

The preparation of the title compound takes place starting from the compound of Example 120A and ethylamine without the addition of tetrahydrofuran in analogy to the synthesis of the compound of Example 29. 23 mg (21% of theory) of the title compound are obtained.

$^1$H-NMR (400 MHz, DMSO-d$_6$): δ=8.72 (s, 0.6H), 8.63 (s, 0.4H), 8.29 (s, 1H), 7.56-7.44 (m, 3H), 7.32-7.24 (m, 2H), 7.13-7.11 (d, 1H), 6.99-6.94 (m, 1H), 6.90 (t, 1H), 6.81-6.76 (m, 1H), 5.35 (s, 0.8H), 4.90 (s, 1.2H), 4.46 (s, 1.2H), 4.01-3.96 (m, 2.8H), 2.78-2.64 (m, 4H), 1.90-1.81 (m, 2H), 1.06 (t, 3H).

LC-MS (Method 7): R$_t$=1.18 min; MS (ESIpos): m/z=468 [M+H]$^+$.

Example 41

1-({5-[3-(3-Azetidin-1-ylpropoxy)phenyl]-1-(3-chlorophenyl)-1H-pyrazol-3-yl}carbonyl)imidazolidin-4-one formate

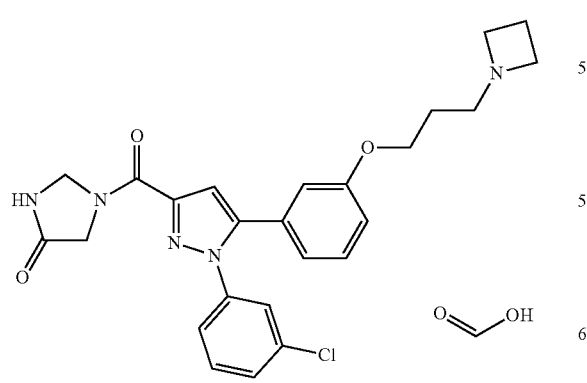

The preparation of the title compound takes place starting from the compound of Example 120A and azetidine without the addition of tetrahydrofuran in analogy to the synthesis of the compound of Example 29. 13 mg (11% of theory) of the title compound are obtained.

$^1$H-NMR (400 MHz, DMSO-d$_6$): δ=8.72 (s, 0.6H), 8.62 (s, 0.4H), 8.18 (s, 1H), 7.56-7.44 (m, 3H), 7.31-7.24 (m, 2H), 7.13-7.11 (m, 1H), 6.97-6.92 (m, 1H), 6.88-6.85 (m, 1H), 6.82-6.78 (m, 1H), 5.34 (s, 0.8H), 4.90 (s, 1.2H), 4.46 (s, 1.2H), 3.98 (s, 0.8H), 3.90 (t, 2H), 3.12 (t, 4H), 2.48-2.43 (m, 2H), 2.01-1.92 (m, 2H), 1.67-1.59 (m, 2H).

LC-MS (Method 1): R$_t$=1.44 min; MS (ESIpos): m/z=480 [M+H]$^+$.

Example 42

1-{[1-(3-Chlorophenyl)-5-{3-[2-(methylamino)ethoxy]phenyl}-1H-pyrazol-3-yl]carbonyl}imidazolidin-4-one formate

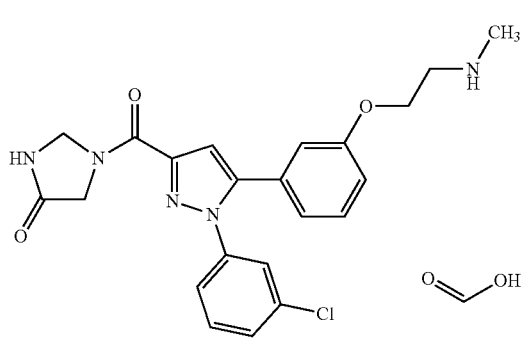 [SMILES: CNCCOc1cccc(-c2cc(C(=O)N3CNC(=O)C3)nn2-c2cccc(Cl)c2)c1 ; O=CO]

The preparation of the title compound takes place starting from the compound of Example 121A and methylamine without the addition of tetrahydrofuran in analogy to the synthesis of the compound of Example 29. 26 mg (26% of theory) of the title compound are obtained.

$^1$H-NMR (400 MHz, DMSO-d$_6$): δ=8.73 (s, 0.6H), 8.63 (s, 0.4H), 8.24 (s, 1H), 7.56-7.43 (m, 3H), 7.33-7.25 (m, 2H), 7.13-7.11 (m, 1H), 7.02-6.97 (m, 1H), 6.94-6.91 (m, 1H), 6.86-6.78 (m, 1H), 5.35 (s, 0.8H), 4.91 (s, 1.2H), 4.46 (s, 1.2H), 4.02 (t, 2H), 3.98 (s, 0.8H), 3.19-3.16 (m, 2H), 2.92 (t, 2H), 2.40 (s, 3H).

LC-MS (Method 1): R$_t$=1.52 min; MS (ESIpos): m/z=440 [M+H]$^+$.

Example 43

1-{[1-(3-Chlorophenyl)-5-{3-[3-(4-methylpiperazin-1-yl)propoxy]phenyl}-1H-pyrazol-3-yl]carbonyl}imidazolidin-4-one formate

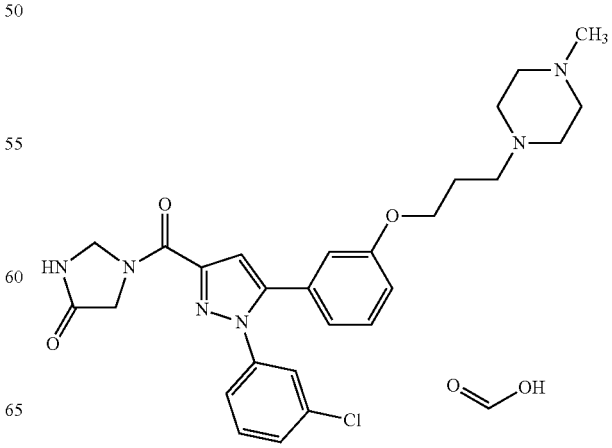

The preparation of the title compound takes place starting from the compound of Example 120A and 1-methylpiperazine without the addition of tetrahydrofuran in analogy to the synthesis of the compound of Example 29. 45 mg (38% of theory) of the title compound are obtained.

$^1$H-NMR (400 MHz, DMSO-d$_6$): δ=8.72 (s, 0.6H), 8.62 (s, 0.4H), 8.16 (s, 1H), 7.56-7.43 (m, 3H), 7.31-7.25 (m, 2H), 7.13-7.11 (m, 1H), 6.98-6.93 (m, 1H), 6.88-6.85 (m, 1H), 6.80 (d, 1H), 5.34 (s, 0.8H), 4.90 (s, 1.2H), 4.45 (s, 1.2H), 3.98 (s, 0.8H), 3.92 (t, 2H), 2.39-2.30 (m, 10H), 2.17 (s, 3H), 1.82-1.74 (m, 2H).

LC-MS (Method 1): R$_t$=1.40 min; MS (ESIpos): m/z=523 [M+H]$^+$.

Example 44

1-{[1-(3-Chlorophenyl)-5-{3-[2-(4-methylpiperazin-1-yl)ethoxy]phenyl}-1H-pyrazol-3-yl]carbonyl}imidazolidin-4-one diformate

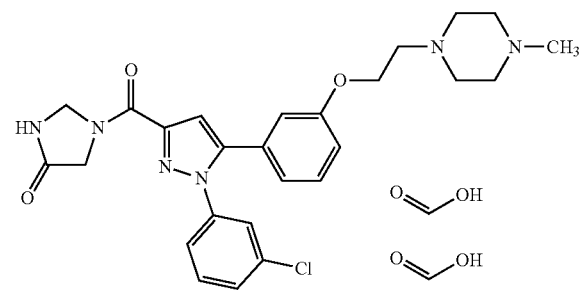 [SMILES: CN1CCN(CCOc2cccc(-c3cc(C(=O)N4CNC(=O)C4)nn3-c3cccc(Cl)c3)c2)CC1 ; O=CO ; O=CO]

The preparation of the title compound takes place starting from the compound of Example 121A and 1-methylpiperazine without the addition of tetrahydrofuran in analogy to the synthesis of the compound of Example 29. 46 mg (38% of theory) of the title compound are obtained.

$^1$H-NMR (400 MHz, DMSO-d$_6$): δ=8.72 (s, 0.6H), 8.62 (s, 0.4H), 8.15 (s, 2H), 7.56-7.44 (m, 3H), 7.31-7.25 (m, 2H), 7.14-7.12 (d, 1H), 6.99-6.95 (m, 1H), 6.90-6.87 (m, 1H), 6.83-6.79 (m, 1H), 5.34 (s, 0.8H), 4.90 (s, 1.2H), 4.46 (s, 1.2H), 4.02-3.97 (m, 2.8H), 2.63-2.58 (m, 2H), 2.48-2.30 (m, 8H), 2.18 (s, 3H).

LC-MS (Method 1): R$_t$=1.39 min; MS (ESIpos): m/z=509 [M+H]$^+$.

Example 45

1-({1-(3-Chlorophenyl)-5-[3-(2-morpholin-4-ylethoxy)phenyl]-1H-pyrazol-3-yl}carbonyl)imidazolidin-4-one formate

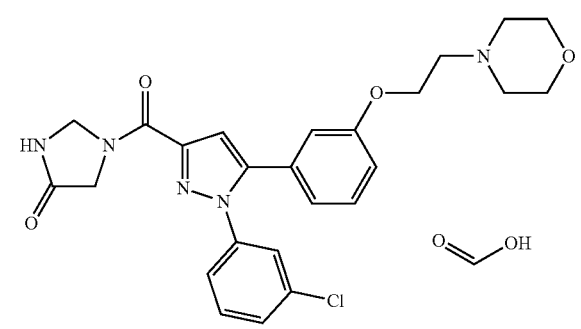 [SMILES: O=C1CN(C(=O)c2cc(-c3cccc(OCCN4CCOCC4)c3)n(-c3cccc(Cl)c3)n2)CN1 ; O=CO]

The preparation of the title compound takes place starting from the compound of Example 121A and morpholine without the addition of tetrahydrofuran in analogy to the synthesis of the compound of Example 29. 47 mg (43% of theory) of the title compound are obtained.

$^1$H-NMR (400 MHz, DMSO-d$_6$): δ=8.72 (s, 0.6H), 8.62 (s, 0.4H), 8.14 (s, 1H), 7.56-7.44 (m, 3H), 7.32-7.25 (m, 2H), 7.14-7.12 (m, 1H), 6.99-6.95 (m, 1H), 6.90-6.87 (m, 1H), 6.81 (d, 1H), 5.34 (s, 0.8H), 4.90 (s, 1.2H), 4.46 (s, 1.2H), 4.01 (t, 2H), 3.98 (s, 0.8H), 3.56 (t, 4H), 2.61 (t, 2H), 2.42 (t, 4H).

LC-MS (Method 1): R$_t$=1.58 min; MS (ESIpos): m/z=496 [M+H]$^+$.

Example 46

1-{[1-(3-Chlorophenyl)-5-(3-{2-[(1-methylethyl)amino]ethoxy}phenyl)-1H-pyrazol-3-yl]carbonyl}imidazolidin-4-one formate

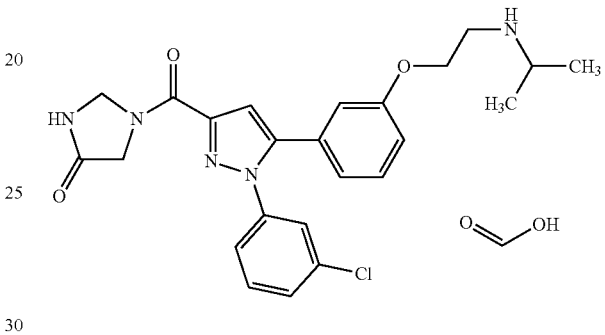

The preparation of the title compound takes place starting from the compound of Example 121A and isopropylamine without the addition of tetrahydrofuran in analogy to the synthesis of the compound of Example 29. 29 mg (28% of theory) of the title compound are obtained.

$^1$H-NMR (400 MHz, DMSO-d$_6$): δ=8.72 (s, 0.6H), 8.63 (s, 0.4H), 8.20 (s, 1H), 7.56-7.44 (m, 3H), 7.33-7.25 (m, 2H), 7.13-7.11 (m, 1H), 7.02-6.97 (m, 1H), 6.94-6.91 (m, 1H), 6.83-6.78 (m, 1H), 5.35 (s, 0.8H), 4.90 (s, 1.2H), 4.46 (s, 1.2H), 4.03-3.97 (m, 2.8H), 2.95-2.85 (m, 3H), 1.03 (d, 6H).

LC-MS (Method 1): R$_t$=1.42 min; MS (ESIpos): m/z=468 [M+H]$^+$.

Example 47

1-({5-[3,5-Bis(trifluoromethyl)phenyl]-1-(3-chlorophenyl)-1H-pyrazol-3-yl}carbonyl)imidazolidin-4-one

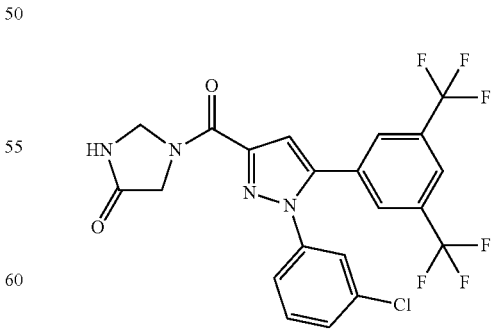

The preparation of the title compound takes place starting from the compound of Example 103A in analogy to the synthesis of the compound of Example 1. 26 mg (72% of theory) of the title compound are obtained.

¹H-NMR (400 MHz, DMSO-d₆): δ=8.73 (s, 0.6H), 8.63 (s, 0.4H), 8.16 (s, 1H), 7.96 (s, 2H), 7.66-7.63 (m, 1H), 7.60-7.55 (m, 1H), 7.53-7.46 (m, 2H), 7.38-7.31 (m, 1H), 5.34 (s, 0.8H), 4.92 (s, 1.2H), 4.46 (s, 1.2H), 4.00 (s, 0.8H).

LC-MS (Method 7): $R_t$=2.14 min; MS (ESIpos): m/z=503 [M+H]⁺.

Example 48

1-({1-(4-Chlorophenyl)-5-[3-(trifluoromethyl)phenyl]-1H-pyrazol-3-yl}carbonyl)imidazolidin-4-one

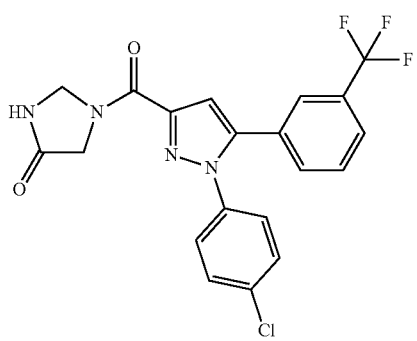 [SMILES: O=C1CN(C(=O)c2cc(-c3cccc(C(F)(F)F)c3)n(-c3ccc(Cl)cc3)n2)CN1]

The preparation of the title compound takes place starting from the compound of Example 104A in analogy to the synthesis of the compound of Example 1. 34 mg (92% of theory) of the title compound are obtained.

¹H-NMR (400 MHz, DMSO-d₆): δ=8.72 (s, 0.6H), 8.65 (s, 0.4H), 7.77 (d, 1H), 7.67-7.60 (m, 2H), 7.59-7.53 (m, 3H), 7.45-7.39 (m, 2H), 7.29-7.27 (m, 1H), 5.33 (s, 0.8H), 4.91 (s, 1.2H), 4.44 (s, 1.2H), 3.99 (s, 0.8H).

LC-MS (Method 7): $R_t$=1.95 min; MS (ESIpos): m/z=435 [M+H]⁺.

Example 49

1-{[1-(4-Chlorophenyl)-5-(3-fluorophenyl)-1H-pyrazol-3-yl]carbonyl}imidazolidin-4-one

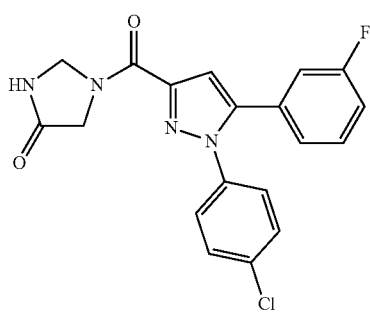 [SMILES: O=C1CN(C(=O)c2cc(-c3cccc(F)c3)n(-c3ccc(Cl)cc3)n2)CN1]

The preparation of the title compound takes place starting from the compound of Example 105A in analogy to the synthesis of the compound of Example 1. 15 mg (39% of theory) of the title compound are obtained.

¹H-NMR (400 MHz, DMSO-d₆): δ=8.71 (s, 0.6H), 8.64 (s, 0.4H), 7.58-7.53 (m, 2H), 7.47-7.38 (m, 3H), 7.29-7.16 (m, 3H), 7.07 (d, 1H), 5.33 (s, 0.8H), 4.90 (s, 1.2H), 4.44 (s, 1.2H), 3.98 (s, 0.8H).

LC-MS (Method 5): $R_t$=1.14 min; MS (ESIpos): m/z=385 [M+H]⁺.

Example 50

1-{[1-(3-Chloro-4-fluorophenyl)-5-(3-fluoro-5-methylphenyl)-1H-pyrazol-3-yl]carbonyl}imidazolidin-4-one

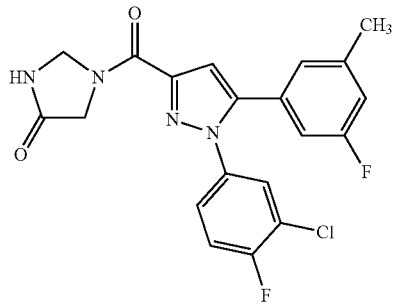 [SMILES: Cc1cc(F)cc(-c2cc(C(=O)N3CNC(=O)C3)nn2-c2ccc(F)c(Cl)c2)c1]

The preparation of the title compound takes place starting from the compound of Example 106A using 3.2 equivalents of N,N-diisopropylethylamine and with the addition of 0.1% formic acid in the preparative HPLC in analogy to the synthesis of the compound of Example 23. 5 mg (6% of theory) of the title compound are obtained.

¹H-NMR (400 MHz, DMSO-d₆): δ=8.72 (s, 0.6H), 8.62 (s, 0.4H), 7.81-7.77 (m, 1H), 7.56-7.49 (m, 1H), 7.38-7.31 (m, 1H), 7.16-7.08 (m, 2H), 7.03-7.00 (m, 1H), 6.95-6.90 (m, 1H), 5.33 (s, 0.8H), 4.90 (s, 1.2H), 4.44 (s, 1.2H), 3.98 (s, 0.8H), 2.28 (s, 3H).

LC-MS (Method 1): $R_t$=2.36 min; MS (ESIpos): m/z=417 [M+H]⁺.

Example 51

1-{[1-(3-Chlorophenyl)-5-(3-fluoro-5-methylphenyl)-1H-pyrazol-3-yl]carbonyl}imidazolidin-4-one

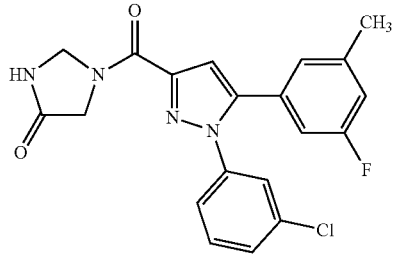 [SMILES: Cc1cc(F)cc(-c2cc(C(=O)N3CNC(=O)C3)nn2-c2cccc(Cl)c2)c1]

The preparation of the title compound takes place starting from the compound of Example 107A using 3.2 equivalents of N,N-diisopropylethylamine and with the addition of 0.1% formic acid in the preparative HPLC in analogy to the synthesis of the compound of Example 23. 24 mg (19% of theory) of the title compound are obtained.

¹H-NMR (400 MHz, DMSO-d₆): δ=8.72 (s, 0.6H), 8.62 (s, 0.4H), 7.59-7.45 (m, 3H), 7.30-7.24 (m, 1H), 7.16-7.08 (m, 2H), 7.02 (s, 1H), 6.93-6.87 (m, 1H), 5.34 (s, 0.8H), 4.90 (s, 1.2H), 4.45 (s, 1.2H), 3.98 (s, 0.8H), 2.28 (s, 3H).

Example 52

1-{[5-(3-Chloro-4-fluorophenyl)-1-(3-Cyanophenyl)-1H-pyrazol-3-yl]carbonyl}imidazolidin-4-one

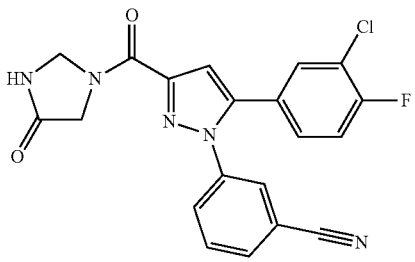 [SMILES: N#Cc1cccc(-n2nc(C(=O)N3CNC(=O)C3)cc2-c2ccc(F)c(Cl)c2)c1]

The preparation of the title compound takes place starting from the compound of Example 108A with the addition of 0.1% formic acid in the preparative HPLC in analogy to the synthesis of the compound of Example 23. 8 mg (35% of theory) of the title compound are obtained.

$^1$H-NMR (400 MHz, DMSO-d$_6$): δ=8.72 (s, 0.6H), 8.64 (s, 0.4H), 8.08-8.05 (m, 1H), 7.98-7.94 (m, 1H), 7.70-7.65 (m, 2H), 7.53 (dt, 1H), 7.30-7.25 (m, 2H), 7.21-7.16 (m, 1H), 5.33 (s, 0.8H), 4.91 (s, 1.2H), 4.46 (s, 1.2H), 3.99 (s, 0.8H).

LC-MS (Method 1): R$_t$=2.14 min; MS (ESIpos): m/z=410 [M+H]$^+$.

Example 53

1-{[5-(3-Chlorophenyl)-1-(3-Cyano-4-fluorophenyl)-1H-pyrazol-3-yl]carbonyl}imidazolidin-4-one

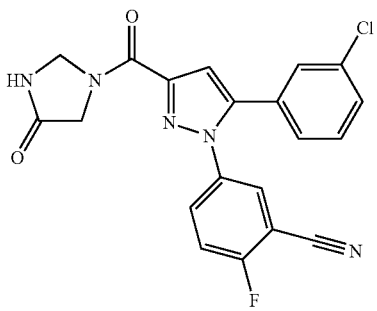 [SMILES: N#Cc1cc(-n2nc(C(=O)N3CNC(=O)C3)cc2-c2cccc(Cl)c2)ccc1F]

The preparation of the title compound takes place starting from the compound of Example 109A using 3.2 equivalents of N,N-diisopropylethylamine and with the addition of 0.1% formic acid in the preparative HPLC in analogy to the synthesis of the compound of Example 23. 45 mg (77% of theory) of the title compound are obtained.

$^1$H-NMR (400 MHz, DMSO-d$_6$): δ=8.72 (s, 0.6H), 8.65 (s, 0.4H), 8.22-8.17 (m, 1H), 7.77-7.70 (m, 1H), 7.63 (t, 1H), 7.53-7.47 (m, 2H), 7.40 (t, 1H), 7.23-7.21 (m, 1H), 7.16 (d, 1H), 5.34 (s, 0.8H), 4.91 (s, 1.2H), 4.46 (s, 1.2H), 3.99 (s, 0.8H).

LC-MS (Method 1): R$_t$=2.16 min; MS (ESIpos): m/z=410 [M+H]$^+$.

Example 54

1-({1-(3-Chloro-4-fluorophenyl)-5-[3-fluoro-5-(2-pyrrolidin-1-ylethoxy)phenyl]-1H-pyrazol-3-yl}carbonyl)imidazolidin-4-one

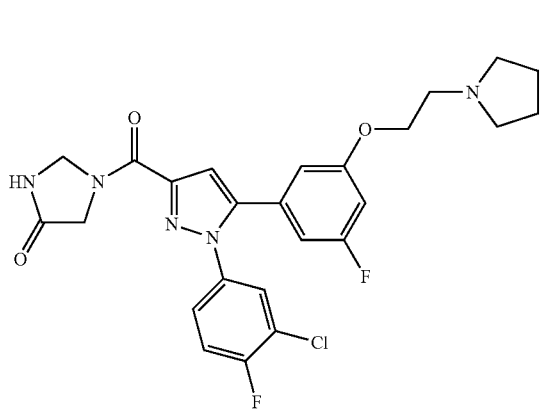 [SMILES: O=C1CN(C(=O)c2cc(-c3cc(F)cc(OCCN4CCCC4)c3)n(-c3ccc(F)c(Cl)c3)n2)CN1]

The preparation of the title compound takes place starting from the compound of Example 119A and pyrrolidine without the addition of 0.1% formic acid in the preparative HPLC in analogy to the synthesis of the compound of Example 29. 2.5 mg (5% of theory) of the title compound are obtained.

$^1$H-NMR (500 MHz, DMSO-d$_6$): δ=8.74 (s, 0.6H), 8.65 (s, 0.4H), 7.84-7.78 (m, 1H), 7.59-7.51 (m, 1H), 7.41-7.33 (m, 1H), 7.20 (s, 1H), 6.90 (d, 1H), 6.77 (d, 1H), 6.67 (s, 1H), 5.32 (s, 0.8H), 4.90 (s, 1.2H), 4.44 (s, 1.2H), 4.05-3.95 (m, 2.8H), 2.71-2.63 (m, 2H), 2.44 (s, 4H), 1.66 (s, 4H).

LC-MS (Method 1): R$_t$=1.52 min; MS (ESIpos): m/z=516 [M+H]$^+$.

Example 55

1-({5-[3-(3-Aminopropoxy)phenyl]-1-(3-chlorophenyl)-1H-pyrazol-3-yl}carbonyl)imidazolidin-4-one formate

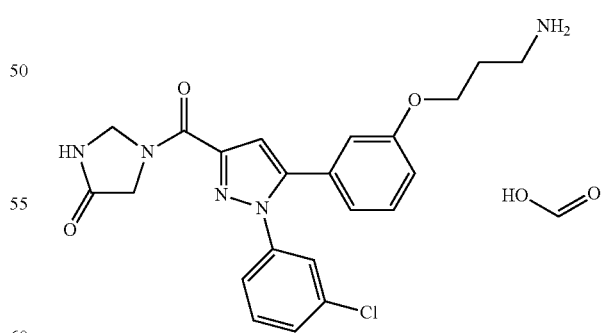

The preparation of the title compound takes place starting from the compound of Example 120A and a 7N solution of ammonia in methanol with the addition of 0.1% formic acid in the preparative HPLC in analogy to the synthesis of the compound of Example 29. 10 mg (10% of theory) of the title compound are obtained.

¹H-NMR (400 MHz, DMSO-d₆): δ=8.72 (s, 0.6H), 8.63 (s, 0.4H), 8.36 (s, 1H), 7.56-7.44 (m, 3H), 7.32-7.24 (m, 2H), 7.12-7.10 (m, 1H), 7.00-6.92 (m, 2H), 6.80-6.75 (m, 1H), 5.35 (s, 0.8H), 4.90 (s, 1.2H), 4.46 (s, 1.2H), 4.04-3.97 (m, 2.8H), 2.81 (t, 2H), 1.92-1.83 (m, 2H).

LC-MS (Method 1): R$_t$=1.41 min; MS (ESIpos): m/z=440 [M+H]⁺.

Example 56

3-{5-(3-Chlorophenyl)-3-[(4-oxoimidazolidin-1-yl)carbonyl]-1H-pyrazol-1-yl}benzenecarbonitrile

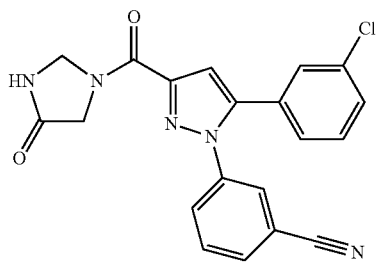 [SMILES: N#Cc1cccc(-n2nc(C(=O)N3CNC(=O)C3)cc2-c2cccc(Cl)c2)c1]

The preparation of the title compound takes place starting from the compound of Example 110A using 3.2 equivalents of N,N-diisopropylethylamine and with the addition of 0.1% formic acid in the preparative HPLC in analogy to the synthesis of the compound of Example 23. In order to remove the 1,1',1''-phosphoryltripyrrolidine the product is taken up in a little tetrahydrofuran, water is added to the mixture until a precipitate forms, the tetrahydrofuran is removed in vacuo, and the precipitate is collected by suction filtration and dried under high vacuum. 42 mg (65% of theory) of the title compound are obtained.

¹H-NMR (400 MHz, DMSO-d₆): δ=8.72 (s, 0.6H), 8.64 (s, 0.4H), 8.05-8.02 (m, 1H), 7.96-7.92 (m, 1H), 7.68-7.63 (m, 2H), 7.52-7.45 (m, 2H), 7.41 (t, 1H), 7.23-7.21 (m, 1H), 7.18 (dt, 1H), 5.35 (s, 0.8H), 4.91 (s, 1.2H), 4.47 (s, 1.2H), 3.99 (s, 0.8H).

LC-MS (Method 1): R$_t$=2.10 min; MS (ESIpos): m/z=392 [M+H]⁺.

Example 57

3,3'-{3-[(4-Oxoimidazolidin-1-yl)carbonyl]-1H-pyrazol-1,5-diyl}dibenzenecarbonitrile

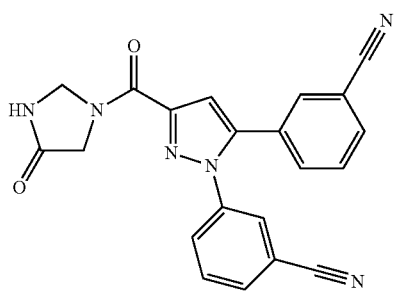 [SMILES: N#Cc1cccc(-c2cc(C(=O)N3CNC(=O)C3)nn2-c2cccc(C#N)c2)c1]

The preparation of the title compound takes place starting from the compound of Example 111A using 3.2 equivalents of N,N-diisopropylethylamine and with the addition of 0.1% formic acid in the preparative HPLC in analogy to the synthesis of the compound of Example 23. 16 mg (29% of theory) of the title compound are obtained.

¹H-NMR (400 MHz, DMSO-d₆): δ=8.73 (s, 0.6H), 8.65 (s, 0.4H), 8.06-8.03 (m, 1H), 7.97-7.87 (m, 3H), 7.67-7.63 (m, 2H), 7.58 (t, 1H), 7.52 (dt, 1H), 7.29-7.27 (m, 1H), 5.36 (s, 0.8H), 4.91 (s, 1.2H), 4.47 (s, 1.2H), 3.99 (s, 0.8H).

LC-MS (Method 5): R$_t$=0.91 min; MS (ESIpos): m/z=383 [M+H]⁺.

Example 58

5-{5-(3-Cyanophenyl)-3-[(4-oxoimidazolidin-1-yl)carbonyl]-1H-pyrazol-1-yl}-2-fluorobenzenecarbonitrile

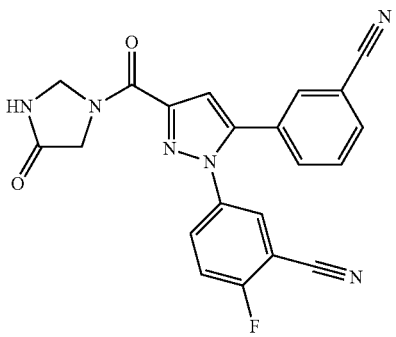 [SMILES: N#Cc1cccc(-c2cc(C(=O)N3CNC(=O)C3)nn2-c2ccc(F)c(C#N)c2)c1]

The preparation of the title compound takes place starting from the compound of Example 112A using 3.2 equivalents of N,N-diisopropylethylamine and with the addition of 0.1% formic acid in the preparative HPLC in analogy to the synthesis of the compound of Example 23. In order to remove the 1,1',1''-phosphoryltripyrrolidine the product is taken up in a little tetrahydrofuran, water is added to the mixture until a precipitate forms, the tetrahydrofuran is removed in vacuo, and the precipitate is collected by suction filtration, and dried under high vacuum. 25 mg (48% of theory) of the title compound are obtained.

¹H-NMR (400 MHz, DMSO-d₆): δ=8.73 (s, 0.6H), 8.66 (s, 0.4H), 8.23-8.18 (m, 1H), 7.97-7.94 (m, 1H), 7.89 (dt, 1H), 7.76-7.70 (m, 1H), 7.66-7.50 (m, 3H), 7.29-7.27 (m, 1H), 5.34 (s, 0.8H), 4.91 (s, 1.2H), 4.46 (s, 1.2H), 3.99 (s, 0.8H).

LC-MS (Method 1): R$_t$=1.93 min; MS (ESIpos): m/z=401 [M+H]⁺.

Example 59

3-{5-(3-Chloro-5-fluorophenyl)-3-[4-oxoimidazolidin-1-yl)carbonyl]-1H-pyrazol-1-yl}benzenecarbonitrile

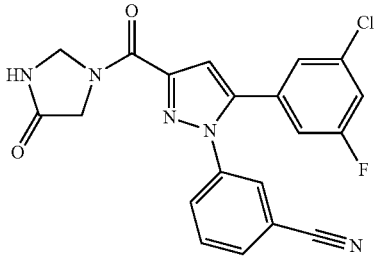 [SMILES: N#Cc1cccc(-n2nc(C(=O)N3CNC(=O)C3)cc2-c2cc(F)cc(Cl)c2)c1]

The preparation of the title compound takes place starting from the compound of Example 113A using 3.2 equivalents of N,N-diisopropylethylamine and with the addition of 0.1% formic acid in the preparative HPLC in analogy to the synthesis of the compound of Example 23. 58 mg (77% of theory) of the title compound are obtained.

¹H-NMR (400 MHz, DMSO-d₆): δ=8.72 (s, 0.6H), 8.64 (s, 0.4H), 8.08-8.04 (m, 1H), 7.98-7.94 (m, 1H), 7.70-7.65 (m, 2H), 7.54 (dt, 1H), 7.30-7.28 (m, 1H), 7.28-7.25 (m, 1H), 7.21-7.16 (m, 1H), 5.34 (s, 0.8H), 4.91 (s, 1.2H), 4.46 (s, 1.2H), 3.99 (s, 0.8H).

LC-MS (Method 5): $R_t$=1.10 min; MS (ESIpos): m/z=410 [M+H]⁺.

Example 60

5-{5-(3-Chloro-5-fluorophenyl)-3-[(4-oxoimidazolidin-1-yl)carbonyl]-1H-pyrazol-1-yl}-2-fluorobenzenecarbonitrile

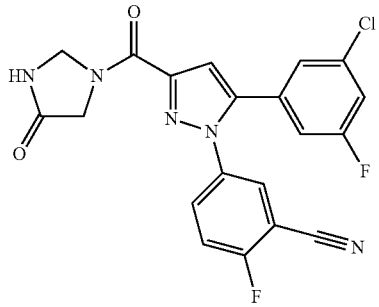 [SMILES: N#Cc1cc(-n2nc(C(=O)N3CNC(=O)C3)cc2-c2cc(F)cc(Cl)c2)ccc1F]

The preparation of the title compound takes place starting from the compound of Example 114A using 3.2 equivalents of N,N-diisopropylethylamine and with the addition of 0.1% formic acid in the preparative HPLC in analogy to the synthesis of the compound of Example 23. 44 mg (48% of theory) of the title compound are obtained.

¹H-NMR (400 MHz, DMSO-d₆): δ=8.73 (s, 0.6H), 8.65 (s, 0.4H), 8.24-8.19 (m, 1H), 7.79-7.72 (m, 1H), 7.65 (t, 1H), 7.54 (dt, 1H), 7.32-7.29 (m, 1H), 7.29-7.27 (m, 1H), 7.22-7.17 (m, 1H), 5.33 (s, 0.8H), 4.91 (s, 1.2H), 4.45 (s, 1.2H), 3.99 (s, 0.8H).

LC-MS (Method 5): $R_t$=1.14 min; MS (ESIpos): m/z=428 [M+H]⁺.

Example 61

3-{1-(3-Chlorophenyl)-3-[(4-oxoimidazolidin-1-yl)carbonyl]-1H-pyrazol-5-yl}-5-fluorobenzenecarbonitrile

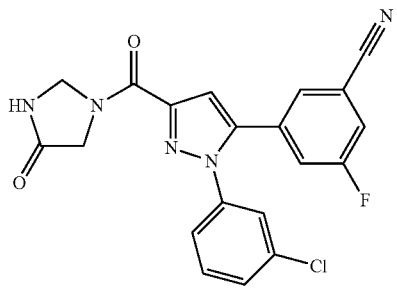 [SMILES: N#Cc1cc(F)cc(-c2cc(C(=O)N3CNC(=O)C3)nn2-c2cccc(Cl)c2)c1]

80.0 mg (0.190 mmol) of the compound of Example 131A with 81% purity, 49.5 mg (0.247 mmol) of the compound of Example 125A and 175 mg (0.337 mmol) of PyBOP are provided in 3.0 ml of tetrahydrofuran and, at room temperature, 125 µl (0.179 mmol) of N,N-diisopropylethylamine are added. The mixture is stirred at room temperature overnight, and the reaction solution is diluted with dichloromethane and subsequently washed with a 1N aqueous hydrogen chloride solution. After drying the organic phase over magnesium sulfate, filtration and concentration in vacuo, the crude product is purified by preparative HPLC (RP18 column; mobile phase: acetonitrile/water gradient). 56.0 mg (72% of theory) of the title compound are obtained.

¹H-NMR (400 MHz, DMSO-d₆): δ=8.73 (br. s., 0.6H), 8.62 (s, 0.4H), 7.94 (d, 1H), 7.71 (br. s., 1H), 7.66-7.44 (m, 4H), 7.37-7.23 (m, 2H), 5.33 (s, 0.8H), 4.91 (s, 1.2H), 4.45 (s, 1.2H), 3.99 (s, 0.8H).

LC-MS (Method 5): $R_t$=1.09 min; MS (ESIpos): m/z=410 [M+H]⁺.

Example 62

3-{1-(3-Chloro-4-fluorophenyl)-3-[(4-oxoimidazolidin-1-yl)carbonyl]-1H-pyrazol-5-yl}-5-fluorobenzenecarbonitrile

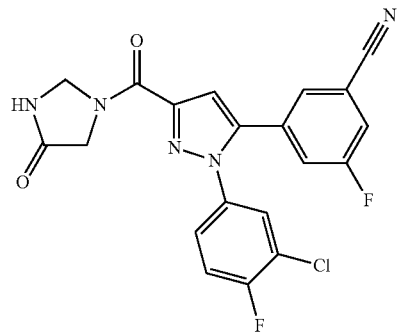 [SMILES: N#Cc1cc(F)cc(-c2cc(C(=O)N3CNC(=O)C3)nn2-c2ccc(F)c(Cl)c2)c1]

100 mg (0.263 mmol) of the compound of Example 129A, 57.8 mg (0.289 mmol) of the compound of Example 125A and 205 mg (0.394 mmol) of PyBOP are provided in 5.0 ml of tetrahydrofuran and, at room temperature, 146 µl (0.841 mmol) of N,N-diisopropylethylamine are added. The mixture is stirred at room temperature overnight, and the reaction solution is diluted with dichloromethane and subsequently washed with a 1N aqueous hydrogen chloride solution. After drying the organic phase over magnesium sulfate, filtration and concentration in vacuo, the crude product is purified by preparative HPLC (RP18 column; mobile phase: acetonitrile/water gradient). 78.0 mg (66% of theory) of the title compound are obtained.

¹H-NMR (400 MHz, DMSO-d₆): δ=8.73 (s, 0.6H), 8.63 (s, 0.4H), 7.94 (d, 1H), 7.84 (d, 1H), 7.73 (d, 1H), 7.61-7.48 (m, 2H), 7.43-7.25 (m, 2H), 5.33 (s, 0.8H), 4.91 (s, 1.2H), 4.44 (s, 1.2H), 3.99 (s, 0.8H).

LC-MS (Method 1): $R_t$=2.09 min; MS (ESIpos): m/z=428 [M+H]⁺.

Example 63

5-{5-(3-Cyano-5-fluorophenyl)-3-[(4-oxoimidazolidin-1-yl)carbonyl]-1H-pyrazol-1-yl}-2-fluorobenzenecarbonitrile

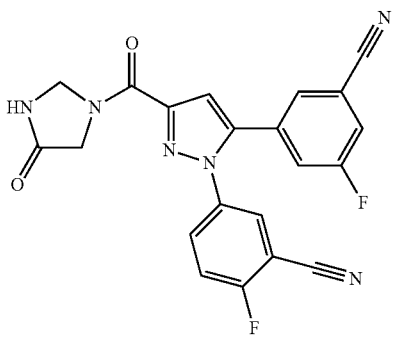 [SMILES: N#Cc1cc(F)cc(-c2cc(C(=O)N3CNC(=O)C3)nn2-c2ccc(F)c(C#N)c2)c1]

80.0 mg (0.228 mmol) of the compound of Example 133A, 50.3 mg (0.251 mmol) of the compound of Example 125A and 178 mg (0.394 mmol) of PyBOP are provided in 5.0 ml of tetrahydrofuran and, at room temperature, 127 µl (0.731 mmol) of N,N-diisopropylethylamine are added. The mixture is stirred at room temperature overnight, and the reaction solution is diluted with dichloromethane and subsequently washed with a 1N aqueous hydrogen chloride solution. After drying the organic phase over magnesium sulfate, filtration and concentration in vacuo, the crude product is purified by preparative HPLC (RP18 column; mobile phase: acetonitrile/water gradient). The obtained solid is suspended in acetonitrile/diethyl ether, stirred for 30 min and subsequently filtered. 20.0 mg (21% of theory) of the title compound are obtained.

$^1$H-NMR (400 MHz, DMSO-$d_6$): δ=8.73 (s, 0.6H), 8.65 (s, 0.4H), 8.27-8.13 (m, 1H), 7.95 (d, 1H), 7.74 (d, 2H), 7.68-7.52 (m, 2H), 7.33 (s, 1H), 5.34 (s, 0.8H), 4.91 (s, 1.2H), 4.46 (s, 1.2H), 3.99 (s, 0.8H).

LC-MS (Method 5): $R_t$=1.00 min; MS (ESIpos): m/z=419 [M+H]$^+$.

Example 64

3-{1-(3-Cyanophenyl)-3-[(4-oxoimidazolidin-1-yl)carbonyl]-1H-pyrazol-5-yl}-5-fluorobenzenecarbonitrile

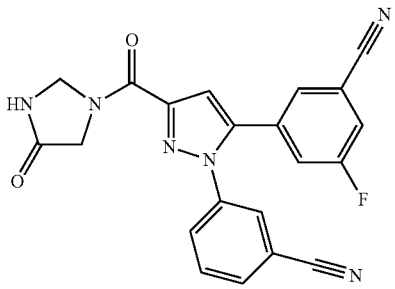 [SMILES: N#Cc1cc(F)cc(-c2cc(C(=O)N3CNC(=O)C3)nn2-c2cccc(C#N)c2)c1]

100 mg (0.301 mmol) of the compound of Example 135A, 66.2 mg (0.331 mmol) of the compound of Example 125A and 235 mg (0.451 mmol) of PyBOP are provided in 5.0 ml of tetrahydrofuran and, at room temperature, 168 µl (0.936 mmol) of N,N-diisopropylethylamine are added. The mixture is stirred at room temperature overnight, and the reaction solution is diluted with dichloromethane and subsequently washed with a 1N aqueous hydrogen chloride solution. After drying the organic phase over magnesium sulfate, filtration and concentration in vacuo, the crude product is purified by preparative HPLC (RP18 column; mobile phase: acetonitrile/water gradient). The obtained solid is suspended in acetonitrile/diethyl ether, stirred for 30 min and subsequently filtered. 18.0 mg (15% of theory) of the title compound are obtained.

$^1$H-NMR (400 MHz, DMSO-$d_6$): δ=8.73 (s, 0.6H), 8.64 (s, 0.4H), 8.07 (d, 1H), 8.00-7.90 (m, 2H), 7.76-7.70 (m, 1H), 7.69-7.62 (m, 2H), 7.56 (dd, 1H), 7.37-7.31 (m, 1H), 5.35 (s, 0.8H), 4.91 (s, 1.2H), 4.46 (s, 1.2H), 3.99 (s, 0.8H).

LC-MS (Method 5): $R_t$=0.97 min; MS (ESIpos): m/z=401 [M+H]$^+$.

B) Assessment of the Physiological Activity

Abbreviations

DMSO dimethyl sulfoxide
FCS fetal calf serum (Biochrom AG, Berlin, Germany)
PBS phosphate buffered saline
MTP microtiter plate
ELISA enzyme-linked immunosorbent assay The suitability of the compounds of the invention for the treatment of diseases caused by retroviruses can be shown in the following assay systems:

In Vitro Assays

Biochemical Reverse Transcriptase Assay

The "Reverse Transcriptase Assay, colorimetric" (Roche Diagnostics GmbH, Mannheim, Germany) is used in accordance with the manufacturer's information. The test substances are dissolved in DMSO and are used in the test diluted in 5-fold steps (final DMSO concentration 1%). The resulting values of the photometric evaluation (405/492 nm) are less than 0.1 for the negative control (mixture without reverse transcriptase) and are in the region of 1.5 for the positive control (mixture without test substance). The IC$_{50}$ values of the test substances are determined as the concentration of the test substance dilution at which the measured optical density is 50% of the positive control.

It is found that the compounds of the invention inhibit the reverse transcriptase activity. Experimental data are summarized in Table A.

Light Assay with Wild-Type and Inhibitor-Resistant HI Reporter Viruses

HIV-1$_{NL4-3}$ reporter viruses which carry the lu164 gene (luciferase 164) instead of the nef gene are used for this assay. The viruses are generated by transfection of 293T cells with the corresponding proviral pNL4-3 plasmid (Lipofectamine Reagent, Invitrogen, Karlsruhe, Germany). Starting from the proviral plasmid DNA using the "QuikChange II XL Site-Directed Mutagenesis Kit" (Stratagene, Cedar Creek, Tex., USA) viruses with defined resistance mutations in the reverse transcriptase gene are provided. The following mutations, inter alia, are generated: A98G, A98G-K103N-V108I, A98S, F227C, F227L, G190A, G190S, K101E, K101Q-K103N, K103N, K103N-F227L, K103N-G190A, K103N-G190S, K103N-M230L, K103N-N348I, K103N-P225H, K103N-V108I, K103N-V108I-P225H, K103N-V179F-Y181C, K103N-Y181C, K103N-Y181C-G190A, L100I, L100I-K103N, L100I-K103N-V179I-Y181C, L100I-K103N-Y181C, L234I, N348I, P225H, P236L, V106A, V106A-E138K, V106A-F227C, V106A-F227L, V106I, V106I-Y188L, V106M, V108I, V179F-Y181C, V179I, V179I-Y181C, Y181C, Y181C-G190A, Y181C-M230L, Y181I, Y188L. MT4 7F2 cells infected with these reporter viruses secrete luciferase into the medium, thus enabling virus replication to be quantified by luminometry.

For the mixture for a 96-well MTP, 3 million MT4 7F2 cells are pelleted, suspended in 1 ml of RPMI 1640 medium without phenol red (Invitrogen, Karlsruhe, Germany)/10% FCS/ 10% AIM-V (Invitrogen, Karlsruhe, Germany) and incubated together with a suitable amount of the corresponding HIV-$1_{NL4-3}$ reporter virus at 37° C. for 2 hours (pellet infection). Unadsorbed viruses are subsequently washed out with PBS, and the infected cells are pelleted again and suspended in 8 ml of RPMI 1640 medium without phenol red/2% or 10% FCS/ 10% AIM-V. 80 µl thereof are pipetted into each well of a white 96-well MTP with 20 µl of test substance in suitable dilution. To avoid edge effects, the wells on the edge of the MTP are not used for substance dilutions. The second vertical row of the MTP contains only infected cells (virus control) and the eleventh vertical row only uninfected cells (cell control), in each case in RPMI 1640 medium without phenol red/2% or 10% FCS/10% AIM-V. The other wells of the MTP contain the compounds of the invention in various concentrations starting from the third vertical row, from which the test substances are diluted in 3-fold steps up to the tenth vertical row $3^7$-fold. The test substances are dissolved in DMSO, whereby the final DMSO concentration in the test mixture eventually is 1%. The test mixtures are incubated at 37° C./5% $CO_2$ for five days and, after the addition of 15 µl of Lu164 substrate (5 mg/ml coelenterazine dissolved in 30 µM glutathione/DMSO, 100 mM NaCl, 1M MES, 100 mM glutathione), evaluated by luminometry. The resulting values are in the region of 1 000 000 RLUs (relative light units) for the virus control and 300 to 400 RLUs for the cell control. The $EC_{50}$ values of the test substances are determined as the concentration at which the virus replication measured in RLUs is 50% of the untreated infected cells.

It is found that the compounds of the invention inhibit the HIV replication. Experimental data are summarized in Table A.

PBL and H9 Assay with Wild-Type HIV-1

Primary human blood lymphocycles (PBLs) are isolated from blood using Ficoll-Paque Leucosep tubes (Greiner Bio-One, Frickenhausen, Germany) and stimulated with phytohaemagglutinin (90 µg/ml) and interleukin-2 (40 U/ml) in RPMI 1640 medium (Invitrogen, Karlsruhe, Germany)/10% FCS for 3 days.

For the mixture for a 96-well MTP, 3 million PBLs are pelleted, suspended in 1 ml of RPMI 1640 medium/10% FCS and incubated together with a suitable amount of HIV-$1_{LAI}$ (NIH AIDS Research & Reference Reagent Program, Germantown, USA) at 37° C. for 2 hours (pellet infection). Unadsorbed viruses are subsequently washed out with PBS, and the infected cells are pelleted again and suspended in 18 ml of RPMI 1640 medium/10% FCS/interleukin-2 (40 U/ml). 180 µl thereof are pipetted into each well of a white 96-well MTP with 20 µl of test substance in suitable dilution. Alternatively, after preparation of the substance dilutions in the MTP, the HIV is pipetted in together with the cells and is not washed out again (supernatant infection). In order to avoid edge effects, the wells at the edge of the MTP are not used for substance dilutions. The second vertical row of the MTP contains only infected cells (virus control) and the eleventh vertical row only uninfected cells (cell control), in each case in RPMI 1640 medium/10% FCS/interleukin-2 (40 U/ml). The other wells of the MTP contain the compounds of the invention in various concentrations starting from the third vertical row, from which the test substances are diluted in 3-fold steps up to the tenth vertical row $3^7$-fold. The test substances are dissolved in DMSO, whereby the final DMSO concentration in the test mixture eventually is 1%. The test mixtures are incubated at 37° C./5% $CO_2$. After 5 and 7 days, 50 µl of cell-free supernatant are removed from each well to determine the amount of p24 present by means of a p24 ELISA (HIV-1 p24$^{CA}$ Antigen Capture Assay Kit, NCI-Frederick Cancer Research and Development Center, Frederick, USA). From the resulting values of the photometric evaluation (450/620 nm) the $EC_{50}$ values of the test substances are determined as the concentration at which the amount of p24 is 50% of the untreated infected cells.

Alternatively, H9 cells (ATCC, Wesel, Germany) are employed instead of PBLs for testing the test substances. H9 cells are incubated in RPMI 1640 medium with 2% or 10% FCS as a HIV-$1_{LAI}$ supernatant infection at 37° C./5% $CO_2$, (20 µl of substance dilution and 80 µl of cells/virus per well) in accordance with the pattern described above for 5 days. Subsequently, 10 µl of AlamarBlue (Invitrogen, Karlsruhe, Germany) are added to each well, and the MTPs are incubated at 37° C. for 3 hours before the fluorimetric evaluation takes place (544/590 nm). The resulting values are about 40 000 for the untreated uninfected cells and about 7000 for the untreated infected cells. In the low concentration range, the $EC_{50}$ values of the test substances are determined as the concentration at which the fluorescence is 50% of the untreated uninfected cells (in each case subtracting the values of the untreated infected cells). In addition, in the high concentration range, the $CC_{50}$ values of the test substances are determined as the concentration at which the fluorescence is 50% of the untreated uninfected cells (in each case subtracting the values of the untreated infected cells).

It is found that the compounds of the invention inhibit the HIV replication. Experimental data are summarized in Table A.

Assay to Determine the Cytotoxic Effect of the Test Substances

To determine the cytotoxic effect of the test substances in uninfected cells, the substances are pipetted in appropriate concentrations into transparent 96-well MTPs and incubated with uninfected cells (e.g. H9, PBLs, THP-1, MT4 7F2, CEM, Jurkat) (in analogy to the assays described above). After 5 days, per each well 1/10 of the volume AlamarBlue is added to the test mixtures, and the MTPs are incubated at 37° C. for 3 hours. The fluorimetric evaluation (544/590 nm) subsequently takes place. The resulting values are between 20 000 and 40 000 for untreated cells, depending on the type of cell. The $CC_{50}$ values of the test substances are determined as the concentration at which the fluorescence is 50% of the untreated cells. Test substances which show cytotoxic findings in the concentration range of the effect are not evaluated for their antiviral activity.

TABLE A

| Example No. | $IC_{50}$ (nM) RT Assay | $EC_{50}$ (nM) H9 cells HIV-$1_{LAI}$ 10% FCS | $EC_{50}$ (nM) MT4 7F2 cells HIV-$1_{NL4-3}$ wt 2% FCS | $EC_{50}$ (nM) MT4 7F2 cells HIV-$1_{NL4-3}$ K103N-Y181C 2% FCS |
|---|---|---|---|---|
| Example 53 | 46 | 1 | 0.3 | 33 |
| Example 33 | 8 | 0.5 | 0.07 | 3 |
| Example 22 | 131 | 2 | 0.3 | 10 |
| Example 52 | 38 | 2 | 0.1 | 17 |

TABLE A-continued

| Example No. | $IC_{50}$ (nM) RT Assay | $EC_{50}$ (nM) H9 cells HIV-1$_{LAI}$ 10% FCS | $EC_{50}$ (nM) MT4 7F2 cells HIV-1$_{NL4-3}$ wt 2% FCS | $EC_{50}$ (nM) MT4 7F2 cells HIV-1$_{NL4-3}$ K103N-Y181C 2% FCS |
|---|---|---|---|---|
| Example 2 | 34 | 0.2 | 0.06 | 11 |
| Example 1 | 38 | 2 | 0.2 | 3 |
| Example 21 | 59 | 3 | 1 | 38 |
| Example 25 | 99 | 2 | 0.6 | 30 |
| Example 26 | 104 | 11 | 2 | 65 |
| Example 32 | 65 | 0.7 | 0.1 | 25 |
| Example 36 | 52 | 3 | 0.6 | 45 |
| Example 30 | 297 | 8 | 3 | 16 |
| Example 38 | 365 | 120 | 9 | 80 |
| Example 3 | 37 | 0.2 | 0.03 | 7 |
| Example 4 | 75 | 11 | 1 | 45 |
| Example 51 | 60 | 1 | 0.4 | 15 |
| Example 37 | 175 | 33 | 18 | 2000 |
| Example 60 | 9 | 0.9 | 0.1 | 4 |
| Example 59 | 8 | 1 | 0.2 | 10 |
| Example 56 | 14 | 0.1 | 0.03 | 12 |
| Example 61 | 35 | 3 | 1 | 80 |
| Example 62 | 49 | 9 | 2 | 63 |
| Example 63 | 102 | 150 | 20 | 237 |
| Example 64 | 25 | 100 | 5 | 250 |

In Vivo Assay

Animal Model:

NOD Scid mice, usually 5-6 weeks old, are purchased from commercial breeders (e.g. Taconic or Jackson Laboratory). The animals are kept under sterile conditions (including bedding and feed) in isolators.

A defined number of cells (e.g. $5 \times 10^6$ T cells (e.g. C8166)) is infected with HIV with a suitable m.o.i. (e.g. 0.01 $TCID^{50}$). The infected cells are introduced into collagen sponges. The sponges pretreated in this way are implanted under the dorsal skin of the mice. The mice are treated once or several times each day orally, intraperitoneally, subcutaneously or intravenously, whereby it is possible that the first treatment takes place before the implantation. The treatment groups usually include 10 mice. At least one group is treated with placebo, at least one group with a substance known to be active (=positive control) and usually several groups with the substance of the invention. The daily dose of the substance of the invention is between 0.01 mg and 100 mg per kg of body weight. The substances are formulated in 2% DMSO/0.5% methylcellulose in PBS or another suitable mixture which assists the solubility of the substances. The treatment usually lasts four and a half days. After the last administration of the substance, the animals are sacrificed and the sponges are removed. The virus-infected cells are obtained from the sponge by collagenase digestion.

The total RNA is obtained from the cells and is examined by quantitative PCR for the content of viral RNA. The amount of viral RNA is normalized on the basis of the amount of a housekeeping gene (e.g. GAPDH). The amount of HIV RNA after treatment with the substance compared with the placebo-treated control group is determined. If an HIV carrying a luciferase was used it is possible in addition or as substitute to carry out a luciferase measurement. In this case, the amount of HIV is determined from the level of the luciferase signal because it serves as a measure of the viral replication in this case. Statistical analysis takes place by means of suitable computer programs, e.g. Graph Pad Prism.

B) Assessment of the Pharmacokinetic Properties

In Vivo Studies

To determine the in vivo pharmacokinetics, the test substances are administered intravenously and orally to mice, rats and dogs. The dose chosen in intravenous studies for determining the pharmacokinetic properties of the test substances is 0.5 mg/kg in all species. On oral administration, 3 mg/kg is administered to the rodents, and 1 mg/kg to dogs. The test substances are formulated in 99% plasma, 1% DMSO for the intravenous administration for rodents, and in PEG 400, ethanol and water in varying proportions for oral administration. The latter vehicle is used for both administration routes for dogs.

Male Wistar rats are catheterized before the administration of the test substances so that the blood samples can be taken with the aid of the catheter in place or by puncture of the vena cava at various times over an interval of from 2 min up to 26 h.

The test substances are administered to female BalbC mice intravenously as bolus injection, and in this case samples are obtained exclusively by puncture of the vena cava over an interval of from 2 min up to 26 h. Administration to female beagle dogs exclusively takes place by a 15-minute intravenous infusion. The samples are obtained by puncture of the brachial vein or the jugular vein over an interval of from 10 min up to 26 h.

The substances are quantitatively determined from the animal plasma obtained and calibration samples adjusted in plasma. The plasma proteins are removed by precipitation with acetonitrile (ACN). The samples are subsequently fractionated by HPLC on an Agilent 1100 LC system (Agilent, Santa Clara, Calif., USA) using various columns, e.g. Luna C8, LichroCart Purospher Star RP18e. The HPLC system is coupled via a Turbo Ion Spray interface to an API 3000 triple quadropole mass spectrometer (Applied Biosystems, Darmstadt, Germany). The evaluation of the plasma concentration-time course takes place by employing an internal standard and using a validated kinetic analysis program.

Besides studies to determine the pharmacokinetic parameters of the test substances in vivo, determinations of the relative bioavailability from suspension (formulation: Tylose suspension) versus solution in the rat as well as high-dose studies preliminary to tests of effect and toxicological studies in mice, rats and dogs are carried out.

Plasma Stability

The plasma used from the various species (BalbC mouse, Wistar rat, beagle dog and human) is obtained fresh by taking blood into monovettes coated with Li-heparin and subsequent centrifugation. In order to determine the plasma stability of the test substances 2 ml containing in each case 500 ng/ml in plasma are incubated at 37° C. Samples are taken from the incubation vessel at various times over an interval of up to 3 h. The samples obtained are precipitated with ACN in order to stop the reaction and remove the plasma proteins. The samples are analysed in a manner equivalent to the in vivo studies.

Microsomal and Hepatocyte Incubations

Incubations with liver microsomes of various species (BalbC mouse, Wistar rat, beagle dog, human) are carried out in a total volume of 1.5 ml at 37° C. in a modified Multiprobe II® robot system (Canberra Packard) or Janus® robot system (Perkin Elmer).

The incubation mixtures each comprise 0.5 μg/ml test substance as well as 0.2-0.5 mg/ml microsomal protein. In addition, 0.05 M phosphate buffer (pH=7.4), 1 mM EDTA, 5 mM glucose 6-phosphate and 1.5 U/ml glucose-6-phosphate dehydroxygenase from *Leuconostoc Mesenteroides* are added. The microsomal incubations are started by adding NADP+ (final concentration: 1 mM).

In each case 1 million cells/ml are used to determine the metabolic stability of the test substances in freshly isolated and cultivated rat, dog and human hepatocytes. In a manner equivalent to the microsomal assay, in each case 0.5 μg/ml test substance are added to the hepatocytes.

125 μl are removed from the respective incubation mixture after 2, 5, 10, 20, 30, 45 and 60 min, or after 2, 10, 20, 30, 50, 70 and 90 min for more stable compounds, and ACN is added in order to stop the enzymatic reactions. After centrifugation, the samples are analysed by LC-MS/MS (API 2000 or 3000, Applied Biosystems). "$CL_{blood}$ well-stirred" and "$F_{max}$ well-stirred" values are calculated from the respective half-lives of the compounds in the microsomal incubations. The substrate degradation can be described by the following formulae (Houston J B, Utility of in-vitro drug-metabolism data in predicting in-vivo metabolic-clearance, Bioch. Pharm. 47 (9) 1469-1479 (1994); Obach R S; Baxter J G; Liston T E; Silber B M; Jones B C; MacIntyre F; Rance D J; Wastall P, The prediction of human pharmacokinetic parameters from preclinical and in vitro metabolism data, J. Pharmacol. Exp. Ther. 283 (1) 46-58 (1997)):

$CL'_{intrinsic}$ [ml/(min·g)]=(0.693/in vitro $t_{1/2}$ [min])·
 (liver weight [g liver/kg body weight])·(microsomal protein [mg]/liver weight [g])/
 (microsomal protein [mg]/incubation volume [ml]).

The blood clearance "$CL_{blood}$" is described by the well-stirred model, ignoring protein bindings (Pang K S; Rowland M, Hepatic clearance of drugs. I. Theoretical considerations of a "well-stirred" model and a "parallel tube" model. Influence of hepatic blood flow, plasma and blood cell binding, and the hepatocellular enzymatic activity on hepatic drug clearance, J Pharmacokinet Biopharm 5 (6): 625-53 (1977)):

$CL_{blood}$ well-stirred [l/(h·kg)]=
 ($Q_H$ [l/(h·kg)]·$CL'_{intrinsic}$ [l/(h·kg)])/ ($Q_H$ [l/(h·kg)]+$CL'_{intrinsic}$ [l/(h·kg)]).

For rats, the specific liver weight is 32 g/kg of body weight and the hepatic blood flow is 4.2 l/(h·kg). The specific microsomal protein content of the rat liver was estimated at 40 mg/g of liver. The specific extrapolation factors for further species are shown in the following table and are based in part on literature data and in part on our own determinations. For hepatocytes a cell count of 110 million/g of liver is used for the calculation for all species.

|  | Mouse m | Mouse f | Rat m | Dog m/f | Human m/f |
|---|---|---|---|---|---|
| Microsomal protein/g of liver [mg] | 40 | 40 | 40 | 40 | 40 |
| Liver [g]/kg of body weight | 50 | 43 | 32 | 39 | 21 |
| Liver blood flow [l/(h · kg)] | 5.4 | 5.4 | 4.2 | 2.1 | 1.32 |

C) Exemplary Embodiments of Pharmaceutical Compositions

The compounds of the invention can be converted into pharmaceutical preparations in the following ways:

Tablet:

Composition:

100 mg of the compound of Example 1, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% solution (m/m) of the PVP in water. After drying the granules are mixed with the magnesium stearate for 5 minutes. This mixture is compressed using a conventional tablet press (see above for format of the tablet). A guideline compressive force for the compression is 15 kN.

Solution which can be Administered Orally:

Composition:

500 mg of the compound of Example 1, 2.5 g of polysorbate and 97 g of polyethylene glycol 400.20 g of oral solution correspond to a single dose of 100 mg of the compound of the invention.

Production:

The compound of the invention is suspended in the mixture of polyethylene glycol and polysorbate with stirring. The stirring process is continued until the compound of the invention has completely dissolved.

i.v. Solution:

The compound of the invention is dissolved in a concentration below the saturation solubility in a physiologically acceptable solvent (e.g. isotonic saline solution, 5% glucose solution, 30% PEG 400 solution). The solution is sterilized by filtration and dispensed into sterile and pyrogen-free injection containers.

What is claimed is:

1. A compound of formula (I)

in which $R^1$ represents phenyl,
 whereby phenyl is substituted with 1 to 3 substituents,
  whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy,
wherein
$(C_1-C_4)$-alkyl and $(C_1-C_4)$-alkoxy in turn may be substituted once to three times, identically or differently, with radicals selected from the series halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl,
whereby the last-mentioned cycloalkyl and heterocyclyl radicals in turn may each be substituted up to three times, identically or differently, with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino,
$R^2$ represents phenyl,
whereby phenyl is substituted with 1 to 3 substituents, whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy,
wherein
$(C_1-C_4)$-alkyl and $(C_1-C_4)$-alkoxy in turn may be substituted once to three times, identically or differently, with radicals selected from the series halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl,
whereby the last-mentioned cycloalkyl and heterocyclyl radicals in turn may each be substituted up to three times, identically or differently, with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino,
or a salt thereof.

2. The compound of claim 1, whereby
$R^1$ represents phenyl,
whereby phenyl is substituted with 1 to 2 substituents, whereby the substituents are selected independently of one another from the group consisting of halogen, hydroxy, cyano, nitro, trifluoromethyl, trifluoromethoxy, trifluoromethylthio, $(C_1-C_4)$-alkyl and $(C_1-C_4)$-alkoxy,
$R^2$ represents phenyl,
whereby phenyl is substituted with 1 to 2 substituents, whereby the substituents are selected independently of one another from the group consisting of halogen, hydroxy, cyano, nitro, trifluoromethoxy, trifluoromethylthio, $(C_1-C_4)$-alkyl and $(C_1-C_4)$-alkoxy,
wherein
$(C_1-C_4)$-alkoxy in turn may be substituted once to three times, identically or differently, with radicals selected from the series halogen, cyano, hydroxy, $(C_1-C_4)$-alkoxy, amino, mono-$(C_1-C_4)$-alkylamino, di-$(C_1-C_4)$-alkylamino, $(C_3-C_7)$-cycloalkyl and 4- to 7-membered heterocyclyl,
whereby the last-mentioned cycloalkyl and heterocyclyl radicals in turn may each be substituted up to three times, identically or differently, with halogen, cyano, $(C_1-C_4)$-alkyl, trifluoromethyl, hydroxy, $(C_1-C_4)$-alkoxy, trifluoromethoxy, oxo, amino, mono-$(C_1-C_4)$-alkylamino and di-$(C_1-C_4)$-alkylamino,
or a salt thereof.

3. The compound of claim 1, whereby
$R^1$ represents phenyl,
whereby phenyl is substituted with 1 to 2 substituents, whereby the substituents are selected independently of one another from the group consisting of halogen, cyano, trifluoromethyl and methoxy,
$R^2$ represents phenyl,
whereby phenyl is substituted with 1 to 2 substituents, whereby the substituents are selected independently of one another from the group consisting of halogen, cyano, trifluoromethoxy, methyl and $(C_1-C_3)$-alkoxy,
wherein
$(C_1-C_3)$-alkoxy in turn may be substituted once to three times, identically or differently, with radicals selected from the series hydroxy, $(C_1-C_4)$-alkoxy, amino, mono-$(C_1-C_4)$-alkylamino, di-$(C_1-C_4)$-alkylamino and 4- to 7-membered heterocyclyl,
whereby the last-mentioned heterocyclyl radicals may in turn each be substituted with $(C_1-C_4)$-alkyl,
or a salt thereof.

4. The compound of claim 1, whereby
$R^1$ represents phenyl,
whereby phenyl is substituted with 1 to 2 substituents, whereby the substituents are selected independently of one another from the group consisting of halogen, cyano, trifluoromethyl and methoxy,
$R^2$ represents phenyl,
whereby phenyl is substituted with 1 to 2 substituents, whereby the substituents are selected independently of one another from the group consisting of halogen, cyano, trifluoromethoxy, methyl and methoxy,
or a salt thereof.

5. The compound of claim 1, whereby
$R^1$ represents phenyl,
whereby phenyl is substituted with 1 to 2 substituents, whereby the substituents are selected independently of one another from the group consisting of halogen and cyano,
$R^2$ represents phenyl,
whereby phenyl is substituted with 1 to 2 substituents, whereby the substituents are selected independently of one another from the group consisting of halogen and cyano,
or a salt thereof.

6. The compound of claim 1, corresponding to formula

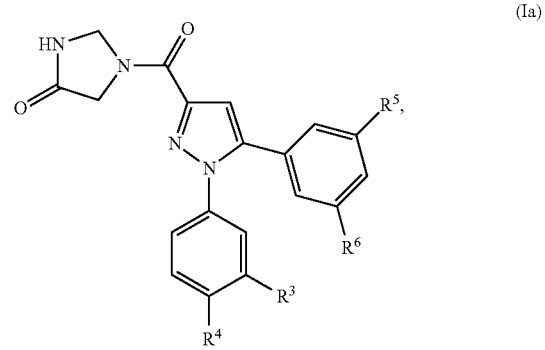

(Ia)

in which
$R^3$ represents hydrogen, halogen, hydroxy, cyano, nitro, trifluoromethyl, trifluoromethoxy, trifluoromethylthio, $(C_1-C_4)$-alkyl or $(C_1-C_4)$-alkoxy, $R^4$ represents hydrogen or halogen, $R^5$ represents halogen, hydroxy, cyano, nitro, trifluoromethyl, trifluoromethoxy, trifluoromethylthio, ($C_1$-$C_4$)-alkyl or ($C_1$-$C_4$)-alkoxy, wherein ($C_1$-$C_4$)-alkoxy in turn may be substituted once to three times, identically or differently, with radicals selected from the series halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl and 4- to 7-membered heterocyclyl, whereby the last-mentioned cycloalkyl and heterocyclyl radicals in turn may each be substituted up to three times, identically or differently, with halogen, cyano, ($C_1$-$C_4$)-alkyl, trifluoromethyl, hydroxy, ($C_1$-$C_4$)-alkoxy, trifluoromethoxy, oxo, amino, mono-($C_1$-$C_4$)-alkylamino and di-($C_1$-$C_4$)-alkylamino, $R^6$ represents hydrogen or halogen, or a salt thereof.

7. The compound of claim 6, whereby $R^3$ represents halogen, hydroxy, cyano, nitro, trifluoromethyl, trifluoromethoxy, trifluoromethylthio, ($C_1$-$C_4$)-alkyl or ($C_1$-$C_4$)-alkoxy, $R^4$ represents hydrogen or halogen, $R^5$ represents halogen, hydroxy, cyano, nitro, trifluoromethoxy, trifluoromethylthio, ($C_1$-$C_4$)-alkyl or ($C_1$-$C_4$)-alkoxy, wherein ($C_1$-$C_4$)-alkoxy in turn may be substituted once to three times, identically or differently, with radicals selected from the series halogen, cyano, hydroxy, ($C_1$-$C_4$)-alkoxy, amino, mono-($C_1$-$C_4$)-alkylamino, di-($C_1$-$C_4$)-alkylamino, ($C_3$-$C_7$)-cycloalkyl and 4- to 7-membered heterocyclyl, whereby the last-mentioned cycloalkyl and heterocyclyl radicals in turn may each be substituted up to three times, identically or differently, with halogen, cyano, ($C_1$-$C_4$)-alkyl, trifluoromethyl, hydroxy, ($C_1$-$C_4$)-alkoxy, trifluoromethoxy, oxo, amino, mono-($C_1$-$C_4$)-alkylamino and di-($C_1$-$C_4$)-alkylamino, $R^6$ represents hydrogen or halogen, or a salt thereof.

8. The compound of claim 6, whereby $R^3$ represents halogen, cyano, trifluoromethyl or methoxy, $R^4$ represents hydrogen or halogen, $R^5$ represents halogen, cyano, trifluoromethoxy, methyl or ($C_1$-$C_3$)-alkoxy, wherein ($C_1$-$C_3$)-alkoxy in turn may be substituted once to three times, identically or differently, with radicals selected from the series hydroxy, ($C_1$-$C_4$)-alkoxy, amino, mono-($C_1$-$C_4$)-alkylamino, di-($C_1$-$C_4$)-alkylamino and 4- to 7-membered heterocyclyl, whereby the last-mentioned heterocyclyl radicals in turn may each be substituted with ($C_1$-$C_4$)-alkyl, $R^6$ represents hydrogen or halogen, or a salt thereof.

9. The compound of claim 6, whereby $R^3$ represents halogen, cyano, trifluoromethyl or methoxy, $R^4$ represents hydrogen, chlorine or fluorine, $R^5$ represents halogen, cyano, trifluoromethoxy, methyl or methoxy, $R^6$ represents hydrogen, chlorine or fluorine, or a salt thereof.

10. The compound of claim 6, whereby $R^3$ represents halogen or cyano, $R^4$ represents hydrogen or fluorine, $R^5$ represents halogen or cyano, $R^6$ represents hydrogen or fluorine, or a salt thereof.

11. The compound of claim 6, whereby $R^3$ represents chlorine or cyano, $R^4$ represents fluorine, $R^5$ represents chlorine or cyano, $R^6$ represents fluorine, or a salt thereof.

12. The compound of claim 6, whereby $R^3$ represents chlorine or cyano, $R^4$ represents fluorine, $R^5$ represents chlorine or cyano, $R^6$ represents hydrogen, or a salt thereof.

13. The compound of claim 6, whereby $R^3$ represents chlorine or cyano, $R^4$ represents hydrogen, $R^5$ represents chlorine or cyano, $R^6$ represents hydrogen, or a salt thereof.

14. The compound of claim 6, whereby $R^3$ represents chlorine or cyano, $R^4$ represents hydrogen, $R^5$ represents chlorine or cyano, $R^6$ represents fluorine, or a salt thereof.

15. The compound of claim 6, whereby $R^3$ represents halogen, cyano, trifluoromethyl or methoxy, $R^4$ represents hydrogen or halogen, $R^5$ represents trifluoromethyl, $R^6$ represents fluorine, or a salt thereof.

16. The compound of claim 6, whereby $R^3$ represents hydrogen, $R^4$ represents fluorine or chlorine, $R^5$ represents halogen, cyano, trifluoromethoxy, methyl or methoxy, $R^6$ represents hydrogen or halogen, or a salt thereof.

17. A method for preparing a compound of formula (I) of claim 1, whereby a compound of formula (II)

![structure of compound II: HO-C(=O)-pyrazole with N-R¹ and R²]

in which $R^1$ and $R^2$ have the meaning indicated in claim 1, is reacted with imidazolidin-4-one or a salt of imidazolidin-4-one.

18. A method for manufacturing a medicament, comprising mixing a compound of claim 1 with at least one inert non-toxic pharmaceutically acceptable excipient.

19. A medicament comprising at least one compound of claim 1 in combination with at least one further active ingredient.

20. A medicament comprising at least one compound of claim 1 in combination with at least one inert, non-toxic, pharmaceutically acceptable excipient.

21. A method for controlling retroviral diseases in humans and animals by administering an antivirally effective amount of at least one compound according to claim 1 to a human or animal in need thereof.

22. The method of claim 21, whereby the retroviral disease is an infection with the HI virus.

23. A method for controlling retroviral diseases in humans and animals by administering an antivirally effective amount of a medicament according to claim 19 to a human or animal in need thereof.

24. The method of claim 23, whereby the retroviral disease is an infection with the HI virus.

25. A method for controlling retroviral diseases in humans and animals by administering an antivirally effective amount of a medicament according to claim 20 to a human or animal in need thereof.

26. The method of claim 25, whereby the retroviral disease is an infection with the HI virus.

* * * * *